United States Patent
Coleman et al.

(10) Patent No.: US 12,178,869 B2
(45) Date of Patent: Dec. 31, 2024

(54) RECOMBINANT VIRUS WITH CODON-PAIR DEOPTIMIZED REGION AND USES THEREOF FOR THE TREATMENT OF CANCER

(71) Applicant: CODAGENIX INC., Farmingdale, NY (US)

(72) Inventors: John Robert Coleman, New York, NY (US); Steffen Mueller, Great Neck, NY (US); Chen Yang, Plainview, NY (US); Ying Wang, South Setauket, NY (US); Charles Stauft, Wheatley Heights, NY (US)

(73) Assignee: CODAGENIX INC., Farmingdale, NY (US)

( * ) Notice: Subject to any disclaimer, the term of this patent is extended or adjusted under 35 U.S.C. 154(b) by 159 days.

(21) Appl. No.: 16/769,102

(22) PCT Filed: Dec. 21, 2018

(86) PCT No.: PCT/US2018/067174
§ 371 (c)(1),
(2) Date: Jun. 2, 2020

(87) PCT Pub. No.: WO2019/126690
PCT Pub. Date: Jun. 27, 2019

(65) Prior Publication Data
US 2021/0228705 A1    Jul. 29, 2021

Related U.S. Application Data

(60) Provisional application No. 62/609,945, filed on Dec. 22, 2017, provisional application No. 62/640,362, filed on Mar. 8, 2018, provisional application No. 62/677,132, filed on May 28, 2018, provisional application No. 62/640,355, filed on Mar. 8, 2018.

(51) Int. Cl.
| | |
|---|---|
| *A61K 39/145* | (2006.01) |
| *A61K 39/13* | (2006.01) |
| *C12N 7/00* | (2006.01) |
| *A61K 39/00* | (2006.01) |
| *A61K 39/395* | (2006.01) |

(52) U.S. Cl.
CPC ............ *A61K 39/13* (2013.01); *A61K 39/145* (2013.01); *C12N 7/00* (2013.01); *A61K 39/39558* (2013.01); *A61K 2039/5254* (2013.01); *A61K 2039/812* (2018.08); *A61K 2039/86* (2018.08); *A61K 2039/876* (2018.08); *C12N 2760/16132* (2013.01); *C12N 2770/24134* (2013.01); *C12N 2770/32632* (2013.01)

(58) Field of Classification Search
None
See application file for complete search history.

(56) References Cited

U.S. PATENT DOCUMENTS

| | | |
|---|---|---|
| 5,494,671 A | 2/1996 | Lai et al. |
| 5,744,140 A | 4/1998 | Paoletti et al. |
| 5,824,506 A | 10/1998 | Chan et al. |
| 8,846,051 B2 | 9/2014 | Kew et al. |
| 9,476,032 B2 | 10/2016 | Wimmer et al. |
| 9,957,486 B2 | 5/2018 | Collins et al. |
| 10,023,845 B2 | 7/2018 | Wimmer et al. |
| 10,316,294 B2 | 6/2019 | Mueller et al. |
| 10,695,414 B2 | 6/2020 | Kew et al. |
| 10,808,012 B2 | 10/2020 | Lenouen et al. |
| 2008/0118530 A1 | 5/2008 | Om et al. |
| 2008/0286848 A1 | 11/2008 | Skiadopoulos et al. |
| 2009/0092635 A1 | 4/2009 | Clarke et al. |
| 2010/0008946 A1 | 1/2010 | Szalay et al. |
| 2010/0062532 A1 | 3/2010 | Jin et al. |

(Continued)

FOREIGN PATENT DOCUMENTS

| | | |
|---|---|---|
| CA | 3091508 A | 12/2019 |
| CN | 104204196 A2 | 12/2014 |

(Continued)

OTHER PUBLICATIONS

Broadbent et al. Evaluation of the attenuation, immunogenicity, and efficacy of a live virus vaccine generated by codon-pair bias de-optimization of the 2009 pandemic H1N1 influenzavirus, infer-rets. Vaccine 34 (2016) 563-570.*

(Continued)

*Primary Examiner* — Nianxiang Zou

(74) *Attorney, Agent, or Firm* — Linda B. Huber; Nixon Peabody LLP

(57) ABSTRACT

The present invention is the use of designed recombinant viruses for the treatment of various forms of malignant tumors. The recombinant viruses of the invention are those in which one or more regions of the wild type virus was exchanged with a synthetic recoded sequence that reduces the codon pair score relative to human codon pair bias, or that increase the number for CpG di-nucleotides, or that increases the number of UpA di-nucleotides. The method of the present invention is particularly useful for the treatment of malignant tumors in various organs, such as: breast, skin, colon, bronchial passage, epithelial lining of the gastrointestinal, upper respiratory and genito-urinary tracts, liver, prostate and the brain. Astounding remissions in experimental animals have been demonstrated for the treatment of malignant glioblastoma multiforme, as well as for the treatment of breast cancer and melanoma as well.

11 Claims, 30 Drawing Sheets

Specification includes a Sequence Listing.

(56) References Cited

U.S. PATENT DOCUMENTS

| | | |
|---|---|---|
| 2010/0166769 A1 | 7/2010 | Hsiao et al. |
| 2012/0009215 A1 | 1/2012 | Yang et al. |
| 2014/0023680 A1 | 1/2014 | Yang et al. |
| 2014/0242102 A1 | 8/2014 | Yang et al. |
| 2014/0356962 A1* | 12/2014 | Wimmer ............... A61P 31/14 435/236 |
| 2015/0307851 A1 | 10/2015 | Kawaoka et al. |
| 2015/0368622 A1 | 12/2015 | Collins et al. |
| 2016/0367656 A9 | 12/2016 | Bonaldo et al. |
| 2017/0067030 A1 | 3/2017 | Wimmer et al. |
| 2017/0143780 A1 | 5/2017 | Zitvogel et al. |
| 2017/0290808 A1 | 10/2017 | Charo et al. |
| 2018/0008689 A1 | 1/2018 | Vignuzzi et al. |
| 2018/0201908 A1 | 7/2018 | Nougairéde et al. |
| 2018/0207295 A1 | 7/2018 | Fotin-Mleczek et al. |
| 2018/0208906 A1 | 7/2018 | Collins et al. |
| 2018/0245052 A1* | 8/2018 | Egorov ............... C12N 7/00 |
| 2019/0002837 A1 | 1/2019 | Wimmer et al. |
| 2019/0151365 A1* | 5/2019 | Anak ............... A61P 35/02 |
| 2019/0275139 A1 | 9/2019 | Yu et al. |
| 2020/0268865 A1 | 8/2020 | Kew et al. |
| 2021/0000939 A1 | 1/2021 | Coleman et al. |
| 2022/0160863 A1 | 5/2022 | Muster et al. |
| 2023/0000971 A1 | 1/2023 | Rockman et al. |
| 2023/0340423 A1 | 10/2023 | Coleman et al. |

FOREIGN PATENT DOCUMENTS

| | | |
|---|---|---|
| CN | 102753200 B | 11/2017 |
| CN | 108290932 A | 7/2018 |
| CN | 111481663 A | 8/2020 |
| CN | 112040977 A | 12/2020 |
| EP | 2465927 B1 | 6/2012 |
| EP | 3727442 | 10/2020 |
| EP | 3762021 | 1/2021 |
| EP | 3515930 A1 | 9/2022 |
| EP | 4061930 A1 | 9/2022 |
| IN | 202027030412 A | 10/2020 |
| IN | 202027038754 A | 10/2020 |
| JP | 2000502889 A1 | 3/2000 |
| JP | 2002513575 A | 5/2002 |
| JP | 2009518007 A | 5/2009 |
| JP | 2009534039 A | 9/2009 |
| JP | 2010523086 A | 7/2010 |
| JP | 2011505863 A | 3/2011 |
| JP | 4771959 B2 | 9/2011 |
| JP | 2012510283 A | 5/2012 |
| JP | 4980895 B2 | 7/2012 |
| JP | 2012519484 A | 8/2012 |
| JP | 2012531205 A | 12/2012 |
| JP | 2013179943 A | 9/2013 |
| JP | 5349049 B2 | 11/2013 |
| JP | 2015501141 A | 1/2015 |
| JP | 2015502158 A | 1/2015 |
| JP | 2015091247 A | 5/2015 |
| JP | 5733976 B2 | 6/2015 |
| JP | 2015524266 A | 8/2015 |
| JP | 2017524693 A | 8/2017 |
| JP | 2020502080 A | 1/2020 |
| JP | 2021508696 A | 3/2021 |
| KR | 2020103020 | 9/2020 |
| RU | 2020132280 A | 4/2022 |
| WO | 2007104782 A1 | 9/2007 |
| WO | 2011044561 A1 | 4/2011 |
| WO | 2013090795 A1 | 6/2013 |
| WO | 2013138670 A1 | 9/2013 |
| WO | 2016037187 A1 | 3/2016 |
| WO | 2016120412 A1 | 8/2016 |
| WO | 2017078577 | 5/2017 |
| WO | 2018057950 A1 | 3/2018 |
| WO | 2019126690 A | 6/2019 |
| WO | 2019126690 A1 | 6/2019 |
| WO | 2019172982 A1 | 9/2019 |
| WO | 2020232254 A1 | 11/2020 |
| WO | 2020263850 A1 | 12/2020 |
| WO | 2022011032 A1 | 1/2022 |
| WO | 2022051327 A1 | 3/2022 |
| WO | 2023102520 A1 | 6/2023 |
| WO | 2023205689 A2 | 10/2023 |

OTHER PUBLICATIONS

Masemann et al. Oncolytic influenza virus infection restores immunocompetence of lung tumor-associated alveolar macrophages. Oncoimmunology 2018, vol. 7, No. 5, e1423171 (13 pages).*

International Search Report and Written Opinion for PCT/US2018/67114 dated May 23, 2019, 15 pages.

International Search Report and Written Opinion of PCT/US2018/67174, dated May 17, 2019, 15 Pages.

International Search Report and Written Opinion of PCT/US2020/32901, dated Septemeber 1, 2020, 8 Pages.

Woodson et al., Infection of hepatocytes with 17-D vaccine-strain yellow fever virus induces a strong pro-inflammatory host response, Journal of General Virology, 2011, vol. 92(10), pp. 2262-2271.

International Search Report and Written Opinion of PCT/US2020/39166, dated Septemeber 24, 2020, 12 Pages.

Nouen et al., Attenuation of human respiratory syncytial virus by genome-scale codon-pair deoptimization, PNAS, 2014, vol. 111

(56) References Cited

OTHER PUBLICATIONS

Nogales et al., Influenza A virus attenuation by codon deoptimization of the NS gene for vaccine development, J. Virol., 2014, vol. 88, No. 18, pp. 10525-10540.
Shen et al., Large-scale recoding of an arbovirus genome to rebalance its insect versus mammalian preference, Proc. Natl. Acad. Sci. USA, 2015, vol. 112, No. 15, pp. 4749-4754.
Coleman et al., Virus Attenuation by Genome-Scale Changes in Codon Pair Bias, Science, 2008, vol. 320, pp. 1784-1787.
Mueller et al., Live attenuated influenza virus vaccines by computer-aided rational design, Nature Biotechnology, 2010, vol. 28(7), pp. 723-726.
Supplementary European Search Report for EP 18908620 dated Dec. 23, 2021.
Li et al., Zika Virus Attenuation by Codon Pair Deoptimization Induces Sterilizing Immunity in Mouse Models, Journal of Virology, 2018, vol. 92(17), pp. 1-16.
Asif et al., Zika Virus: Immune Evasion Mechanisms, Currently Available Therapeutic Regimens, and Vaccines, Viral Immunology, 2017, vol. 30(10), pp. 682-690.
Extended Europen Search Report for EP 18891144 dated Mar. 3, 2022, 2 pages.
Burns et al., Genetic Inactivation of Poliovirus Infectivity by Increasing the Frequencies of CpG and UpA Dinucleotides within and across Synonymous Capsid Region Codons, Journal of Virology, 2009, vol. 83(19), pp. 9957-9969.
International Search Report and Written Opinion for PCT/US2021/040716 dasted Oct. 26, 2021, 10 pages.
Supplementary European Search Report for EP 18891144 dated Oct. 20, 2021, 10 pages.
Search Report for RU 2020124143 dated Feb. 28, 2022, 4 pages.
Exam Report for SA 520412310 dated Jun. 8, 2022.
De Jesus et al., Mutation of a Single Conserved Nucleotide between the Cloverleaf and Internal Ribosome Entry Site Attenuates Poliovirus Neurovirulence, Journal of Virology, 2005, vol. 79(22), pp. 14235-14243.
Anonymous, Directive 2001/83/EC of the European Parliament and of the Council of Nov. 6, 2001 on the Community code relating to medicinal products for human use, Official Journal of the European Communities, 2001.
Anonymous, Guidance for Industry Characterization and Qualification of Cell Substrates and Other Biological Materials Used in the Production of Viral Vaccines for Infectious Disease Indications, U.S. Department of Health and Human Services Food and Drug Administration Center for Biologics Evaluation and Research, 2010, pp. 1-47.
Gao et al., HP-PRRSV is attenuated by de-optimization of codon pair bias in its RNA-dependent RNA polymerase hsp9 gene, Virology 485, 2015, pp. 135-144.
Influenza A virus (A/Gs/HK/739.2/02(H5N1)) nucleocapsit protein (NP) gene, complete cds, GenBank: AY575907.2, 2 pages.
Martrus et al., Changes in codon-pair bias of human immunodeficiency virus type 1 have profound effects on virus replication in cell culture, Retrovirology, 2013, vol. 10(78), pp. 1-12.
Influenza A virus (A/PuertoRico/8/34/Mount Sinai (H1N1)) segment 5, complete sequence, GenBank: AF389119.1, 2 pages.
Influenza A virus (A/swine/Germany/SIV05/2007(H1N1)) segement 5, complete sequence, genomic RNA, GenBank: FN429082.1, 2 pages.
Gao et al., HP-PRRSV is attenuated by de-optimization of codon pair bias in its RNA-dependent RNA polymerase hsp9 gene, Virology 485, 2015, pp. 135-144, Supplementary table.
Pattnaik et al., Current Status of Zika Virus Vaccines: Successes and Challenges, Vaccines 2020, vol. 8(266), pp. 1-19.
Guo et al., Oncolytic Immunotherapy: Conceptual Evolution, Current Strategies, and Future Perspectives, Frontiers in Immunology, 2017, vol. 8(555), pp. 1-15.
Search Report in Malaysia Application No. PI2020004620 dated Dec. 13, 2023, 4 pp.
Search Report and Written Opinion for Singapore 11202008126Q dated Mar. 31, 2022.
Hock et al., Oncolytic influenza A virus expressing interleukin-15 decreases tumor growth in vivo, Surgery, 2017, vol. 161(3), pp. 735-746.
Bergmann et al.,A Genetically Engineered Influenza A Virus with ras-Dependent Oncolytic Properties, Cancer Research; 2001, vol. 61, pp. 8188-8193.

* cited by examiner

Virus Titer

| PV(M)-wt | |
|---|---|
| Wt | |
| PV-Max | |
| PV-Min | |
| PV-MinX | |
| PV-MinY | |
| PV-MinXY | |
| PV-MinZ | |
| PV-MinYZ | |

PFU/(ml)

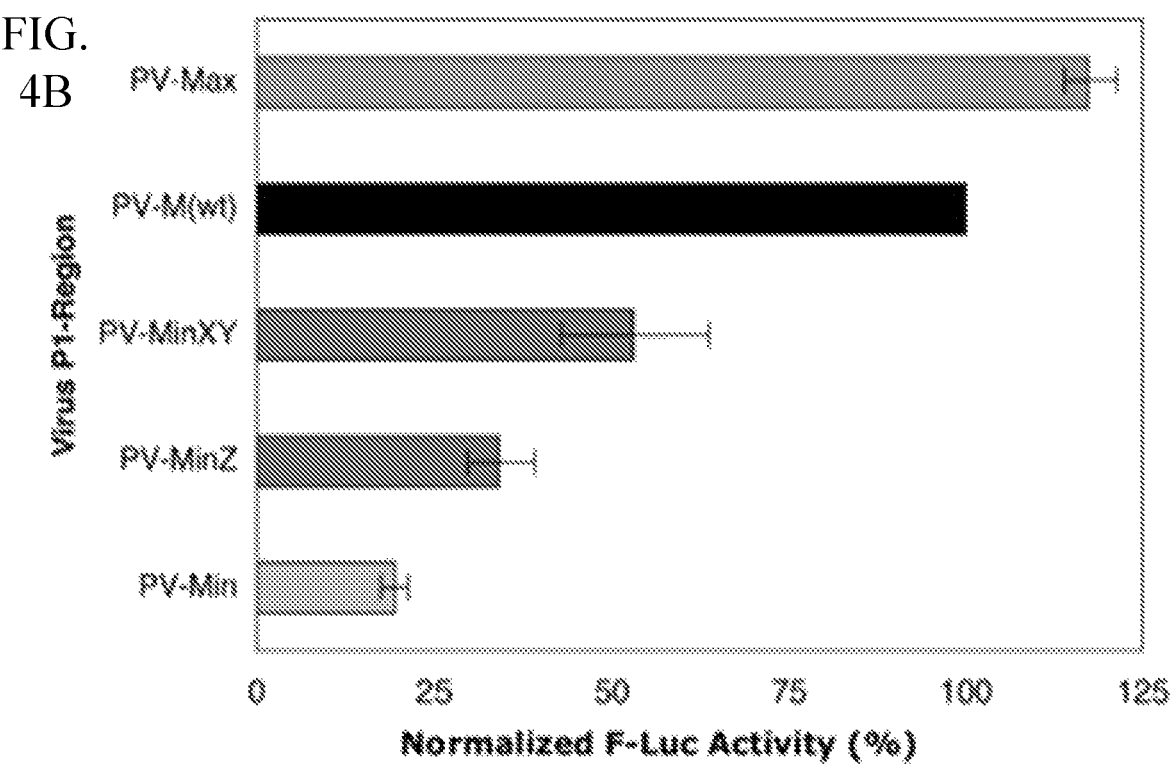

PR15 E-Min

5'—[C|M| E | NS1 |NS2A|NS2B| NS3 |NS4A|NS4B| NS5 ]—3'

PR15 NS3-Min

5'—[C|M| E | NS1 |NS2A|NS2B| NS3 |NS4A|NS4B| NS5 ]—3'

PR15 E+NS3-Min

5'—[C|M| E | NS1 |NS2A|NS2B| NS3 |NS4A|NS4B| NS5 ]—3'

MR766 WT

5'—[C|M| E | NS1 |NS2A|NS2B| NS3 |NS4A|NS4B| NS5 ]—3'

MR766 E-Min

5'—[C|M| E | NS1 |NS2A|NS2B| NS3 |NS4A|NS4B| NS5 ]—3'

MR766 NS3-Min

5'—[C|M| E | NS1 |NS2A|NS2B| NS3 |NS4A|NS4B| NS5 ]—3'

MR766 E+NS3-Min

PRVABC59   MR766 min   wt   min   wt   ctrl

- ● $10^2$ MR766-Syn-WT
- ■ $10^2$ MR766-EMin
- ▲ $10^4$ MR766-EMin
- ▼ $10^4$ MR766-NS3Min
- ◆ $10^2$ PR15-Syn-WT
- ○ $10^2$ PR15-EMin
- ▱ $10^4$ PR15-EMin
- △ $10^4$ PR15-NS3+EMin
- ▽ Mock Y-axis: Percent survival (%)
X-axis: DPI

FIG. 14

5'─────[ prM + E genes | NS Genes ]─────3'
W-E-Min, 997 bp deoptimized

Pre-vaccinations | Xenograft | Treatment #1 #2 #3 | END 0    14    26   //   71    85    96   103  107   117

Weigh mice daily ─ ─ ─→          105 ─ ─ → Measure tumor size daily

FIG. 15

Day 0          Day 5

W-E-Min

FIG. 16

Zika MR766 W-W-Emin Immunized

FIG. 17

Zika MR766 W-Emin & W-W-Emin Immunized

FIG. 31E

CD45+
1 Day post treatment

Mock:Mock

Mock:WWE-Zika

WE-Zika:WWE-Zika

FIG. 31F

CD8+
7 Day post treatment

Mock:Mock

Mock:WWE-Zika

WE-Zika:WWE-Zika

SEQUENCE LISTING

```
<160> NUMBER OF SEQ ID NOS: 6

<210> SEQ ID NO 1
<211> LENGTH: 7440
<212> TYPE: DNA
<213> ORGANISM: Artificial Sequence
<220> FEATURE:
<223> OTHER INFORMATION: Synthetic Construct

<400> SEQUENCE: 1
ttaaaacagc tctggggttg tacccacccc agaggcccac gtggcggcta gtactccggt      60
attgcggtac ccttgtacgc ctgttttata ctcccttccc gtaacttaga cgcacaaaac     120
caagttcaat agaagggggt acaaaccagt accaccacga acaagcactt ctgtttcccc     180
ggtgatgtcg tatagactgc ttgcgtggtt gaaagcgacg gatccgttat ccgcttatgt     240
acttcgagaa gcccagtacc acctcggaat cttcgatgcg ttgcgctcag cactcaaccc     300
cagagtgtag cttaggctga tgagtctgga catccctcac cggtgacggt ggtccaggct     360
gcgttggcgg cctacctatg gctaacgcca tgggacgcta gttgtgaaca aggtgtgaag     420
agcctattga gctacataag aatcctccgg cccctgaatg cggctaatcc caacctcgga     480
gcaggtggtc acaaaccagt gattggcctg tcgtaacgcg caagtccgtg gcggaaccga     540
ctactttggg tgtccgtgtt tccttttatt ttattgtggc tgcttatggt gacaatcaca     600
gattgttatc ataaagcgaa ttggattggc catccggtga aagtgagact cattatctat     660
ctgtttgctg gatccgctcc attgagtgtg tttactctaa gtacaatttc aacagttatt     720
tcaatcagac aattgtatca taatgggtgc tcaggtttca tcacagaaag tgggcgcaca     780
```

```
tgaaaactca aatagagcgt atggtagttc taccattaat tacaccacca ttaattatta    840
tagagattca gctagtaacg cggcttcgaa acaggacttc tctcaagacc cttccaagtt    900
caccgagccc atcaaggatg tcctgataaa aacagcccca atgctaaact cgccaaacat    960
agaggcttgc gggtatagcg atagagtact gcaattaaca ctgggaaact ccactataac   1020
cacacaggag gcggctaatt cagtagtcgc ttatgggcgt tggcctgaat atctgaggga   1080
cagcgaagcc aatccagtgg accagccgac agaaccagac gtcgctgcat gcaggtttta   1140
tacgctagac accgtgtctt ggacgaaaga gtcgcgaggg tggtggtgga agttgcctga   1200
tgcactgagg gacatgggac tctttgggca aaatatgtac taccactacc taggtaggtc   1260
cgggtacacc gtgcatgtac agtgtaacgc ctccaaattc caccaggggg cactaggggt   1320
attcgccgta ccagagatgt gtctggccgg ggatagcaac accactacca tgcacaccag   1380
ctatcaaaat gccaatcctg gcgagaaagg aggcactttc acgggtacgt tcactcctga   1440
caacaaccag acatcacctg cccgcaggtt ctgcccggtg gattacctcc ttggaaatgg   1500
cacgttgttg gggaatgcct tcgtattccc acaccagata attaacttac ggactaacaa   1560
ttgcgcaacc ctagtgttgc catacgttaa ctcactgtca atcgatagta tggtgaaaca   1620
taacaattgg gggatcgcaa tattaccgtt agcgccactg aatttcgcca gcgaatcgtc   1680
acctgagata ccgattaccc ttacaatcgc acctatgtgt tgcgagttca acggattgcg   1740
taatataacc ctaccacggt tgcaggggtt gcccgttatg aatacccag ggtctaacca   1800
ataccttacc gccgataatt tccaatcccc ttgcgcactg ccagagttcg acgtaacccc   1860
tccaatcgac atacccggcg aggttaagaa tatgatggag ttagccgaaa tcgatactat   1920
gataccgttc gatctatccg ctacgaaaaa gaatactatg gagatgtatc gcgtgagatt   1980
gtccgataag ccacataccg acgatccgat actgtgtctg tcactgtcac ccgccagcga   2040
tcctaggttg tcccatacaa tgttaggcga gatactgaat tactataccc attgggccgg   2100
tagtctgaaa ttcacatttc tgttttgcgg atctatgatg gcgaccggaa agctgttagt   2160
gtcatacgct ccacccggag ccgatccacc taaaaaacgc aaggaagcga tgctcggtac   2220
acacgtgata tgggatatcg gactgcaatc gtcatgtact atggtcgtgc catggatatc   2280
gaatacgact tatagacaga caatcgacga tagctttacc gagggggggt atattagcgt   2340
attctatcag acacgtatcg tagtgccact gtcaaccccct agagagatgg acatactcgg   2400
attcgtatcc gcatgtaacg actttagcgt gagactgtta cgcgatacta cccatatcga   2460
acagaaagcg ctagcacagg ggttaggtca gatgcttgaa agcatgattg acaacacagt   2520
ccgtgaaacg gtggggcgg caacatctag agacgctctc ccaaacactg aagccagtgg   2580
accaacacac tccaaggaaa ttccggcact caccgcagtg gaaactgggg ccacaaatcc   2640
actagtccct tctgatacag tgcaaaccag acatgttgta caacataggt caaggtcaga   2700
gtctagcata gagtctttct tcgcgcgggg tgcatgcgtg accattatga ccgtggataa   2760
cccagcttcc accacgaata aggataagct ttttgcagtg tggaagatca cttataaaga   2820
tactgtccag ttacggagga aattggagtt cttcacctat tctagatttg atatggaact   2880
tacctttgtg gttactgcaa atttcactga gactaacaat ggccatgcat taaatcaagt   2940
gtaccaaatt atgtacgtac caccaggcgc tccagtgccc gaaaaatggg acgactacac   3000
atggcaaacc tcatcaaatc catcaatctt ttacacctac gggacagctc cagcccggat   3060
ctcggtaccg tatgttggta tttcgaacgc ctattcacac ttttacgacg gttttccaa   3120
```

-continued

```
agtaccactg aaggaccagt cggcagcact aggtgactcc ctttatggtg cagcatctct    3180
aaatgacttc ggtatttttgg ctgttagagt agtcaatgat cacaacccga ccaaggtcac   3240
ctccaaaatc agagtgtatc taaaacccaa acacatcaga gtctggtgcc cgcgtccacc    3300
gagggcagtg gcgtactacg gccctggagt ggattacaag gatggtacgc ttacacccct    3360
ctccaccaag gatctgacca catatggatt cggacaccaa acaaagcgg tgtacactgc     3420
aggttacaaa atttgcaact accacttggc cactcaggat gatttgcaaa acgcagtgaa    3480
cgtcatgtgg agtagagacc tcttagtcac agaatcaaga gcccagggca ccgattcaat    3540
cgcaaggtgc aattgcaacg caggggtgta ctactgcgag tctagaagga aatactaccc    3600
agtatccttc gttggcccaa cgttccagta catggaggct aataactatt acccagctag    3660
gtaccagtcc catatgctca ttggccatgg attcgcatct ccaggggatt gtggtggcat    3720
actcagatgt caccacgggg tgatagggat cattactgct ggtggagaag ggttggttgc    3780
attttcagac attagagact tgtatgccta cgaagaagaa gccatggaac aaggcctcac    3840
caattacata gagtcacttg gggccgcatt tggaagtgga tttactcagc agattagcga    3900
caaaataaca gagttgacca atatggtgac cagtaccatc actgaaaagc tacttaagaa    3960
cttgatcaag atcatatcct cactagttat taaactagg aactatgaag acaccacaac    4020
agtgctcgct accctggccc ttcttgggtg tgatgcttca ccatggcagt ggcttagaaa    4080
gaaagcatgc gatgttctgg agataccta tgtcatcaag caaggtgaca gttggttgaa    4140
gaagtttact gaagcatgca acgcagctaa gggactggag tgggtgtcaa acaaaatctc    4200
aaaattcatt gattggctca aggagaaaat tatcccacaa gctagagata gttggaatt    4260
tgtaacaaaa cttagacaac tagaaatgct ggaaaaccaa atctcaacta cacaccaatc    4320
atgccctagt caggaacacc aggaaattct attcaataat gtcagatggt tatccatcca    4380
gtctaagagg tttgcccctc tttacgcagt ggaagccaaa agaatacaga actcgagca    4440
tactattaac aactcatac agttcaagag caaacaccgt attgaaccag tatgtttgct     4500
agtacatggc agccccggaa caggtaaatc tgtagcaacc aacctgattg ctagagccat    4560
agctgaaaga gaaaacacgt ccacgtactc gctaccccg gatccatcac acttcgacgg     4620
atacaaacaa cagggagtgg tgattatgga cgacctgaat caaaacccag atggtgcgga    4680
catgaagctg ttctgtcaga tggtatcaac agtggagttt ataccaccca tggcatccct    4740
ggaggagaaa ggaatcctgt ttacttcaaa ttacgttcta gcatccacaa actcaagcag    4800
aatttccccc cccactgtgg cacacagtga cgcgttagcc aggcgctttg cgttcgacat    4860
ggacattcag gtcatgaatg agtattctag agatgggaaa ttgaacatgg ccatggctac    4920
tgaaatgtgt aagaactgtc accaaccagc aaactttaag agatgctgtc ctttagtgtg    4980
tggtaaggca attcaattaa tggacaaatc ttccagagtt agatacagta ttgaccagat    5040
cactacaatg attatcaatg agagaaacag aagatccaac attggcaatt gtatggaggc    5100
tttgtttcaa ggaccactcc agtataaaga cttgaaaatt gacatcaaga cgagtcccc    5160
tcctgaatgt atcaatgact tgctccaagc agttgactcc caggaggtga gagattactg    5220
tgagaagaag ggttggatag ttaacatcac cagccaggtt caaacagaaa ggaacatcaa    5280
cagggcaatg acaattctac aagcggtgac aaccttcgcc gcagtggctg gagttgtcta    5340
tgtcatgtat aaactgttg ctggacacca gggagcatac actggtttac caaacaaaaa    5400
acccaacgtg cccaccattc ggacagcaaa ggtacaagga ccagggttcg attacgcagt    5460
ggctatggct aaaagaaaca ttgttacagc aactactagc aagggagagt tcactatgtt    5520
```

| | |
|---|---|
| aggagtccac gacaacgtgg ctattttacc aacccacgct tcacctggtg aaagcattgt | 5580 |
| gatcgatggc aaagaagtgg agatcttgga tgccaaagcg ctcgaagatc aagcaggaac | 5640 |
| caatcttgaa atcactataa tcactctaaa gagaaatgaa aagttcagag acattagacc | 5700 |
| acatatacct actcaaatca ctgagacaaa tgatggagtc ttgatcgtga acactagcaa | 5760 |
| gtaccccaat atgtatgttc ctgtcggtgc tgtgactgaa cagggatatc taaatctcgg | 5820 |
| tgggcgccaa actgctcgta ctctaatgta caactttcca accagagcag acagtgtgg | 5880 |
| tggagtcatc acatgtactg ggaaagtcat cgggatgcat gttggtggga acggttcaca | 5940 |
| cgggttttgca gcggccctga agcgatcata cttcactcag agtcaaggtg aaatccagtg | 6000 |
| gatgagacct tcgaaggaag tgggatatcc aatcataaat gccccgtcca aaccaagct | 6060 |
| tgaacccagt gctttccact atgtgtttga agggtgaag gaaccagcag tcctcactaa | 6120 |
| aaacgatccc aggcttaaga cagactttga ggaggcaatt ttctccaagt acgtgggtaa | 6180 |
| caaaattact gaagtggatg agtacatgaa agaggcagta gaccactatg ctggccagct | 6240 |
| catgtcacta gacatcaaca tagaacaaat gtgcttggag gatgccatgt atggcactga | 6300 |
| tggtctagaa gcacttgatt tgtccaccag tgctggctac ccttatgtag caatgggaaa | 6360 |
| gaagaagaga gacatcttga acaaacaaac cagagacact aaggaaatgc aaaaactgct | 6420 |
| cgacacatat ggaatcaacc tcccactggt gacttatgta aaggatgaac ttagatccaa | 6480 |
| aacaaaggtt gagcagggga atccagatt aattgaagct tctagtttga atgactcagt | 6540 |
| ggcaatgaga atggcttttg gaacctata tgctgctttt cacaaaaacc caggagtgat | 6600 |
| aacaggttca gcagtggggt gcgatccaga tttgtttgg agcaaaattc cggtattgat | 6660 |
| ggaagagaag ctgtttgctt ttgactacac agggtatgat gcatctctca gccctgcttg | 6720 |
| gttcgaggca ctaaagatgg tgcttgagaa aatcggattc ggagacagag ttgactacat | 6780 |
| cgactaccta aaccactcac accacctgta caagaataaa acatactgtg tcaagggcgg | 6840 |
| tatgccatct ggctgctcag gcacttcaat ttttaactca atgattaaca acttgattat | 6900 |
| caggacactc ttactgaaaa cctacaaggg catagattta gaccacctaa aaatgattgc | 6960 |
| ctatggtgat gatgtaattg cttcctaccc ccatgaagtt gacgctagtc tcctagccca | 7020 |
| atcaggaaaa gactatggac taactatgac tccagctgac aaaatcagcta catttgaaac | 7080 |
| agtcacatgg gagaatgtaa cattcttgaa gagattcttc agggcagacg agaaataccc | 7140 |
| atttcttatt catccagtaa tgccaatgaa ggaaattcat gaatcaatta gatggacaaa | 7200 |
| agatcctagg aacactcagg atcacgttcg ctctctgtgc cttttagctt ggcacaatgg | 7260 |
| cgaagaagaa tataacaaat tcctagctaa aatcaggagt gtgccaattg aagagctt | 7320 |
| attgctccca gagtactcaa cattgtaccg ccgttggctt gactcatttt agtaacccta | 7380 |
| cctcagtcga attggattgg gtcatactgt tgtagggta aattttcttt taattcggag | 7440 |

<210> SEQ ID NO 2
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 2

| | |
|---|---|
| agttgttgat ctgtgtgagt cagactgcga cagttcgagt ctgaagcgag agctaacaac | 60 |
| agtatcaaca ggtttaattt ggatttggaa acgagagttt ctggtcatga aaacccaaa | 120 |

```
gaagaaatcc ggaggattcc ggattgtcaa tatgctaaaa cgcggagtag cccgtgtaaa    180
cccttgggga ggtttgaaga ggttgccagc cggacttctg ctgggtcatg gacccatcag   240
aatggttttg gcgatactag cctttttgag atttacagca atcaagccat cactgggcct    300
tatcaacaga tggggttccg tggggaaaaa agaggctatg gaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagccgaaat    480
tacgagaagg gggtccgcat actatatgta tctggatagg tccgacgccg gtaaggcaat    540
ctcattcgca acgacactcg gagtgaataa gtgtcacgtt cagattatgg acttagggca    600
tatgtgcgac gctactatgt catacgaatg ccctatgctt gacgaaggcg ttgagccaga    660
cgacgtcgac tgttggtgca atacgactag cacatgggtc gtgtacgta catgccatca     720
caaaagggc gaagcgagac ggtctagaag ggccgttacg ttgccgtcac actctacgag     780
aaagttgcag actaggtctc agacttggtt ggagtcacgc gaatacacta agcatctgat    840
taaggtcgag aattggattt ttaggaaccc agggttcgca ctagtcgccg tcgcaatcgc    900
ttggttgttg gggtctagta cgagtcagaa agtgatatac ttagtgatga tactgttgat    960
cgcacccgca tactctatta ggtgtatcgg agtgagtaat cgcgatttcg tcgagggtat    1020
gagcggaggg acatgggtcg acgttgtgct tgagcacggg gggtgcgtta ccgttatggc    1080
ccaagacaaa ccgacagtcg atatcgaact ggttacgact accgtttcga acatggccga    1140
agtgagatcg tattgttacg aggctagcat aagcgatatg gctagcgata gtaggtgccc    1200
aacacagggc gaagcgtatc tcgataagca atccgatacg caatacgttt gcaaacggac    1260
attggtcgat aggggtggg gtaacggatg cggactgttc ggtaaggggt cactagtgac     1320
atgcgctaag tttacatgct ctaaaaaaat gaccggtaag tcaatccaac ccgaaaacct    1380
tgagtatagg attatgttga gcgtacacgg atcgcaacac tccggtatga tcgttaacga    1440
taccggatac gagactgacg agaataggc taaggtcgag gtgacaccta actcacctag    1500
agccgaagcg acattggggg ggttcggatc tctcggactg gattgcgaac ctagaaccgg    1560
attggacttt agcgatctgt actatctgac tatgaacaat aagcattggt tggtgcataa    1620
ggagtggttt cacgacatac cactgccatg gcacgccgga gccgataccg gtacgccaca    1680
ttggaataac aaagaggcac tagtcgagtt taaggacgct cacgctaaga gacagaccgt    1740
agtcgtgttg gggtcacagg agggagccgt gcataccgca ctagccggcg cactcgaggc    1800
cgaaatggac ggagcgaaag ggagactgtt tagcggacac cttaagtgta gactgaaaat    1860
ggacaagttg cgacttaagg gcgttagcta tagcctatgt accgccgcat ttacgtttac    1920
gaaagtgcca gccgaaacgt tgcacggaac cgttaccgtc gaggtgcaat acgccggaac    1980
cgacggacca tgcaagatac ccgtgcaaat ggccgtcgat atgcagacac tgacaccagt    2040
cggacggttg attaccgcta acccagtgat aaccgagtca accgaaaact ctaagatgat    2100
gctcgagctt gacccaccat tcggcgactc atatatcgtt atcggagtcg gcgacaaaaa    2160
gattacgcat cattggcata gatccggatc gacaatcggt aaggcattcg aagcgacagt    2220
gagaggcgct aagcgtatgg ccgtattggg cgataccgca tgggacttcg gatcgtcgg    2280
cggagtgttt aactcactcg gtaaggggat acaccagata ttcggagccg cattcaaatc    2340
gttgttcggc ggaatgtcat ggtttagtca gatactgatc ggaacactgc ttgtgtggtt    2400
ggggttgaac actaagaacg gatcgattag tctgacatgc ttagcttag gcggagtgat     2460
gatttttctg tcaaccgccg ttagcgcaga cgtgggtgc tcagtggact tctcaaaaaa    2520
```

```
ggaaacgaga tgtggcacgg gggtattcat ctataatgat gtttgaagcct ggagggaccg    2580 gtacaagtac catcctgact cccccgcag attggcagca gcagtcaagc aggcctggga      2640 agagggatc tgtgggatct catccgtttc aagaatggaa aacatcatgt ggaaatcagt     2700
agaaggggag ctcaatgcta tcctagagga gaatggagtt caactgacag ttgttgtggg    2760
atctgtaaaa aaccccatgt ggagaggtcc acaaagattg ccagtgcctg tgaatgagct    2820
gccccatggc tggaaagcct gggggaaatc gtattttgtt agggcggcaa agaccaacaa    2880
cagttttgtt gtcgacggtg acacactgaa ggaatgtccg cttgagcaca gagcatggaa   2940
tagttttctt gtggaggatc acgggtttgg agtcttccac accagtgtct ggcttaaggt    3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa aacatgtgaa tggccaaagt ctcacacatt   3180
gtggacagat ggagtagaag aaagtgatct tatcataccc aagtctttag ctggtccact    3240
cagccaccac aacaccagag agggttacag aacccaagtg aaagggccat ggcacagtga   3300
agaacttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgccccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtgtcc ttcattttca gagccaattg    3840 gacacccgt gagagcatgc tgctagccct ggcttcgtgt cttctgcaaa ctgcgatctc    3900
tgctcttgaa ggtgacttga tggtcctcat taatgatttt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
ggccctggga ttgacagctg tgagggtagt agacccctatt aatgtggtag gactactgtt    4200
actcacaagg agtgggaagc ggagctggcc ccctagtgaa gttctcacag ccgttggcct    4260
gatatgtgca ctggccggag ggtttgccaa ggcagacatt gagatggctg gacccatggc    4320
tgcagtaggc ttgctaattg tcagctatgt ggtgtcggga aagagtgtgg acatgtacat    4380
tgaaagagca ggagacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560
tatacctttt gctgcaggag cgtggtatgt gtatgtgaag actgggaaaa ggagtggcgc    4620
cctctgggac gtgcctgctc ccaaagaagt gaagaaagga gaaaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
```

```
gaagttggat gcagcttggg atggactcag cgaggtacag cttttggccg tacctcccgg    4920
agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc cagggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctcaacat    5460
catggatgaa gcccacttca cagacccctc aagtatagct gcaagaggat acatatcaac    5520
aagggttgaa atgggcgagg cggctgccat ttttatgact gccacaccac caggaaccccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg aaagcgggt    5760
catacagctc agcaggaaga cttttgagac agaatttcag aaaacaaaaa atcaagagtg    5820
ggactttgtc ataacaactg acatctcaga tgggcgccc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taaggtagcc gccattgagg gagagtttaa    6180
gctgaggaca gagcaaagga agaccttcgt ggaactcatg aagagagggg accttcccgt    6240
ctggctagcc tatcaggttg catctgccgg aataacttac acagacagaa gatggtgctt    6300
tgatggcaca accaacaaca ccataatgga agacagcgta ccagcagagg tgtgacaaaa    6360
gtatggagag aagagagtgc tcaaaccgag atggatggat gctagggtct gttcagacca    6420
tgcggccctg aagtcgttca agaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagactctag agacaattat gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc atacccgagc cagaagcca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcaccccag ctgtccaaca    7080
tgcggtaacc acttcataca acaactactc cttaatggcg atggccacac aagctggagt    7140
gctgtttggc atgggcaaag gatgccatt ttatgcatgg gaccttggag tccgctgct    7200
aatgatgggt tgctattcac aattaacacc cctgactctg atagtagcta tcattctgct    7260
```

```
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag accccaggt ggagaagaag atgggacaag tgttactcat     7440
agcagtagcc atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag gacatgccgt atcccgggga agtgcaaagc tcagatggtt    7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggagg     8280 attagtcaga gtgccattgt ctcgcaactc cacacatgag atgtactggg tgtctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggttct tgatgaaaac cacccataca ggacatgggc     8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga agaggaaaaa gaatggaaga cggctgtgga    8940
agctgtgaat gatccaagt ttgggccct agtggatagg gagagagaac accacctgag      9000
aggagagtgt cacagctgtg tgtacaacat gatgggaaaa agagaaaaga agcaaggaga    9060
gttcgggaaa gcaaaggta gccgcgccat ctggtacatg tggttgggag ccagattctt     9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta tccggaacat    9540
ggaagctgag gaagtgttag agatgcaaga cttatggttg ttgaggaagc cagagaaagt    9600
```

| | |
|---|---:|
| gaccagatgg ttgcagagca atggatggga tagactcaaa cgaatggcgg tcagtggaga | 9660 |
| tgactgcgtt gtgaagccaa tcgatgatag gtttgcacat gccctcaggt tcttgaatga | 9720 |
| catgggaaaa gttaggaaag acacacagga gtggaaaccc tcgactggat ggagcaattg | 9780 |
| ggaagaagtc ccgttctgct cccaccactt caacaagctg tacctcaagg atgggagatc | 9840 |
| cattgtggtc ccttgccgcc accaagatga actgattggc cgagctcgcg tctcaccagg | 9900 |
| ggcaggatgg agcatccggg agactgcctg tcttgcaaaa tcatatgcgc agatgtggca | 9960 |
| gctcctttat ttccacagaa gggaccttcg actgatggct aatgccattt gctcggctgt | 10020 |
| gccagttgac tgggttccaa ctgggagaac cacctggtca atccatggaa agggagaatg | 10080 |
| gatgaccact gaggacatgc tcatggtgtg gaatagagtg tggattgagg agaacgacca | 10140 |
| tatggaggac aagactcctg taacaaaatg gacagacatt ccctatctag gaaaaaggga | 10200 |
| ggacttatgg tgtggatccc ttatagggca cagaccccgc accacttggg ctgaaaacat | 10260 |
| caaagacaca gtcaacatgg tgcgcaggat cataggtgat gaagaaaagt acatggacta | 10320 |
| tctatccacc caagtccgct acttgggtga ggaagggtcc acacccggag tgttgtaagc | 10380 |
| accaattta gtgttgtcag gcctgctagt cagccacagt ttggggaaag ctgtgcagcc | 10440 |
| tgtaaccccc ccaggagaag ctgggaaacc aagctcatag tcaggccgag aacgccatgg | 10500 |
| cacggaagaa gccatgctgc ctgtgagccc ctcagaggac actgagtcaa aaaccccac | 10560 |
| gcgcttggaa gcgcaggatg ggaaaagaag gtggcgacct tccccaccct tcaatctggg | 10620 |
| gcctgaactg gagactagct gtgaatctcc agcagaggga ctagtggtta gaggagaccc | 10680 |
| cccgaaaac gcacaacagc atattgacgc tgggaaagac cagagactcc atgagtttcc | 10740 |
| accacgctgg ccgccaggca cagatcgccg aacttcggcg gccggtgtgg ggaaatccat | 10800 |
| ggtttct | 10807 |

<210> SEQ ID NO 3
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 3

| | |
|---|---:|
| agttgttgat ctgtgtgagt cagactgcga cagttcgagt ctgaagcgag agctaacaac | 60 |
| agtatcaaca ggtttaattt ggatttggaa acgagagttt ctggtcatga aaacccaaa | 120 |
| gaagaaatcc ggaggattcc ggattgtcaa tatgctaaaa cgcggagtag cccgtgtaaa | 180 |
| cccccttgga ggtttgaaga ggttgccagc cggacttctg ctgggtcatg gacccatcag | 240 |
| aatggttttg gcgatactag cctttttgag atttacagca atcaagccat cactgggcct | 300 |
| tatcaacaga tgggggttccg tggggaaaaa agaggctatg gaaataataa agaagttcaa | 360 |
| gaaagatctt gctgccatgt tgagaataat caatgctagg aaagagagga gagacgtgg | 420 |
| cgcagacacc agcatcggaa tcattggcct cctgctgact acagccatgg cagcagagat | 480 |
| cactagacgc gggagtgcat actacatgta cttggatagg agcgatgccg gaaggccat | 540 |
| ttcgtttgct accacattgg gagtgaacaa gtgccacgta cagatcatgg acctcgggca | 600 |
| catgtgtgac gccaccatga gttatgagtg ccctatgctg gatgagggag tggaaccaga | 660 |
| tgatgtcgat tgctggtgca acacgacatc aacttgggtt gtgtacggaa cctgtcatca | 720 |
| caaaaaggt gaggcacggc gatctaggag agccgtgacg ctcccttctc actctacaag | 780 |
| gaagttgcaa acgcggtcgc agacctggtt agaatcaaga gaatacacga agcacttgat | 840 |

```
caaggttgaa aactggatat tcaggaaccc cgggtttgcg ctagtggccg ttgccattgc      900
ctggcttttg ggaagctcga cgagccaaaa agtcatatac ttggtcatga tactgctgat      960
tgccccggca tacagtatca ggtgcattgg agtcagcaat agagacttcg tggagggcat     1020
gtcaggtggg acctggggttg atgttgtctt ggaacatgga ggctgcgtta ccgtgatggc     1080
acaggacaag ccaacagttg acatagagtt ggtcacgacg acggttagta acatggccga     1140
ggtaagatcc tattgctacg aggcatcgat atcggacatg gcttcggaca gtcgttgccc     1200
aacacaaggt gaagcctacc ttgacaagca atcagacact caatatgtct gcaaaagaac     1260
attagtggac agaggttggg gaaacggttg tggactttttt ggcaaaggga gcttggtgac     1320
atgtgccaag tttacgtgtt ctaagaagat gaccggcaag agcattcaac cggaaaatct     1380
ggagtatcgg ataatgctat cagtgcatgg ctcccagcat agcgggatga ttgtcaatga     1440
tacaggatat gaaactgacg aaaatagagc gaaagtcgag gttacgccta actcacctag     1500
agccgaagcg acattggggg ggttcggatc tctcggactg gattgcgaac ctagaaccgg     1560
attggacttt agcgatctgt actatctgac tatgaacaat aagcattggt tggtgcataa     1620
ggagtggttt cacgacatac cactgccatg gcacgccgga gccgataccg gtacgccaca     1680
ttggaataac aaagaggcac tagtcgagtt taaggacgct cacgctaaga gacagaccgt     1740
agtcgtgttg gggtcacagg agggagccgt gcataccgca ctagccggcg cactcgaggc     1800
cgaaatggac ggagcgaaag ggagactgtt tagcggacac cttaagtgta gactgaaaat     1860
ggacaagttg cgacttaagg gcgttagcta tagcctatgt accgccgcat ttacgtttac     1920
gaaagtgcca gccgaaacgt tgcacggaac cgttaccgtc gaggtgcaat acgccggaac     1980
cgacggacca tgcaagatac ccgtgcaaat ggccgtcgat atgcagacac tgacaccagt     2040
cggacggttg attaccgcta acccagtgat aaccgagtca accgaaaact ctaagatgat     2100
gctcgagctt gacccaccat tcggcgactc atatatcgtt atcggagtcg gcgacaaaaa     2160
gattacgcat cattggcata gatccggatc gacaatcggt aaggcattcg aagcgacagt     2220
gagaggcgct aagcgtatgg ccgtattggg cgatacccgca tgggacttcg gatccgtcgg     2280
cggagtgttt aactcactcg gtaagggat acaccagata ttcggagccg cattcaaatc     2340
gttgttcggc ggaatgtcat ggtttagtca gatactgatc ggaacactgc ttgtgtggtt     2400
gggggttgaac actaagaacg gatcgattag tctgacatgc ttagccttag gcggagtgat     2460
gattttttctg tcaaccgccg ttagcgcaga cgtgggggtgc tcagtggact tctcaaaaaa     2520
ggaaacgaga tgtggcacgg gggtattcat ctataatgat gttgaagcct ggagggaccg     2580
gtacaagtac catcctgact ccccccgcag attggcagca gcagtcaagc aggcctggga     2640
agaggggatc tgtgggatct catccgtttc aagaatggaa aacatcatgt ggaaatcagt     2700
agaaggggag ctcaatgcta tcctagagga gaatggagtt caactgacag ttgttgtggg     2760
atctgtaaaa aaccccatgt ggagaggtcc acaaagattg ccagtgcctg tgaatgagct     2820
gccccatggc tggaaagcct gggggaaatc gtatttttgt agggcggcaa agaccaacaa     2880
cagtttttgtt gtcgacggtg acacactgaa ggaatgtccg cttgagcaca gagcatggaa     2940
tagttttctt gtggaggatc acgggttttgg agtcttccac accagtgtct ggcttaaggt     3000
cagagaagat tactcattag aatgtgaccc agccgtcata ggaacagctg ttaagggaag     3060
ggaggccgcg cacagtgatc tgggctattg gattgaaagt gaaaagaatg acacatggag     3120
gctgaagagg gcccacctga ttgagatgaa acatgtgaa tggccaaagt ctcacacatt     3180
```

```
gtggacagat ggagtagaag aaagtgatct tatcataccc aagtctttag ctggtccact    3240
cagccaccac aacaccagag agggttacag aacccaagtg aaagggccat ggcacagtga    3300
agaacttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtgtcc ttcattttca gagccaattg    3840 gacacccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
ggccctggga ttgacagctg tgagggtagt agaccctatt aatgtggtag actactgtt    4200 actcacaagg agtgggaagc ggagctggcc ccctagtgaa gttctcacag ccgttggcct    4260
gatatgtgca ctgccggag ggtttgccaa ggcagacatt gagatggctg acccatggc    4320 tgcagtaggc ttgctaattg tcagctatgt ggtgtcggga aagagtgtgg acatgtacat    4380
tgaaagagca ggagacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560 tataccttt gctgcaggag cgtggtatgt gtatgtgaag actgggaaaa ggagtggcgc    4620
cctctgggac gtgcctgctc ccaaagaagt gaagaaagga gaaaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctcccgg    4920
agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc caggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggcttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctcaacat    5460
catggatgaa gcccacttca cagacccctc aagtatagct gcaagaggat acatatcaac    5520
aagggttgaa atgggcgagg cggctgccat tttatgact gccacaccac caggaacccg    5580
```

```
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg gaaagcgggt   5760
catacagctc agcaggaaga cttttgagac agaatttcag aaaacaaaaa atcaagagtg   5820
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagagggg accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca agaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagactctag agacaattat gctcttaggt ttgctgggaa cagtttcact   6660
ggggatcttc ttcgtcttga tgcggaataa gggcatcggg aagatgggct ttggaatggt   6720
aacccttggg gccagtgcat ggctcatgtg gctttcggaa attgaaccag ccagaattgc   6780
atgtgtcctc attgttgtgt ttttattact ggtggtgctc atacccgagc cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agagaagaag gagcaaccat gggattctca atggacattg atctgcggcc   7020
agcctccgcc tgggctatct atgccgcatt gacaactctc atcaccccag ctgtccaaca   7080
tgcggtaacc acttcataca acaactactc cttaatggcg atggccacac aagctggagt   7140
gctgtttggc atgggcaaag gatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg cagcagcgc gtgctgccca   7320 gaaaaggaca gcagctggca tcatgaagaa tcccgttgtg gatggaatag tggtaactga   7380
cattgacaca atgacaatag acccccaggt ggagaagaag atgggacaag tgttactcat   7440
agcagtagcc atctccagtg ctgtgctgct gcggaccgcc tggggatggg gggaggctgg   7500
agctctgatc acagcagcga cctccaccct tgtgggaagg c tctccaaaca atactggaa   7560 ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag acatgccgt atcccgggga agtgcaaagc tcagatggtt   7860
ggtggagaga ggatatctgc agcccatgg gaaggttgtt gacctcggat gtggcagagg   7920
```

```
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggagg     8280 attagtcaga gtgccattgt ctcgcaactc cacacatgag atgtactggg tgtctggggc    8340
aaagagcaac atcataaaaa gtgtgtccac cacaagtcag ctcctcctgg gacgcatgga    8400
tggccccagg aggccagtga aatatgagga ggatgtgaac ctcggtcgg gtacacgagc     8460 tgtggcaagc tgtgctgagg ctcctaacat gaaaatcatc ggcaggcgca ttgagagaat    8520
ccgcaatgaa catcagaaaa catggtttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca caaggtgcg     8880 cagcaatgca gcactgggag caatatttga agaggaaaaa gaatgaaga cggctgtgga     8940 agctgtgaat gatccaaggt tttgggccct agtggatagg agagagaac accacctgag     9000 aggagagtgt cacagctgtg tgtacaacat gatgggaaaa agagaaaaga agcaaggaga    9060
gttcggaaaa gcaaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta tccggaacat    9540
ggaagctgag gaagtgttag agatgcaaga cttatggttg ttgaggaagc cagagaaagt    9600
gaccagatgt tgcagagca atggatggga tagactcaaa cgaatggcgg tcagtggaga    9660
tgactgcgtt gtgaagccaa tcgatgatag gttttgcacat gccctcaggt tcttgaatga    9720
catgggaaaa gttaggaaag acacacagga gtggaaaccc tcgactggat ggagcaattg    9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
ggcaggatgg agcatccggg agactgcctg tcttgcaaaa tcatatgcgc agatgtggca    9960
gctcctttat ttccacagaa gggaccttcg actgatggct aatgccattt gctcggctgt    10020
gccagttgac tgggttccaa ctgggagaac cacctggtca atccatggaa agggagaatg    10080
gatgaccact gaggacatgc tcatggtgtg aatagagtg tggattgagg agaacgacca     10140
tatggaggac aagactcctg taacaaaatg gacagacatt ccctatctag gaaaaaggga    10200
ggacttatgt gtgtggatcc cttatagggca cagacccgc accacttggg ctgaaaacat    10260
caaagacaca gtcaacatgg tgcgcaggat cataggtgat gaagaaagt acatggacta     10320
```

```
tctatccacc caagtccgct acttgggtga ggaagggtcc acacccggag tgttgtaagc  10380
accaatttta gtgttgtcag gcctgctagt cagccacagt ttggggaaag ctgtgcagcc  10440
tgtaaccccc ccaggagaag ctgggaaacc aagctcatag tcaggccgag aacgccatgg  10500
cacggaagaa gccatgctgc ctgtgagccc ctcagaggac actgagtcaa aaaccccac   10560 gcgcttggaa gcgcaggatg ggaaaagaag gtggcgacct tccccaccct tcaatctggg  10620
gcctgaactg gagactagct gtgaatctcc agcagaggga ctagtggtta gaggagaccc  10680
cccggaaaac gcacaacagc atattgacgc tgggaaagac cagagactcc atgagtttcc  10740
accacgctgg ccgccaggca cagatcgccg aacttcggcg ccggtgtgg  ggaaatccat  10800 ggtttct                                                            10807
```

<210> SEQ ID NO 4
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 4

```
agttgttgat ctgtgtgagt cagactgcga cagttcgagt ctgaagcgag agctaacaac    60
agtatcaaca ggtttaattt ggatttggaa acgagagttt ctggtcatga aaaacccaaa   120
gaagaaatcc ggaggattcc ggattgtcaa tatgctaaaa cgcggagtag cccgtgtaaa   180
cccctttgga ggtttgaaga ggttgccagc cggacttctg ctgggtcatg gacccatcag   240
aatggttttg gcgatactag ccttttttgag atttacagca atcaagccat cactgggcct   300
tatcaacaga tggggttccg tggggaaaaa agaggctatg gaaataataa agaagttcaa   360
gaaagatctt gctgccatgt tgagaataat caatgctagg aaagagagga agagacgtgg   420
cgcagacacc agcatcggaa tcattggcct cctgctgact acagccatgg cagcagagat   480
cactagacgc gggagtgcat actacatgta cttggatagg agcgatgccg ggaaggccat   540
ttcgtttgct accacattgg gagtgaacaa gtgccacgta cagatcatgg acctcgggca   600
catgtgtgac gccaccatga gttatgagtg ccctatgctg gatgagggag tggaaccaga   660
tgatgtcgat tgctggtgca acacgacatc aacttggggt tgtgtacgaa cctgtcatca   720 caaaaaggt gaggcacggc gatctaggag agccgtgacg ctcccttctc actctacaag   780
gaagttgcaa acgcggtcgc agacctggtt agaatcaaga gaatacgac agcacttgat   840 caaggttgaa aactggatat tcaggaaccc cgggtttgcg ctagtggccg ttgccattgc   900
ctggcttttg ggaagctcga cgagccaaaa agtcatatac ttggtcatga tactgctgat   960
tgccccggca tacagtatca ggtgcattgg agtcagcaat agagacttcg tggagggcat  1020
gtcaggtggg acctgggttg atgttgtctt ggaacatgga ggctgcgtta ccgtgatggc  1080
acaggacaag ccaacagttg acatagagtt ggtcacgacg acggttagta acatggccga  1140
ggtaagatcc tattgctacg aggcatcgat atcggacatg gcttcggaca gtcgttgccc  1200
aacacaaggt gaagcctacc ttgacaagca atcagacact caatatgtct gcaaagaac   1260 attagtggac agaggttggg gaaacggttg tggactttt  ggcaaaggga gcttggtgac  1320
atgtgccaag tttacgtgtt ctaagaagat gaccggcaag agcattcaac cggaaaatct  1380
ggagtatcgg ataatgctat cagtgcatgg ctcccagcat agcgggatga ttgtcaatga  1440
tacaggatat gaaactgacg aaaatagagc gaaagtcgag gttacgccta attcaccaag  1500
```

```
agcggaagca accttgggag gctttggaag cttaggactt gactgtgaac caaggacagg    1560
ccttgacttt tcagatctgt attacctgac catgaacaat aagcattggt tggtgcacaa    1620
agagtggttt catgacatcc cattgccttg gcatgctggg gcagacaccg gaactccaca    1680
ctggaacaac aaagaggcat tggtagaatt caaggatgcc cacgccaaga ggcaaaccgt    1740
cgtcgttctg gggagccagg aaggagccgt tcacacggct ctcgctggag ctctagaggc    1800
tgagatggat ggtgcaaagg ggagactgtt tagcggacac cttaagtgta gactgaaaat    1860
ggacaagttg cgacttaagg gcgttagcta tagcctatgt accgccgcat ttacgtttac    1920
gaaagtgcca gccgaaacgt tgcacggaac cgttaccgtc gaggtgcaat acgccggaac    1980
cgacggacca tgcaagatac ccgtgcaaat ggccgtcgat atgcagacac tgacaccagt    2040
cggacggttg attaccgcta acccagtgat aaccgagtca accgaaaact ctaagatgat    2100
gctcgagctt gacccaccat tcggcgactc atatatcgtt atcggagtcg gcgacaaaaa    2160
gattacgcat cattggcata gatccggatc gacaatcggt aaggcattcg aagcgacagt    2220
gagaggcgct aagcgtatgg ccgtattggg cgataccgca tgggacttcg gatccgtcgg    2280
cggagtgttt aactcactcg gtaaggggat acaccagata ttcggagccg cattcaaatc    2340
gttgttcggc ggaatgtcat ggtttagtca gatactgatc ggaacactgc ttgtgtggtt    2400
ggggttgaac actaagaacg gatcgattag tctgacatgc ttagccttag gcggagtgat    2460
gattttctg tcaaccgccg ttagcgcaga cgtggggtgc tcagtggact tctcaaaaaa    2520
ggaaacgaga tgtggcacgg gggtattcat ctataatgat gttgaagcct ggagggaccg    2580
gtacaagtac catcctgact ccccccgcag attggcagca gcagtcaagc aggcctggga    2640
agagggatc tgtgggatct catccgtttc aagaatggaa aacatcatgt ggaaatcagt    2700
agaagggag ctcaatgcta tcctagagga gaatggagtt caactgacag ttgttgtggg    2760
atctgtaaaa aaccccatgt ggagaggtcc acaaagattg ccagtgcctg tgaatgagct    2820
gccccatggc tggaaagcct gggggaaatc gtattttgtt agggcggcaa agaccaacaa    2880
cagttttgtt gtcgacggtg acacactgaa ggaatgtccg cttgagcaca gagcatggaa    2940
tagttttctt gtggaggatc acgggttttgg agtcttccac accagtgtct ggcttaaggt    3000
cagagaagat tactcattag aatgtgaccc agccgtcata ggaacagctg ttaagggaag    3060
ggaggccgcg cacagtgatc tgggctattg gattgaaagt gaaaagaatg acacatggag    3120
gctgaagagg gcccacctga ttgagatgaa acatgtgaa tggccaaagt ctcacacatt    3180
gtggacagat ggagtagaag aaagtgatct tatcataccc aagtctttag ctggtccact    3240
cagccaccac aacaccagag agggttacag aacccaagtg aaagggccat ggcacagtga    3300
agaacttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtgtcc ttcattttca gagccaattg    3840
gacaccccgt gagagcatgc tgctagccct ggcttcgtgt cttctgcaaa ctgcgatctc    3900
```

```
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
ggccctggga ttgacagctg tgagggtagt agaccctatt aatgtggtag gactactgtt    4200
actcacaagg agtgggaagc ggagctggcc ccctagtgaa gttctcacag ccgttggcct    4260
gatatgtgca ctggccggag ggtttgccaa ggcagacatt gagatggctg acccatggc    4320 tgcagtaggc ttgctaattg tcagctatgt ggtgtcggga aagagtgtgg acatgtacat    4380
tgaaagagca ggagacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560 tataccttt gctgcaggag cgtggtatgt gtatgtgaag actgggaaaa ggagtggcgc    4620
cctctgggac gtgcctgctc ccaaagaagt gaagaaagga gaaaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag ctttggccg tacctcccgg    4920 agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc caggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggcttg agaggacttc cggtgcgtta    5340
catgacaaca gcagtcaacg tcacccattc tgggacagaa atcgttgatt tgatgtgcca    5400
tgccactttc acttcacgct actacaaacc catcagagtc cctaattaca atctcaacat    5460
catggatgaa gcccacttca cagacccctc aagtatagct gcaagaggat acatatcaac    5520
aagggttgaa atgggcgagg cggctgccat ttttatgact gccacaccac caggaacccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg aaagcgggt    5760 catacagctc agcaggaaga cttttgagac agaatttcag aaaacaaaaa atcaagagtg    5820 ggacttttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taaggtagcc gccattgagg gagagtttaa    6180
gctgaggaca gagcaaagga gaccttcgt ggaactcatg aagagagggg accttcccgt    6240
```

-continued

```
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca agaattcgc cgctggaaaa agaggagcgg ctttgggagt     6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagactctag agacaattat gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc atacccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcacccag ctgtccaaca     7080
tgcggtaacc acttcataca caactactc cttaatggcg atgccacac aagctggagt      7140
gctgtttggc atgggcaaag ggatgccatt ttatgcatgg gaccttggag tcccgctgct    7200
aatgatgggt tgctattcac aattaacacc cctgactctg atagtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag acccccaggt ggagaagaag atgggacaag tgttactcat    7440
agcagtagca atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag gacatgccgt atcccgggga agtgcaaagc tcagatggtt    7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaccat ggagcgactg caacgtaggc atggggagg      8280
attagtcaga gtgccattgt ctcgcaactc cacacatgag atgtactggg tgtctggggc    8340
aaagagcaac atcataaaaa gtgtgtccac cacaagtcag ctcctcctgg acgcatgga    8400
tggccccagg aggccagtga atatgaggga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggtttct tgatgaaaac cacccataca ggacatgggc    8580
ctaccatggg agctacgaag ccccacgca aggatcagcg tcttccctcg tgaacgggt      8640
```

```
tgttagactc ctgtcaaagc cttgggacgt ggtgactgga gttacaggaa tagccatgac   8700
tgacaccaca ccatacggcc aacaaagagt cttcaaagaa aaagtggaca ccagggtgcc   8760
agatccccaa gaaggcactc gccaggtaat gaacatagtc tcttcctggc tgtggaagga   8820
gctggggaaa cgcaagcggc cacgcgtctg caccaaagaa gagtttatca acaaggtgcg   8880
cagcaatgca gcactgggag caatatttga agaggaaaaa gaatggaaga cggctgtgga   8940
agctgtgaat gatccaaggt tttgggccct agtggatagg gagagagaac accacctgag   9000
aggagagtgt cacagctgtg tgtacaacat gatgggaaaa agagaaaaga agcaaggaga   9060
gttcgggaaa gcaaaaggta gccgcgccat ctggtacatg tggttgggag ccagattctt   9120
ggagtttgaa gcccttggat tcttgaacga ggaccattgg atgggaagag aaaactcagg   9180
aggtggagtc gaagggttag gattgcaaag acttggatac attctagaag aaatgaatcg   9240
ggcaccagga ggaaagatgt acgcagatga cactgctggc tgggacaccc gcattagtaa   9300
gtttgatctg gagaatgaag ctctgattac caaccaaatg gaggaagggc acagaactct   9360
ggcgttggcc gtgattaaat acacatacca aaacaaagtg gtgaaggttc tcagaccagc   9420
tgaaggagga aaaacagtta tggacatcat ttcaagacaa gaccagagag ggagtggaca   9480
agttgtcact tatgctctca acacattcac caacttggtg gtgcagctta tccggaacat   9540
ggaagctgag gaagtgttag agatgcaaga cttatggttg ttgaggaagc cagagaaagt   9600
gaccagatgg ttgcagagca atggatggga tagactcaaa cgaatggcgg tcagtggaga   9660
tgactgcgtt gtgaagccaa tcgatgatag gtttgcacat gccctcaggt tcttgaatga   9720
catgggaaaa gttaggaaag acacacagga gtggaaaccc tcgactggat ggagcaattg   9780
ggaagaagtc ccgttctgct cccaccactt caacaagctg tacctcaagg atgggagatc   9840
cattgtggtc ccttgccgcc accaagatga actgattggc cgagctcgcg tctcaccagg   9900
ggcaggatgg agcatccggg agactgcctg tcttgcaaaa tcatatgcgc agatgtggca   9960
gctcctttat ttccacagaa gggaccttcg actgatggct aatgccattt gctcggctgt  10020
gccagttgac tgggttccaa ctgggagaac cacctggtca atccatggaa agggagaatg  10080
gatgaccact gaggacatgc tcatggtgtg aatagagtg tggattgagg agaacgacca  10140
tatggaggac aagactcctg taacaaaatg gacagacatt ccctatctag gaaaaaggga  10200
ggacttatgg tgtggatccc ttataggca cagaccccgc accacttggg ctgaaaacat  10260
caaagacaca gtcaacatgg tgcgcaggat cataggtgat gaagaaaagt acatggacta  10320
tctatccacc caagtccgct acttgggtga ggaagggtcc acacccggag tgttgtaagc  10380 accaattttta gtgttgtcag gcctgctagt cagccacagt ttggggaaag ctgtgcagcc  10440
tgtaaccccc ccaggagaag ctgggaaacc aagctcatag tcaggccgag aacgccatgg  10500
cacggaagaa gccatgctgc ctgtgagccc ctcagaggac actgagtcaa aaacccac    10560 gcgcttggaa gcgcaggatg ggaaaagaag gtggcgacct tccccacccct tcaatctggg  10620 gcctgaactg gagactagct gtgaatctcc agcagaggga ctagtggtta gaggagaccc  10680
ccccgaaaac gcacaacagc atattgacgc tgggaaagac cagagactcc atgagtttcc  10740
accacgctgg ccgccaggca cagatcgccg aacttcggcg ccggtgtgg ggaaatccat  10800 ggtttct                                                           10807
```

<210> SEQ ID NO 5
<211> LENGTH: 1777
<212> TYPE: DNA

<213> ORGANISM: Artificial Sequence
<220> FEATURE:
<223> OTHER INFORMATION: Synthetic Construct

<400> SEQUENCE: 5

| | | | | | |
|---|---|---|---|---|---|
| agcaaaagca | ggggaaaata | aaagcaacaa | aaatgaaggc | aatactagta | gttctgctat | 60 |
| atacatttgc | aaccgcaaat | gcagacacat | tatgtatagg | ttatcatgcg | aacaattcaa | 120 |
| cagacactgt | agacacagta | ctagaaaaga | atgtaacagt | aacacactct | gttaacctat | 180 |
| tggaggataa | gcataacagt | aagctatgca | aactgagagg | cgtagcacca | ttgcatctag | 240 |
| gtaagtgtaa | tatagccgga | tggattctag | ggaatcccga | atgcgaatca | ctatcaaccg | 300 |
| ctagctcatg | gtcatacata | gtcgaaacac | catcaagcga | taacggtaca | tgttatcccg | 360 |
| gagactttat | cgattacgaa | gagcttagag | agcaattgtc | tagcgtaagc | tcattcgaaa | 420 |
| gattcgaaat | ttttccgaaa | actagctcat | ggcctaatca | cgatagtagt | aaaggcgtaa | 480 |
| ctgccgcatg | cccacacgcc | ggagctaaat | cattctataa | gaatctgatt | tggttagtga | 540 |
| aaaaagagaa | ttcatatccg | aaactatcta | atcatacat | taacgataag | ggtaaggagg | 600 |
| tactagtgtt | gtgggggata | caccatccat | caactagcgc | cgatcagcaa | tcattgtatc | 660 |
| agaacgcaga | cgcatacgta | ttcgtagggt | ctagtagata | ctctaaaaaa | tttaaacccg | 720 |
| aaatcgcaat | tagaccgaaa | gtgagaggcc | aagagggtag | aatgaattac | tattggacac | 780 |
| tagtcgaacc | aggcgataag | attacattcg | aagcgacagg | gaatctagtc | gtaccgagat | 840 |
| acgcattcgc | aatggagaga | aacgccggat | ccggaattat | tattagcgat | acacccgtac | 900 |
| acgattgcaa | tactacgtgt | cagacaccaa | aaggcgcaat | taatactagt | ctgccatttc | 960 |
| agaatataca | cccaattaca | atcggtaagt | gtccaaaata | cgttaagtca | actaagttga | 1020 |
| gactcgcaac | agggttgaga | aatacaccgt | caattcaatc | tagggggttg | ttcggagcaa | 1080 |
| tcgcagggtt | tatcgaaggg | gggtggacag | gtatggttga | cggatggtac | ggataccatc | 1140 |
| atcaaaacga | acagggatcc | ggatacgcag | ccgaactgaa | aagtacacag | aacgctatag | 1200 |
| acgaaattac | gaataaagtg | aatagcgtaa | tcgaaaaaat | gaatacgcaa | tttacagccg | 1260 |
| taggtaagga | gttaatcat | ctcgaaaaaa | ggattgagaa | tctgaataaa | aaagtcgacg | 1320 |
| acggattctt | agacatttgg | acttataacg | ccgaaatgtt | agtgttactc | gaaaacgaaa | 1380 |
| gaacactaga | ctatcacgat | tcaaacgtta | agaatctata | cgaaaaagtg | agatcgcaat | 1440 |
| tgaaaaataa | cgctaaagag | atagggaatg | ggtgtttcga | attctatcat | aaatgcgata | 1500 |
| atacatgtat | ggaatccgtt | aaaaacggaa | catacgatta | ccctaagtat | agcgaagagg | 1560 |
| ctaaactgaa | tagggaagag | atagacggag | tggaacttga | atcaactagg | atttatcaga | 1620 |
| tactcgcaat | ttatagtacg | gttgccagtt | cattggtact | ggtagtctcc | ctgggggcaa | 1680 |
| tcagtttctg | gatgtgctct | aatgggtctc | tacagtgtag | aatatgtatt | taacattagg | 1740 |
| atttcagaag | catgagaaaa | acacccttgt | ttctact | | | 1777 |

<210> SEQ ID NO 6
<211> LENGTH: 1458
<212> TYPE: DNA
<213> ORGANISM: Artificial Sequence
<220> FEATURE:
<223> OTHER INFORMATION: Synthetic Construct

<400> SEQUENCE: 6

| | | | | | |
|---|---|---|---|---|---|
| agcaaaagca | ggggtttaaa | atgaatccaa | accaaaagat | aataaccatt | ggttcggtct | 60 |
| gtatgacaat | tggaatggct | aacttaatat | tacaaattgg | aaacataatc | tcaatatgga | 120 |

-continued

```
ttagccactc aatccaattg gggaatcaga atcaaatcga aacatgcaat caatccgtaa    180
ttacatacga gaataatact tgggtgaatc agacatacgt taacatatcg aatactaatt    240
tcactgccgg acaatccgtc gtgagtgtga aactagccgg taatagtagt ctatgtcccg    300
ttagcggatg ggctatatac tctaaagaca atagcgttag aatcggatct aaaggcgacg    360
tattcgttat acgcgaacca ttcataagtt gtagtccatt agagtgtagg acttttttc    420
tgacacaggg cgcactattg aacgataagc attctaacgg tacaatcaaa gataggtcac    480
catatagaac actaatgtca tgtccgatag gcgaagtgcc tagtccatac aatagtagat    540
tcgaatccgt cgcttggtcc gctagcgcat gccatgacgg tattaattgg ttgacaatcg    600
ggattagcgg acccgataac ggcgcagtcg ccgtacttaa gtataacggt ataattaccg    660
atactattaa gagttggcga aataatatat tgcgaacaca ggaatccgaa tgcgcatgcg    720
ttaacggatc atgtttacc gttatgactg acggaccatc taacgggcaa gcgtcatata    780
agattttag aatcgaaaaa ggtaagatag tgaaatccgt cgaaatgaac gctcctaatt    840
atcattacga agagtgctca tgttatcccg attctagcga aattacatgc gtatgtagag    900
acaattggca cggatctaat agaccttggg tgtcattcaa tcagaatcta gagtatcaaa    960
tcgggtatat atgctcaggg atattcggag acaatcctag acctaacgat aagacagggt   1020
catgcggacc agtgagttct aacggcgcta acgcgttaa ggggtttagt ttcaaatacg   1080
gtaacggcgt atggataggg agaactaagt caatctctag tagaaacgga ttcgaaatga   1140
tatgggaccc taacggatgg accggaaccg ataataattt ttcgattaaa caggatatcg   1200
tagggattaa cgaatggtca gggtatagcg gatcattcgt acagcatcca gagttaaccg   1260
gactcgattg catacgacca tgtttttggg tcgaactgat taggggggaga ccgaaagaga   1320
atactatatg gactagcggg agcagcatat cctttttgtgg tgtaaacagt gacactgtgg   1380
gttggtcttg gccagacggt gctgagttgc catttaccat tgacaagtaa tttgttcaaa   1440
aaactccttg tttctact                                                  1458
```

RECOMBINANT VIRUS WITH CODON-PAIR DEOPTIMIZED REGION AND USES THEREOF FOR THE TREATMENT OF CANCER

CROSS-REFERENCE TO RELATED APPLICATIONS

This application is a National Phase of International Application No. PCT/US2018/067174 filed Dec. 21, 2018, which designated the U.S. and that International Application was published under PCT Article 21 (2) in English, which includes a claim of priority under 35 U.S.C. § 119 (e) to U.S. provisional patent application Nos. 62/609,945, filed Dec. 22, 2017, 62/640,362, filed Mar. 8, 2018, 62/677,132, filed May 28, 2018, and 62/640,355 filed Mar. 8, 2018, the entirety each of which is hereby incorporated by reference.

FIELD OF INVENTION

The present invention relates to modified viruses comprising a modified viral genome containing a plurality of nucleotide substitutions that are used to treat cancer. The nucleotide substitutions result in the exchange of codons for other synonymous codons and/or codon rearrangement and variation of codon pair bias. These modified viruses are used to treat malignant tumors.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Synthetic Virology

Rapid improvements in DNA synthesis technology promise to revolutionize traditional methods employed in virology. One of the approaches traditionally used to eliminate the functions of different regions of the viral genome makes extensive but laborious use of site-directed mutagenesis to explore the impact of small sequence variations in the genomes of virus strains. However, viral genomes, especially of RNA viruses, are relatively short, often less than 10,000 bases long, making them amenable to whole genome synthesis using currently available technology. Recently developed microfluidic chip-based technologies can perform de novo synthesis of new genomes designed to specification for only a few hundred dollars each. This permits the generation of entirely novel coding sequences or the modulation of existing sequences to a degree practically impossible with traditional cloning methods. Such freedom of design provides tremendous power to perform large-scale redesign of DNA/RNA coding sequences to: (1) study the impact of changes in parameters such as codon bias, codon-pair bias, and RNA secondary structure on viral translation and replication efficiency; (2) perform efficient full genome scans for unknown regulatory elements and other signals necessary for successful viral reproduction; (3) develop new biotechnologies for genetic engineering of viral strains and design of anti-viral vaccines; (4) synthesize modified viruses for use in oncolytic therapy.

Reverse Genetics of Poliovirus

Reverse genetics generally refers to experimental approaches to discovering the function of a gene that proceeds in the opposite direction to the so-called forward genetic approaches of classical genetics. That is, whereas forward genetics approaches seek to determine the function of a gene by elucidating the genetic basis of a phenotypic trait, strategies based on reverse genetics begin with an isolated gene and seek to discover its function by investigating the possible phenotypes generated by expression of the wt or mutated gene. As used herein in the context of viral systems, "reverse genetics" systems refer to the availability of techniques that permit genetic manipulation of viral genomes made of RNA. Briefly, the viral genomes are isolated from virions or from infected cells, converted to DNA ("cDNA") by the enzyme reverse transcriptase, possibly modified as desired, and reverted, usually via the RNA intermediate, back into infectious viral particles. This process in picornaviruses is extremely simple; in fact, the first reverse genetics system developed for any animal RNA virus was for PV. Viral reverse genetics systems are based on the historical finding that naked viral genomic RNA is infectious when transfected into a suitable mammalian cell. The discovery of reverse transcriptase and the development of molecular cloning techniques in the 1970's enabled scientists to generate and manipulate cDNA copies of RNA viral genomes. Most commonly, the entire cDNA copy of the genome is cloned immediately downstream of a phage T7 RNA polymerase promoter that allows the in vitro synthesis of genome RNA, which is then transfected into cells for generation of virus. Alternatively, the same DNA plasmid may be transfected into cells expressing the T7 RNA polymerase in the cytoplasm.

De Novo Synthesis of Viral Genomes

Computer-based algorithms are used to design and synthesize viral genomes de novo. These synthesized genomes, exemplified by the synthesis of modified PV described herein, encode exactly the same proteins as wild type (wt) viruses, but by using alternative synonymous codons, various parameters, including codon bias, codon pair bias, RNA secondary structure, and/or dinucleotide content, are altered. The presented data show that these coding-independent changes produce highly modified viruses, often due to poor translation of proteins.

"Modified virus" and "modified viruses", unless indicated otherwise, as used herein refer to virus and viruses in which their genome, in whole or in part, has synonymous codons and/or codon rearrangements and variation of codon pair bias. Modified viruses of the present invention can be used to treat cancer. The recombinant viruses described herein are modified viruses, unless indicated otherwise.

By targeting an elementary function of all viruses, namely protein translation, the inventive methods described herein have been developed for predictably, safely, quickly and cheaply producing modified viruses, which are useful for making oncolytic therapies. Both codon and codon-pair deoptimization in the PV capsid coding region are shown herein to dramatically reduce PV fitness. The present invention is not limited to any particular molecular mechanism underlying virus attenuation via substitution of synonymous codons.

Alternative Encoding

A given peptide can be encoded by a large number of nucleic acid sequences. For example, even a typical short 10-mer oligopeptide can be encoded by approximately $4^{10}$ (about $10^6$) different nucleic acids, and the proteins of PV can be encoded by about $10^{442}$ different nucleic acids. Natural selection has ultimately chosen one of these possible $10^{442}$ nucleic acids as the PV genome. Whereas the primary amino acid sequence is the most important level of information encoded by a given mRNA, there are additional kinds of information within different kinds of RNA sequences. These include RNA structural elements of distinct function (e.g., for PV, the cis-acting replication element, or CRE, translational kinetic signals (pause sites, frame shift sites, etc.), polyadenylation signals, splice signals, enzymatic functions (ribozyme) and, quite likely, other as yet unidentified information and signals).

Even with the caveat that signals such as the CRE must be preserved, $10^{442}$ possible encoding sequences provide tremendous flexibility to make drastic changes in the RNA sequence of polio while preserving the capacity to encode the same protein. Changes can be made in codon bias or codon pair bias, and nucleic acid signals and secondary structures in the RNA can be added or removed. Additional or novel proteins can even be simultaneously encoded in alternative frames.

Codon Pair Bias

A distinct feature of coding sequences is their codon pair bias. This may be illustrated by considering the amino acid pair Ala-Glu, which can be encoded by 8 different codon pairs and this pairing can have a bias that effects translation of human and viral genes in human cells (Table 1). If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation the codon pair GCA-GAA would be expected to occur at a frequency of 0.097 out of all Ala-Glu coding pairs (0.23×0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. This set of genes is the most comprehensive representation of human coding sequences. Using this set of genes, the frequencies of codon usage were re-calculated by dividing the number of occurrences of a codon by the number of all synonymous codons coding for the same amino acid. As expected the frequencies correlated closely with previously published ones such as the ones given in Table 2. Slight frequency variations are possibly due to an oversampling effect in the data provided by the codon usage database at Kazusa DNA Research Institute (http://www.kazusa.or.jp/codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 1 expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.97 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 2; observed frequency). Frequency and observed/expected values for the amino acid pair Ala-Glu, which can be encoded by 8 different codon pairs is seen in Table 1 and the complete set of 3721 ($61^2$) codon pairs, based on the set of 14,795 human genes, (Coleman et al. 2008)

TABLE 1

Codon pair scores for the amino acid pair Alanine-Glutamine

| amino acid pair | codon pair | expected frequency | observed frequency | obs/exp ratio |
|---|---|---|---|---|
| AE | GCAGAA | 0.098 | 0.163 | 1.65 |
| AE | OCAGAO | 0.132 | 0.198 | 1.51 |
| AE | OCCGAA | 0.171 | 0.031 | 0.18 |
| AE | GCCGAG | 0.229 | 0.142 | 0.62 |
| AE | GCOGAA | 0.046 | 0.027 | 0.57 |
| AE | OCGGAO | 0.062 | 0.089 | 1.44 |
| AE | OCTGAA | 0.112 | 0.145 | 1.29 |
| AE | OCTGAG | 0.150 | 0.206 | 1.37 |
| Total | | 1.000 | 1.000 | |

TABLE 2

Codon Bias in Human Genes

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |
| Arg | AGG | 461676.00 | 11.93 | 0.21 |
| Arg | AGA | 466435.00 | 12.06 | 0.21 |
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |

TABLE 2-continued Codon Bias in Human Genes

| Amino Acid | Codon | Number | /1000 | Fraction |
|---|---|---|---|---|
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

If the ratio of observed frequency/expected frequency of the codon pair is greater than one the codon pair is said to be overrepresented. If the ratio is smaller than one, it is said to be underrepresented. In the example the codon pair GCA-GAA is overrepresented 1.65 fold while the coding pair GCC-GAA is more than 5-fold underrepresented.

Many other codon pairs show very strong bias; some pairs are under-represented, while other pairs are over-represented. For instance, the codon pairs GCCGAA (AlaGlu) and GATCTG (AspLeu) are three- to six-fold under-represented (the preferred pairs being GCAGAG and GACCTG, respectively), while the codon pairs GCCAAG (AlaLys) and AATGAA (AsnGlu) are about two-fold over-represented. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

Codon pair bias was discovered in prokaryotic cells, but has since been seen in all other examined species, including humans. The effect has a very high statistical significance, and is certainly not just noise. However, its functional significance, if any, is a mystery. One proposal is that some pairs of tRNAs interact well when they are brought together on the ribosome, while other pairs interact poorly. Since different codons are usually read by different tRNAs, codon pairs might be biased to avoid putting together pairs of incompatible tRNAs. Another idea is that many (but not all) under-represented pairs have a central CG dinucleotide (e.g., GCCGAA, encoding AlaGlu), and the CG dinucleotide is systematically under-represented in mammals. Thus, the effects of codon pair bias could be of two kinds—one an indirect effect of the under-representation of CG in the mammalian genome, and the other having to do with the efficiency, speed and/or accuracy of translation. It is emphasized that the present invention is not limited to any particular molecular mechanism underlying codon pair bias.

Calculation of Codon Pair Bias

Every individual codon pair of the possible 3721 non-"STOP" containing codon pairs (e.g., GTT-GCT) carries an assigned "codon pair score," or "CPS" that is specific for a given "training set" of genes. The CPS of a given codon pair is defined as the log ratio of the observed number of occurrences over the number that would have been expected in this set of genes (in this example the human genome). Determining the actual number of occurrences of a particular codon pair (or in other words the likelihood of a particular amino acid pair being encoded by a particular codon pair) is simply a matter of counting the actual number of occurrences of a codon pair in a particular set of coding sequences. Determining the expected number, however, requires additional calculations. The expected number is calculated so as to be independent of both amino acid frequency and codon bias similarly to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale.

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair. The detailed equations used to calculate CPB are disclosed in WO 2008/121992 and WO 2011/044561, which are incorporated by reference.

$$S(P_{ij}) = \ln\left(\frac{N_o(P_{ij})}{N_E(P_{ij})}\right) = \ln\left(\frac{N_o(P_{ij})}{F(C_i)F(C_j)N_o(X_{ij})}\right)$$

In the calculation, $P_{ij}$ is a codon pair occurring with a frequency of $N_O(P_{ij})$ in its synonymous group. $C_i$ and $C_j$ are the two codons comprising $P_{ij}$, occurring with frequencies $F(C_i)$ and $F(C_j)$ in their synonymous groups respectively. More explicitly, $F(C_i)$ is the frequency that corresponding amino acid $X_i$ is coded by codon $C_i$ throughout all coding regions and $F(C_i)=N_O(C_j)/N_O(X_i)$, where $N_O(C_i)$ and $N_O(X_i)$ are the observed number of occurrences of codon $C_i$ and amino acid $X_i$ respectively. $F(C_j)$ is calculated accordingly. Further, $N_O(X_{ij})$ is the number of occurrences of amino acid pair $X_{ij}$ throughout all coding regions. The codon pair bias score $S(P_{ij})$ of $P_{ij}$ was calculated as the log-odds ratio of the observed frequency $N_o(P_{ij})$ over the expected number of occurrences of $N_e(P_{ij})$.

Using the formula above, it was then determined whether individual codon pairs in individual coding sequences are over- or under-represented when compared to the corresponding genomic $N_e(P_{ij})$ values that were calculated by using the entire human CCDS data set. This calculation resulted in positive $S(P_{ij})$ score values for over-represented and negative values for under-represented codon pairs in the human coding regions.

The "combined" codon pair bias of an individual coding sequence was calculated by averaging all codon pair scores according to the following formula:

$$S(P_{ij}) = \sum_{l=1}^{k} \frac{S(P_{ij})l}{k-1}$$

The codon pair bias of an entire coding region is thus calculated by adding all of the individual codon pair scores comprising the region and dividing this sum by the length of the coding sequence.

Calculation of Codon Pair Bias, Implementation of Algorithm to Alter Codon-Pair Bias.

An algorithm was developed to quantify codon pair bias. Every possible individual codon pair was given a "codon pair score", or "CPS". CPS is defined as the natural log of the ratio of the observed over the expected number of occurrences of each codon pair over all human coding regions, where humans represent the host species of the instant vaccine virus to be recoded.

$$CPS = \ln\left(\frac{F(AB)_o}{\frac{F(A) \times F(B)}{F(X) \times F(Y)} \times F(XY)}\right)$$

Although the calculation of the observed occurrences of a particular codon pair is straightforward (the actual count within the gene set), the expected number of occurrences of a codon pair requires additional calculation. We calculate this expected number to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome Using these calculated CPSs, any coding region can then be rated as using over- or under-represented codon pairs by taking the average of the codon pair scores, thus giving a Codon Pair Bias (CPB) for the entire gene.

$$CPB = \sum_{i=1}^{k}\frac{CPSi}{k-1}$$

As discussed further below, codon pair bias takes into account the score for each codon pair in a coding sequence averaged over the entire length of the coding sequence. According to the invention, codon pair bias is determined by $$CPB = \sum\nolimits_{i=1}^{k}\frac{CSPi}{K-1}$$

Accordingly, similar codon pair bias for a coding sequence can be obtained, for example, by minimized codon pair scores over a subsequence or moderately diminished codon pair scores over the full length of the coding sequence.

Since all 61 sense codons and all sense codon pairs can certainly be used, it would not be expected that substituting a single rare codon for a frequent codon, or a rare codon pair for a frequent codon pair, would have much effect. Irrespective of the precise mechanism, the data indicate that the large-scale substitution of synonymous deoptimized codons into a viral genome results in severely attenuated viruses. This procedure for producing modified viruses has been dubbed SAVE (Synthetic Attenuated Virus Engineering).

According to aspects of the invention, viral modification can be accomplished by changes in codon pair bias as well as codon bias in one or more portions of the virus's genome. However, it is expected that adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties. The work disclosed herein includes modified codon pair bias-reduced or -minimized sequences in which codons are shuffled, but the codon usage profile is unchanged.

It has been known that malignant tumors result from the uncontrolled growth of cells in an organ. The tumors grow to an extent where normal organ function may be critically impaired by tumor invasion, replacement of functioning tissue, competition for essential resources and, frequently, metastatic spread to secondary sites. Malignant cancer is the second leading cause of mortality in the United States.

Up to the present, the methods for treating malignant tumors include surgical resection, radiation and/or chemotherapy. However, numerous malignancies respond poorly to all traditionally available treatment options and there are serious adverse side effects to the known and practiced methods. There has been much advancement to reduce the severity of the side effects while increasing the efficiency of commonly practiced treatment regimens. However, many problems remain, and there is a need to search for alternative modalities of treatment. The search is particularly urgent for primary malignant tumors of the central nervous system. Brain tumors, especially glioblastomas, remain one of the most difficult therapeutic challenges. Despite the application of surgery, radiotherapy and chemotherapy, alone and in combination, glioblastomas are almost always fatal, with a median survival rate of less than a year and 5-year survival rates of 5.5% or less. None of the available therapeutic modes has substantially changed the relentless progress of glioblastomas.

Systematic studies of patients who were diagnosed with malignant glioma and underwent surgery to wholly or partially remove the tumor with subsequent chemotherapy and/or radiation showed that the survival rate after 1 year remains very low, particularly for patients who are over 60 years of age. Malignant gliomas have proven to be relatively resistant to radiation and chemotherapeutic regimens. Adding to the poor prognosis for malignant gliomas is the frequent tendency for local recurrence after surgical ablation and adjunct radiation/chemotherapy.

In recent years, there have been proposals to use viruses for the treatment of cancer: (1) as gene delivery vehicles; (2) as direct oncolytic agents by using viruses that have been genetically modified to lose their pathogenic features; or (3) as agents to selectively damage malignant cells using viruses which have been genetic engineered for this purpose.

Examples for the use of viruses against malignant gliomas include the following. Herpes Simplex Virus dlsptk (HSVdlsptk), is a thymidine kinase (TK)-negative mutant of HSV. This virus is attenuated for neurovirulence because of a 360-base-pair deletion in the TK gene, the product of which is necessary for normal viral replication. It has been found that HSVdlsptk retains propagation potential in rapidly dividing malignant cells, causing cell lysis and death. Unfortunately, all defective herpes viruses with attenuated neuropathogenicity have been linked with serious symptoms of encephalitis in experimental animals. For example, in mice infected intracerebrally with HSVdlsptk, the $LD_{50}^{Ic}$ (intracranial administration) is $10^6$ pfu, a rather low dose. This limits the use of this mutant HSV. Other mutants of HSV have been proposed and tested. Nevertheless, death from viral encephalitis remains a problem.

Another proposal was to use retroviruses engineered to contain the HSV tk gene to express thymidine kinase which causes in vivo phosphorylation of nucleoside analogs, such as gancyclovir or acyclovir, blocking the replication of DNA and selectively killing the dividing cell. Izquierdo, M., et al., *Gene Therapy*, 2:66-69 (1995) reported the use of Moloney Murine Leukemia Virus (MoMLV) engineered with an insertion of the HSV tk gene with its own promoter. Follow-up of patients with glioblastomas that were treated with intraneoplastic inoculations of therapeutic retroviruses by MRI revealed shrinkage of tumors with no apparent short-term side effects. However, the experimental therapy had no effect on short-term or long-term survival of affected patients. Retroviral therapy is typically associated with the danger of serious long-term side effects (e.g., insertional mutagenesis).

Similar systems have been developed to target malignancies of the upper airways, tumors that originate within the tissue naturally susceptible to adenovirus infection and that are easy accessible. However, Glioblastoma multiforme, highly malignant tumors composed out of widely heterogeneous cell types (hence the denomination multiforme) are characterized by exceedingly variable genotypes and are unlikely to respond to oncolytic virus systems directed against homogeneous tumors with uniform genetic abnormalities.

The effects of our virus modification can be confirmed in ways that are well known to one of ordinary skill in the art. Non-limiting examples induce plaque assays, growth measurements, reverse genetics of RNA viruses, and reduced lethality in test animals. The instant application demonstrates that the modified viruses are capable of inducing protective immune responses in a host.

SUMMARY OF THE INVENTION

The following embodiments and aspects thereof are described and illustrated in conjunction with compositions and methods which are meant to be exemplary and illustrative, not limiting in scope.

It is an objective of the present invention to develop modified viruses for the treatment for various types of cancer.

It is a further objective of the present invention to develop modified viruses for the treatment for various types of cancer that can be used in combination with anti-PDL-1 antibody therapeutics or other immune-oncology therapies.

It is a further objective of the present invention to treat cancer cells by infecting them with modified viruses to cause cancer cell lysis and death.

It is a further objective of the present invention to treat cancer cells by infecting them with modified viruses and thereby elicit an anti-tumor immune response.

It is a further objective of the present invention to treat cancer cells by infecting them with modified viruses and thereby elicit an anti-tumor immune response by increasing or decreasing the expression of anti-tumor immune proteins such as PD-1, CTLA-4, IDO1, TIM3, lag-3.

It is a further objective of the present invention to treat cancer cells by infecting them with modified viruses and thereby elicit an innate immune response in the tumor cells via the activation of innate signaling receptors RIG-I, STNG, and innate immunity transcription factors IRF3, IRF7, or NFkB in tumors.

It is a further objective of the present invention to treat cancer cells by infecting them with modified viruses and thereby elicit an innate immune response in the tumor.

It is a further objective of the present invention to treat cancer cells by infecting them with modified viruses and thereby eliciting a pro-inflammatory immune response in the tumor.

It is a further objective of the present invention to treat cancer cells by infecting them with modified viruses and thereby recruiting pro-inflammatory white-blood cells to the tumor.

It is a further objective of the present invention to treat cancer cells by infecting them with modified viruses and thereby decreasing regulatory white-blood cells from the tumor.

It is a further objective of the present invention to pre-treat the recipient with a modified virus to elicit an immune response before administering the virus to treat the cancer.

It is a further objective of the present invention to pre-treat the recipient with a modified virus to elicit an immune response before administering a natural isolate of the virus to treat the cancer It is a further objective of the present invention to develop novel wild-type virus modified virus chimera, which would be suitable for the treatment and cure of gliomas, in particular glioblastomas.

It is a further objective of the present invention to develop a novel modified virus, which would be suitable for the treatment of adenocarcinomas, and in particular, cervical cancer.

It is a further objective of the present invention to develop a novel modified virus, which would be suitable for the treatment of breast cancer.

It is a further objective of the present invention to develop novel modified virus, which would be suitable for the treatment of cancer cells that are positive for keratin by immunoperoxidase staining.

It is a further objective of the present invention to develop further novel modified virus, which would be suitable for the treatment of cancer cells where p53 gene expression is reported to be low or absent.

It is a further objective of the present invention to develop further novel modified virus, which would be suitable for the treatment of tumors where the cells are hypodiploid.

It is a further objective of the present invention to develop a novel modified virus, which is suitable for the treatment of lung carcinomas, and in particular, lung cancer.

It is a further objective of the present invention to develop a novel modified virus, which is suitable for the treatment of cancer that are hypotriploid (e.g., 64, 65, or 66 chromosome count in about 40% of cells).

It is a further objective of the present invention to develop a novel modified virus, which is suitable for the treatment of cancer that are have had single copies of Chromosomes N2 and N6 per cell.

It is a further objective of the present invention to develop a novel modified virus, which is suitable for the treatment of cancer that express the isoenzyme G6PD-B of the enzyme of the enzyme glucose-6-phosphate dehydrogenase (G6PD).

It is a further objective of the present invention to develop a novel modified virus, which is suitable for the treatment of melanoma.

It is a further objective of the present invention to develop a novel modified virus, which is suitable for the treatment of malignant cells derived from melanocytes.

It is a further objective of the present invention to develop a novel modified virus, which is suitable for the treatment of neuroblastoma.

It is a further objective of the present invention to develop a novel modified virus, which is suitable for the treatment of cancer that has MYCN oncogene amplification of at least 3-fold.

It is a further objective of the present invention to develop a modified virus, which is suitable for the treatment of breast cancer.

It is a further objective of the present invention to develop a modified virus, which is suitable for the treatment of bladder cancer.

It is a further objective of the present invention to develop a modified virus, which is suitable for the treatment of colon cancer.

It is a further objective of the present invention to develop a modified virus, which is suitable for the treatment of prostate cancer.

It is a further objective of the present invention to develop a modified virus, which is suitable for the treatment of peripheral nerve sheath tumors The present invention provides a modified virus that comprises a modified viral genome containing nucleotide substitutions engineered in one or more (e.g., 1, 2, 4, 5, 6, 7, 8, 9, 10, 15, 20, 25, 30, 40, 50, or more) locations in the genome, wherein the substitutions introduce a plurality of synonymous codons into the genome. This substitution of synonymous codons alters various parameters, including codon bias, codon pair bias, density of deoptimized codons and deoptimized codon pairs, RNA secondary structure, CpG dinucleotide content, C+G content, UpA dinucleotide content, translation frameshift sites, translation pause sites, the presence or absence of tissue specific microRNA recognition sequences, or any combination thereof, in the genome. Because of the large number of defects involved, the modified virus of the invention provides a way of producing stably modified oncolytic virus against a variety of different tumor types.

In one embodiment, a modified virus is provided which comprises a nucleic acid sequence encoding a viral protein or a portion thereof that is identical to the corresponding sequence of a parent virus, wherein the nucleotide sequence of the modified virus contains the codons of a parent sequence from which it is derived, and wherein the nucleotide sequence is less than 98% identical to the nucleotide sequence of the parent virus. In another embodiment, the nucleotide sequence is less than 90% identical to the sequence of the parent virus. The substituted nucleotide sequence which provides for modification is at least 100 nucleotides in length, or at least 250 nucleotides in length, or at least 500 nucleotides in length, or at least 1000 nucleotides in length. The codon pair bias of the modified sequence is less than the codon pair bias of the parent virus, and is reduced by at least about 0.05, or at least about 0.1, or at least about 0.2.

In one embodiment, a modified virus is provided which comprises a nucleic acid sequence encoding a viral protein or a portion thereof that is similar to the corresponding sequence of a parent virus, wherein the nucleotide sequence of the modified virus contains the nucleotide sequence is less than 98% identical to the nucleotide sequence of the parent virus. In another embodiment, the nucleotide sequence is less than 90% identical to the sequence of the parent virus. The substituted nucleotide sequence which provides for modification is at least 100 nucleotides in length, or at least 250 nucleotides in length, or at least 500 nucleotides in length, or at least 1000 nucleotides in length. The CpG di-nucleotide content of the modified sequence is increased by at least 19 over the parent virus, or by at least 41.

In one embodiment, a modified virus is provided which comprises a nucleic acid sequence encoding a viral protein or a portion thereof that is similar to the corresponding sequence of a parent virus, wherein the nucleotide sequence of the modified virus contains the nucleotide sequence is less than 98% identical to the nucleotide sequence of the parent virus. In another embodiment, the nucleotide sequence is less than 90% identical to the sequence of the parent virus. The substituted nucleotide sequence which provides for modification is at least 100 nucleotides in length, or at least 250 nucleotides in length, or at least 500 nucleotides in length, or at least 1000 nucleotides in length. The UpA di-nucleotide content of the modified sequence is increased by at least 13 over the parent virus, or by at least about 26 over the parent virus.

Embodiments of the present invention also provides a therapeutic composition for treating in a subject comprising the modified virus and a pharmaceutically acceptable carrier. This invention also provides a therapeutic composition for eliciting an immune response in a subject having cancer, comprising the modified virus and a pharmaceutically acceptable carrier. The invention further provides a modified host cell line specially engineered to be permissive for a modified virus that is inviable in a wild type host cell.

According to the invention, modified viruses are made by transfecting modified viral genomes into host cells, whereby modified virus particles are produced. The invention further provides pharmaceutical compositions comprising modified virus which are suitable for treatment of cancer.

Various embodiments of the present invention provide for a method of treating a malignant tumor, comprising: administering a modified virus to a subject in need thereof, wherein the modified virus is selected from the group consisting of: a modified virus derived from a wild-type virus or a previously modified virus, by substituting at least one genomic region of the wild-type virus with a codon-pair deoptimized region encoding a similar protein sequence, wherein the codon pair bias of the modified sequence is less than the codon pair bias of the parent virus, and is reduced by at least about 0.05, or at least about 0.1, or at least about 0.2, a modified virus derived from a wild-type virus or a previously modified virus, by substituting at least one genomic region of the wild-type virus with a region with increased CpG di-nucleotide encoding a similar protein sequence, wherein in the increase of the CpG di-nucleotide is at least 41 instances above the parent, or at least 21 instances above the parent viral genome, a modified virus derived from a wild-type virus or a previously modified virus, by substituting at least one genomic region of the wild-type virus with a region with increased UpA di-nucleotide encoding a similar protein sequence, wherein in the increase of the UpA di-nucleotide is at least 26 instances above the parent, or at least 13 instances above the parent viral genome, a modified virus derived from a wild-type virus or a previously modified virus, by substituting at least one genomic region of the wild-type virus with a region with increased UpA and the CpG di-nucleotide encoding a similar protein sequence, wherein in the increase of the UpA and the CpG di-nucleotide was at least 42 instances combined above the parent, and combinations thereof.

Various embodiments of the present invention provide for a method of treating a malignant tumor, comprising: administering a prime dose of a modified virus to a subject in need thereof; and administering one or more boost dose of a modified virus to the subject in need thereof, wherein the prime dose and boost dose of the modified virus are each independently selected from the group consisting of: an attenuated virus produced by a method other than codon-pair deoptimization, a modified virus derived from a wild-type virus or a previously modified virus, by substituting at least one genomic region of the wild-type virus with a codon-pair deoptimized region encoding a similar protein sequence, wherein the codon pair bias of the modified sequence is less than the codon pair bias of the parent virus, and is reduced by at least about 0.05, or at least about 0.1, or at least about 0.2, a modified virus derived from a wild-type virus or a previously modified virus, by substituting at least one genomic region of the wild-type virus with a region with increased CpG di-nucleotide encoding a similar protein sequence, wherein in the increase of the CpG di-nucleotide is at least 41 instances above the parent, or at least 21 instances above the parent viral genome, a modified virus derived from a wild-type virus or a previously modified virus, by substituting at least one genomic region of the wild-type virus with a region with increased UpA di-nucleotide encoding a similar protein sequence, wherein in the increase of the UpA di-nucleotide is at least 26 instances above the parent, or at least 13 instances above the parent viral genome, a modified virus derived from a wild-type virus or a previously modified virus, by substituting at least one genomic region of the wild-type virus with a region with increased UpA and the CpG di-nucleotide encoding a similar protein sequence, wherein in the increase of the UpA and the CpG di-nucleotide was at least 42 instances combined above the parent, and combinations thereof.

In various embodiments, the prime dose can be administered subcutaneously, intramuscularly, intradermally, intranasally, or intravenously. In various embodiments, the one or more boost dose can be administered intratumorally or intravenously.

In various embodiments, a first of the one or more boost dose can be administered about 2 weeks after one prime dose, or if more than one prime dose then about 2 weeks after the last prime dose.

In various embodiments, the subject can have cancer. In various embodiments, the subject can be at a higher risk of developing cancer.

In various embodiments, the prime dose can be administered when the subject does not have cancer.

In various embodiments, the one or more boost dose can be administered about every 1, 2, 3, 4, 5, 6, 7, 8, 9 or 10 years after the prime dose when the subject does not have cancer. In various embodiments, the one or more boost dose can be administered after the subject is diagnosed with cancer.

In various embodiments, the method can further comprise administering a PD-1 inhibitor or a PD-L1 inhibitor.

In various embodiments, the PD-1 inhibitor can be an anti-PD1 antibody. In various embodiments, the anti-PD1 antibody can be selected from the group consisting of pembrolizumab, nivolumab, pidilizumab, AMP-224, AMP-514, spartalizumab, cemiplimab, AK105, BCD-100, BI 754091, JS001, LZM009, MGA012, Sym021, TSR-042, MGD013, AK104, XmAb20717, tislelizumab, and combinations thereof.

In various embodiments, the PD-1 inhibitor can be selected from the group consisting of PF-06801591, anti-PD1 antibody expressing pluripotent killer T lymphocytes (PIK-PD-1), autologous anti-EGFRvIII 4SCAR-IgT cells, and combinations thereof.

In various embodiments, the PD-L1 inhibitor can be an anti-PD-L1 antibody. In various embodiments, the anti-PD-L1 antibody can be selected from the group consisting of BGB-A333, CK-301, FAZ053, KN035, MDX-1105, MSB2311, SHR-1316, atezolizumab, avelumab, durvalumab, BMS-936559, CK-301, and combinations thereof.

In various embodiments, the anti-PD-L1 inhibitor is M7824.

In various embodiments, treating the malignant tumor can decrease the likelihood of recurrence of the malignant tumor. In various embodiments, treating the malignant tumor can decrease the likelihood of having a second cancer that is different from the malignant tumor.

In various embodiments, if the subject develops a second cancer that is different from the malignant tumor, the treatment of the malignant tumor can result in slowing the growth of the second cancer.

In various embodiments, wherein after remission of the malignant tumor, if the subject develops a second cancer that is different from the malignant tumor, the treatment of the malignant tumor can result in slowing the growth of the second cancer.

In various embodiments, treating the malignant tumor can stimulate an inflammatory immune response in the tumor. In various embodiments, treating the malignant tumor can recruit pro-inflammatory cells to the tumor. In various embodiments, treating the malignant tumor can stimulate an anti-tumor immune response.

Various embodiments of the present invention provide for a method of treating the malignant tumor of the present invention, wherein the modified virus can be a recombinant modified virus.

Various embodiments of the present invention provide for a method of treating the malignant tumor of the present invention wherein modified virus can be modified from a picornavirus.

In various embodiments, the picornavirus is an enterovirus. In various embodiments, the enterovirus is enterovirus C. In various embodiments, the enterovirus C is poliovirus.

Various embodiments of the present invention provide for a method of treating the malignant tumor of the present invention wherein modified virus can be modified from orthomyxovirus. In various embodiments, the orthomyxovirus can be an Influenza A virus. In various embodiments, one or more segments of the influenza A Virus can be recoded. In various embodiments, the HA, NA or both HA and NA regions are recoded (e.g., deoptimized).

In various embodiments, the modified virus can be SEQ ID NO:5 or SEQ ID NO:6.

Various embodiments of the present invention provide for a method of treating the malignant tumor of the present invention, wherein the modified virus can be modified from flavivirus.

In various embodiments, the flavivirus can be a Zika virus.

In various embodiments, a pre-membrane/Envelope (E) encoding region, or a nonstructural protein 3 (NS3) encoding region, or both of the Zika virus can be recoded. In various embodiments, recoding can comprise altering the frequency of CG and/or TA dinucleotides in the E and NS3 coding sequences. In various embodiments, the recoded E protein-encoding sequence, or the NS3 coding sequence, or both can have a codon pair bias of less than −0.1. In various embodiments, the recoded E protein-encoding sequence, or the NS3 coding sequence, or both can have a codon pair bias reduction of 0.1-0.4.

In various embodiments, the modified virus can be SEQ ID NO:2, SEQ ID NO:3 or SEQ ID NO:4.

Various embodiments of the present invention provide for a method of treating the malignant tumor of the present invention, wherein the malignant tumor can be a solid tumor.

Various embodiments of the present invention provide for a method of treating the malignant tumor of the present invention, wherein the malignant tumor can be glioblastoma, adenocarcinoma, melanoma, lung carcinoma, neuroblastoma breast cancer, bladder cancer, colon cancer, prostate cancer, or liver cancer.

Various embodiments of the present invention provide for a method of treating the malignant tumor of the present invention, wherein the modified virus can be administered intratumorally, intravenously, intracerebrally, intramuscularly, intraspinally or intrathecally.

Various embodiments of the present invention provide for a method of treating the malignant tumor of the present invention, wherein the modified virus can be PV1-MinY and is prepared from the wild-type virus or the previously modified virus, wherein the middle portion of the P1 region thereof is substituted with a synthetic sequence recoded for reduced codon pair score according to human codon pair bias.

Various embodiments of the present invention provide for a method of treating the malignant tumor of the present invention, wherein the recombinant modified virus can be PV1-MinY and is prepared from the previously modified virus PV1(M) or wild-type virus PV1(M) and the middle portion of the P1 region thereof substituted with a synthetic sequence recoded for increased UpA and or CpG di-nucleotides.

In various embodiments, the recombinant virus can be PV1-MinY prepared from PV1(M) and in which a fragment of nucleotides comprising nucleotide position 1513 to nucleotide position 2470 of the P1 region is substituted with corresponding fragment of nucleotides comprising nucleotide position 1513 to nucleotide position 2470 of the P1 region recoded for reduced codon pair score according to human codon pair bias.

Various embodiments of the present invention provide for a method of treating the malignant tumor of the present invention, wherein the modified virus is PV1-MinY prepared from PV1(M) and in which a fragment of nucleotides consisting of nucleotide position 1513 to nucleotide position 2470 of the P1 region is substituted with corresponding fragment of nucleotides comprising nucleotide position 1513 to nucleotide position 2470 of the P1 region recoded for reduced codon pair score according to human codon pair bias.

Various embodiments of the present invention provide for a method of treating a malignant tumor, comprising: preparing a recombinant modified picornavirus from a wild-type picornavirus by substituting at least a fragment of the nucleotides in the P1 domain of the wild-type picornavirus with the corresponding fragment of nucleotides comprising a synthetic, sequence recoded for reduced codon pair score according to human codon pair bias, and optionally, substituting P1 of the wild-type picornavirus with a synthetic P1 recoded for reduced codon pair score according to human codon pair bias, selected from the group consisting of PV1(S), PV2(S) and PV3(S); and administering the recombinant modified virus to a subject in need thereof.

In various embodiments, substituting at least a fragment of the nucleotides can comprise substituting at least a fragment of the nucleotides comprising nt #1513-nt #2470 of SEQ ID NO:1, which is the P1 domain of the modified virus, with the corresponding fragment of nucleotides comprising a synthetic sequence recoded for reduced codon pair score according to human codon pair bias.

In various embodiments, the recombinant virus can be intratumorally, intravenously, intracerebrally, intramuscularly, intraspinally or intrathecally administered and causes cell lysis in the tumor cells.

In various embodiments, the malignant tumor can be selected from a group consisting of glioblastoma multiforme, medulloblastoma, mammary carcinoma, prostate carcinoma, colorectal carcinoma, hepatocellular carcinoma, bronchial carcinoma, and epidermoid carcinoma.

In various embodiments, the picornavirus can be of the species enterovirus C. In various embodiments, the picornavirus can be a poliovirus.

In various embodiments, the P1 domain can be chosen from the Sabin vaccine strains PV1(S), PV2(S) and PV3(S).

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 2 depicts the viability of constructed PV-Min subclones. (Top) The poliovirus genome, which is translated as a single open reading frame. (Bottom) The cDNA of the various chimeric synthetic poliovirus constructs that were constructed via molecular cloning, and their viability in cultured HeLa R19 cells. A virus was obtained containing at least one segment of PV-Min, thus no gross defects were located in any one synthetic region (X, Y, or Z). Nucleotide positions which separate the regions are shown. The first 12 nucleotides (4 codons) in all reading frames are PV(M)-wt sequence to allow proper initiation of translation. Corresponding colors to sequence: Black: PV(M)-wt; Gray: PV-Min; Thatched: PV-Max FIG. 3 depicts growth titer of synthetic viruses constructed. After the transfection of transcript RNA from all viable viral constructs (FIG. 4), viruses were amplified via two subsequent passages in HeLa R19 cells. Then the titer to which these viruses grew was measured via plaque assay on HeLa R19 cell monolayers. PV-Max and PV(M)-wt viruses grew to a similar titer ($\sim 10^9$), whereas PV-Min chimera viruses yielded lower PFU/ml titers, with an apparent step-wise decrease in titer. The addition of PV-Min sequence to the P1 region decreased the PFU titer. The graph displays the average titer of three independent experiments with error bars indicating standard deviation values.

FIGS. 4A-4B depict the effect of altered codon-pair bias on translation. (FIG. 4A) Structure of a dicistronic reporter. The first cistron uses the hepatitis C virus (HCV) Internal Ribosome Entry Site (IRES) to initiate translation of *Renilla* luciferase (R-Luc). This first cistron provides an internal control to normalize for the amount of input RNA. The second cistron uses the poliovirus IRES to initiate translation of Firefly luciferase (F-Luc). The region labeled "P1"

was replaced by synthetic P1 regions of the CPB-altered viruses. From these constructs (+)RNA was transcribed. (FIG. 4B) Each dicistronic RNA was transfected, in the presence of 2 mM GuHCl, into HeLa R19 cells. After 6 hours, the R-Luc and F-Luc activity was measured. The F-Luc/R-Luc ratio values were normalized to the F-Luc/R-Luc ratio for the PV(M)-wt P1 region, which was set to 100%. The graph displays the average of three independent experiments with error bars indicating standard deviation values. The P1s utilizing under-represented codon-pairs (PV-Min, PV-MinZ, and PV-MinXY) had a decreased rate of translation, whereas the P1 containing over-represented codon-pairs (PV-Max) appeared to have a slight increase in its translation efficiency.

FIG. 8A-8B describes the rapid construction of six SAVE-deoptimized, live-attenuated Zika virus vaccine candidates in less than 1 month with growth in Vero cells under animal component-free conditions. (FIG. 8A) Codon pair bias of the Zika prM/E and NS3 genes and their SAVE-deoptimized counterparts in relation to the human ORFeome. Codon-Pair Bias (CPB) is expressed as the average codon pair score of a given gene's open reading frame (ORF). Positive and negative CPB value signifies the predominance of statistically over- or under-represented codon-pairs, respectively in an ORF. Red circles indicate the CPB of each of the 14,795 human ORFs, representing the majority of the known, annotated human genes at the time of our analysis (ORFeome). The CPB of wild-type prM/E and NS3 genes fall within the normal range of human host cell's genes. Following codon pair-'deoptimization' via SAVE, the resulting deoptimized prM/E and NS3 gene segments were now encoded predominately by under-represented human codon-pairs as evident by their extremely negative CPB, and are drastically different from any human gene. (FIG. 8B) cDNA genomes of wild-type and synthetically 'de-optimized' chimeric Zika vaccine variants. The SAVE-deoptimized synthetic prM/E and NS3 from FIG. 8A were synthesized de novo and using overlapping PCR subcloned individually into the WT PRVABC59 (PR15) or MR766 genomes—yielding six independent cDNA genomes each containing a synthetically 'de-optimized' fragment(s). We constructed infectious cDNA genomes for wt PR15 and MR766 in 7 days and then recovered fully infectious, replicating virus for the six deoptimized ZIKV vaccine candidates in 27 days via transfection of RNA into BHK cells.

FIG. 10 describes a reduction of protein and RNA expression in ZIKV infected cells. Western blot was used to measure envelope glycoprotein expression in Vero cells infected by E-Min (min) and wildtype (WT) variants of ZIKV strains PRVABC59 (PR15) and MR766 after being incubated for 24 hours at 33° C. In both strains of ZIKV, envelope glycoprotein expression was greatly reduced for the E-Min variants.

FIG. 11 describes virus phenotypes in infected mice. Attenuation of SAVE ZIKV vaccine candidates in AG129 mice. AG129 mice were injected with either: i) synthetically derived wild-type virus MR766 and PR15 virus at a dose of $10^2$ (positive control); ii) either a dose of $10^4$ or $10^2$ PFU of the vaccine candidates PR15 E-Min or MR766 E-Min and NS3-Min; iii) a single dose of $10^4$ of the vaccine candidate PR15 NS3+E-Min; all delivered in 100 µL subcutaneously. Injected mice were examined for mortality and morbidity (weight loss). All mice inoculated with $10^2$ wt virus and 80% of mice inoculated with $10^4$ MR766 N53-Min succumbed to infection. All other mice survived including all mice vaccinated with $10^4$ PFU of the lead candidate MR766 E-Min and none exhibited any weight loss.

FIG. 14 describes the experimental outline for testing the oncolytic properties of MR766 E-W/W/Min Zika virus using an in vivo tumor model of CCL53.1 murine epithelial melanoma cells implanted into immune-competent DBA/2 mice. Mice were vaccinated 5 times on Day 0, Day 14, Day 26, Day 71, and Day 85 with MR766 E-W/W/Min. CCL53.1 cells were implanted into vaccinated or mock-vaccinated mice on Day 97, 11 days after the final vaccination. Implantation was done by injecting $1\times10^6$ CCL53.1 cells subcutaneously into the lower right flank in all animals. Some also were injected subcutaneously into the lower left flank with $2.5\times10^5$ CCL53.1 cells. Implanted mice were treated with $1\times10^7$ PFU MR766 E-W/W/Min or mock treated by injection with OptiPro SFM directly into the right flank tumor only on Day 103, 10 days after tumor implantation. Treatments were only performed on the right flank tumor to observe immune-mediated oncolysis of the uninjected tumor. The same treatments were repeated twice more on Day 105 (12 days after tumor implantation) and Day 107 (14 days after tumor implantation). Mice were monitored for weight and tumor size measurement daily for 10 days post treatment (Days 107-117), and every other day until 20 days post treatment (118-127).

FIG. 15 describes the reduction of tumor size in mice treated 3 times with MR766 E-W/W/Min injected by the intratumoral route in DBA/2 mice implanted with CCL53.1 murine epithelial melanoma cells. Tumors shrunk significantly in treated animals by day 5 while in mock treated DBA/2 mice there was no improvement and increased tumor size.

Figure 16:
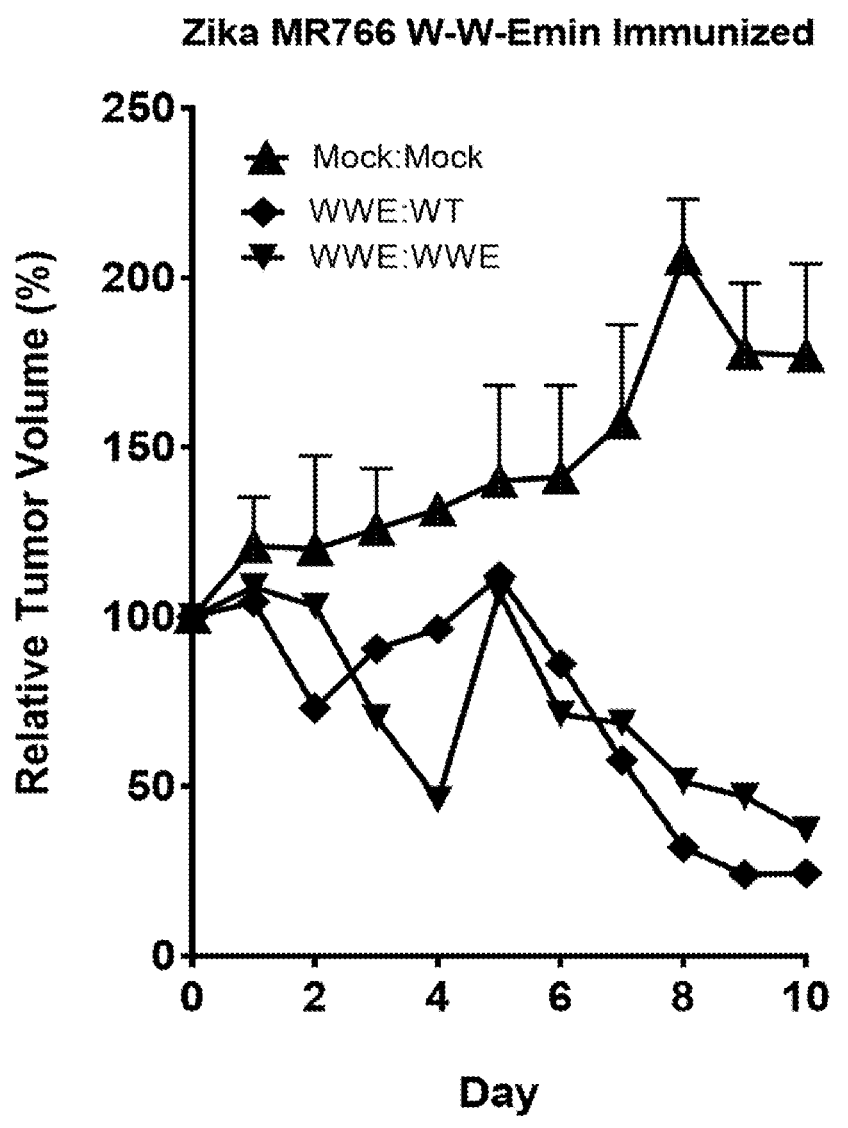

FIG. 16 describes the effects of prior immunization with Zika virus MR766 W-E-W/W/Min on tumor size in DBA/2 mice implanted with CCL53.1 murine epithelial melanoma cells. Mice were vaccinated 5 times on Day 0, Day 14, Day 26, Day 71, and Day 85 with MR766 E-W/W/Min or mock vaccinated with OptiPro medium. CCL53.1 cells were implanted into vaccinated or mock-vaccinated mice by injecting $1\times10^6$ CCL53.1 cells subcutaneously into the lower right flank in all animals. Implanted mice were treated with $1\times10^7$ PFU MR766 E-W/W/Min, $1\times10^7$ PFU MR766 WT, or mock treated by injection directly into the right flank tumor. Treatments were performed three times every two days and tumor size was measured daily through day 10 post-treatment. Mock immunized: mock treated DBA/2 mouse tumors increased steadily through day 10, however, MR766 WT and MR766 E-W/W/Min treatment was effective in reducing average tumor volume in mice that were previously immunized with MR766 E-W/W/Min.

Figure 17:
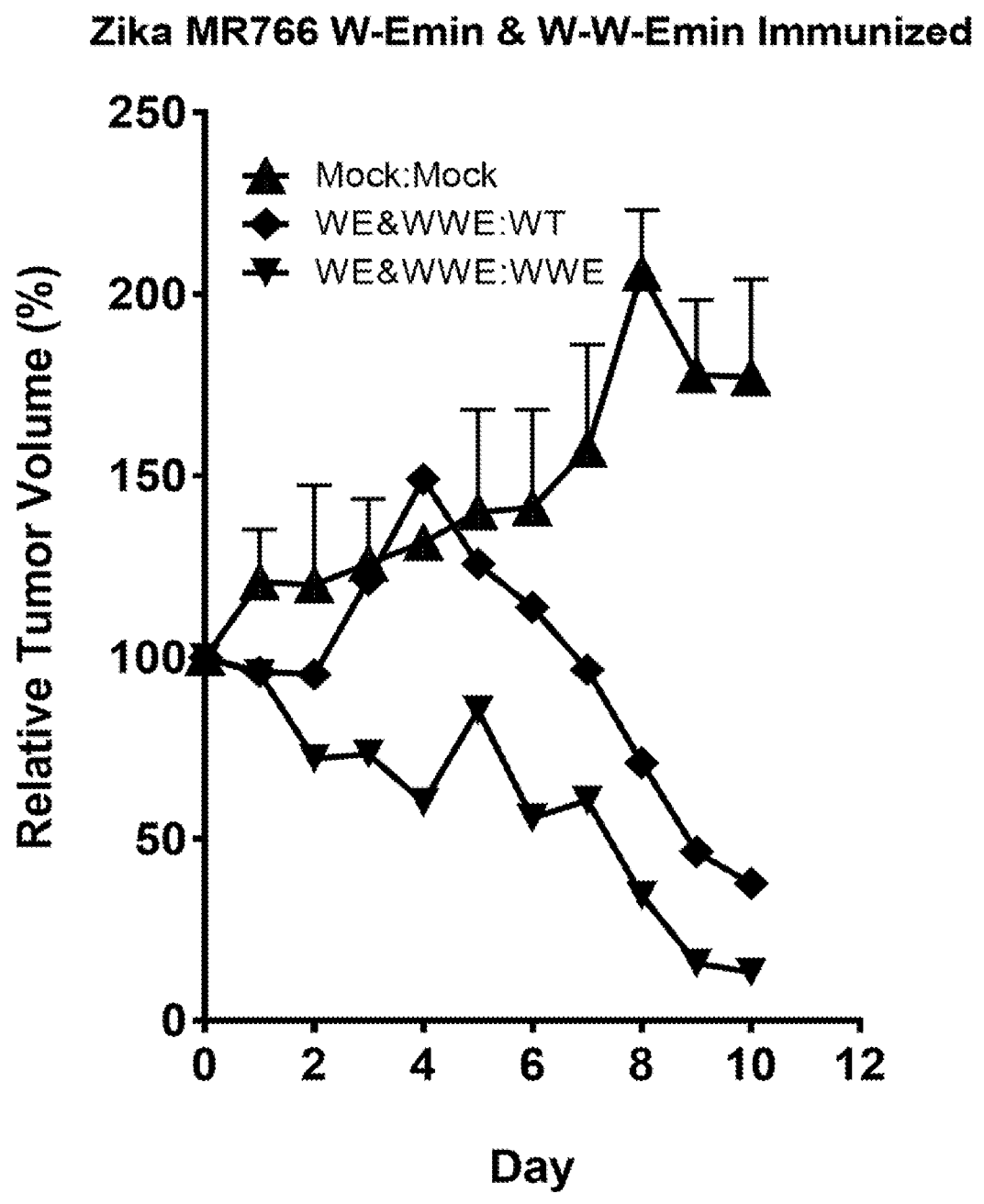

FIG. 17 describes the effects of prior immunization with Zika virus E-W/Min and E-W/W/Min on tumor size in DBA/2 mice implanted with CCL53.1 murine epithelial melanoma cells. Mice were vaccinated 5 times on Day 0, Day 14, Day 26, Day 71, and Day 85 with MR766 E-W/W/Min and MR766 E-W/Min or mock vaccinated with OptiPro medium. CCL53.1 cells were implanted into vaccinated or mock-vaccinated mice by injecting $1\times10^6$ CCL53.1 cells subcutaneously into the lower right flank in all animals. Implanted mice were treated with $1\times10^7$ PFU MR766 E-W/W/Min, $1\times10^7$ PFU MR766 WT, or mock treated by injection directly into the right flank tumor. Treatments were performed three times every two days and tumor size was measured daily through day 10 post-treatment. Mock immunized: mock treated DBA/2 mouse tumors increased steadily through day 10, however, both MR766 WT and MR766 E-W/W/Min treated tumors decreased in size. MR766 E-W/W/Min treatment was superior to MR766 WT treatment in vaccinated mice.

FIG. 18 describes the effects of MR766 WT treatment on tumor size in DBA/2 mice implanted with CCL53.1 murine epithelial melanoma cells. Mice were vaccinated 5 times on Day 0, Day 14, Day 26, Day 71, and Day 85 with MR766-W-W-E-Min or mock vaccinated with OptiPro medium. CCL53.1 cells were implanted into vaccinated or mock-vaccinated mice by injecting $1\times10^6$ CCL53.1 cells subcutaneously into the lower right flank in all animals. Implanted mice were treated with $1\times10^7$ PFU MR766 WT, or mock treated by injection directly into the right flank tumor. Treatments were performed three times every two days and tumor size was measured daily through day 10 post-treatment. Mock immunized: mock treated DBA/2 mouse tumors increased steadily through day 10 as did MR766 WT treated tumors in mock vaccinated mice. In MR766 E-W/W/Min vaccinated DBA/2 mice, MR766 WT treatment was effective in drastically reducing tumor size by day 10.

FIG. 19 describes the effect of vaccination on the efficacy of Zika virus MR766-E-W/W/Min treatment on tumor size in DBA/2 mice implanted with CCL53.1 murine epithelial melanoma cells. Mice were vaccinated 5 times on Day 0, Day 14, Day 26, Day 71, and Day 85 with MR766 E-W/W/Min, MR766 E-W/W/Min and E-W/Min, or mock vaccinated with OptiPro medium. CCL53.1 cells were implanted into vaccinated or mock-vaccinated mice by injecting $1\times10^6$ CCL53.1 cells subcutaneously into the lower right flank in all animals. Implanted mice were treated with $1\times10^7$ PFU MR766 E-W/W/Min, or mock treated by injection directly into the right flank tumor. Treatments were performed three times every two days and tumor size was measured daily through day 10 post-treatment. Mock immunized: mock treated DBA/2 mouse tumors increased steadily through day 10 as did MR766 E-W/W/Min treated tumors in mock vaccinated mice. In MR766 E-W/W/Min and combined MR766 E-W/W/Min plus E-W/Min vaccinated DBA/2 mice, tumor size was eliminated after MR766 E-W/W/Min treatment.

FIG. 20 describes the effect of MR766 E-W/W/Min treatment on off-side tumor size in DBA/2 mice either mock vaccinated with OptiPro medium or with MR766 E-W/W/Min and implanted with CCL53.1 murine epithelial melanoma cells. The mice in this study were injected subcutaneously on the lower right flank with $1\times10^6$ CCL53.1 murine epithelial melanoma cells which were treated by intratumoral injection with MR766 E-W/W/Min or mock treated with OptiPro medium. These mice were also injected subcutaneously into the lower left flank with $2.5\times10^5$ CCL53.1 cells which were not treated. The size of these tumors was also measured to assess immune-mediated clearance offsite of viral oncolysis. In mock-vaccinated, mock treated left flank tumors, the size increased steadily throughout 10 days post treatment. Left flank tumor size was maintained in mock vaccinated, MR766 E-W/W/Min treated mice however with MR766 E-W/W/Min vaccinated, E-W/W/Min treated mice the left flank tumor size increased several-fold before being reduced again. Left flank tumors in both MR766 E-W/W/Min treated groups were significantly smaller than in mock vaccinated, mock treated animals by one way ANOVA ($p<0.001$).

FIG. 21A-21B show that Zika virus treated animals are protected from tumor rechallenge. DBA/2 mice were initially vaccinated with diluent (mock), MR766 WT virus (WT), MR766 E-W/Min (EW), or MR766 E-W/W/Min (EWW). 21A) Mice in which the CCL53.1 tumors (melanoma) were been cured by treatment with either WT or EWW were rechallenged with 1×10$^6$ CCL53.1 cells in the opposite flank and compared to naïve control DBA/2 mice (n=5; RC01-13-1,2,3,4,5). Growth of tumors in the flank were assessed over 22 days post-tumor cell administration for each group. The Y axis is the average tumor size measured as mm$^3$ and X axis is day post-challenge (DPC); 21B) Tumors for each mouse were photographed on day 22 post injection.

FIG. 25A depicts average tumor volume (in mm$^3$) over time in Balb/C mice implanted with 4T1 cells and either mock-treated (n=5, red) or treated with 10$^7$ PFU of CodaVax-H1N1 M101/V6 (n=8, blue) on days 8, 10, 12, 14, 16, 18, 26, and 28 post-implantation (DPI). FIG. 25B depicts survival and was calculated using a human early end point of ≥400 mm$^3$ tumor volume. FIG. 25C depicts average tumor volume (in percentage of starting volume) over time in Balb/C mice implanted with 4T1 cells and either mock-treated (n=5, red) or treated with 10$^7$ PFU of CodaVax-H1N1 M101/V6 (n=8, blue) on days 8, 10, 12, 14, 16, 18, 26, and 28 post-implantation (DPI).

FIG. 31A-F—shows immune cell activation in DBA/2 mice either vaccinated on days 0, 14, 28, and 42 with 107 FFU MR766 E-W/Min or else mock-vaccinated with virus diluent. Vaccinated and mock-vaccinated mice were implanted on day 63 with 1×106 CCL53.1 melanoma cells delivered by the subcutaneous route and treatment was initiated on day 73 with 107 PFU MR766 E-W/W/Min or virus diluent delivered intratumorally on days 73, 75, and 77. Tumors were harvest and fixed in 4% paraformaldehyde on days 1 and 7 post-treatment (Days 74 and 80) for immunohistochemistry and staining to count immune markers and measure CD4+/CD8+ cell infiltration. FIG. 31A) Percent of CD45+ cells present in implanted CCL53.1 tumors 1 day post-treatment with MR766 E-W/W/Min alone or after E-W/Min vaccination followed by E-W/W/Min. FIG. 31B) Percent of CD4+ cells present in implanted CCL53.1 tumors 1 and 7 days post-treatment with MR766 E-W/W/Min alone or after E-W/Min vaccination followed by E-W/W/Min treatment. FIG. 31C) Percent of CD8+ cells present in implanted CCL53.1 tumors 7 days post-treatment. FIG. 31D) Percent of FoxP3+ cells present in implanted CCL53.1 tumors 1 day post-treatment. in immunohistochemistry of implanted CCL53.1 melanoma cells. FIG. 31E) CD45+ cell infiltration in implanted CCL53.1 tumors 1 day post-treatment is greatly increased in DBA/2 mice with prior MR766 E-W/Min vaccination as visualized by immunohistochemistry. FIG. 31F) CD8+ cell infiltration in implanted CCL53.1 tumors 7 days post-treatment is enhanced by prior MR766 E-W/Min vaccination as visualized by immunohistochemistry

DESCRIPTION OF THE INVENTION

Figure 1:
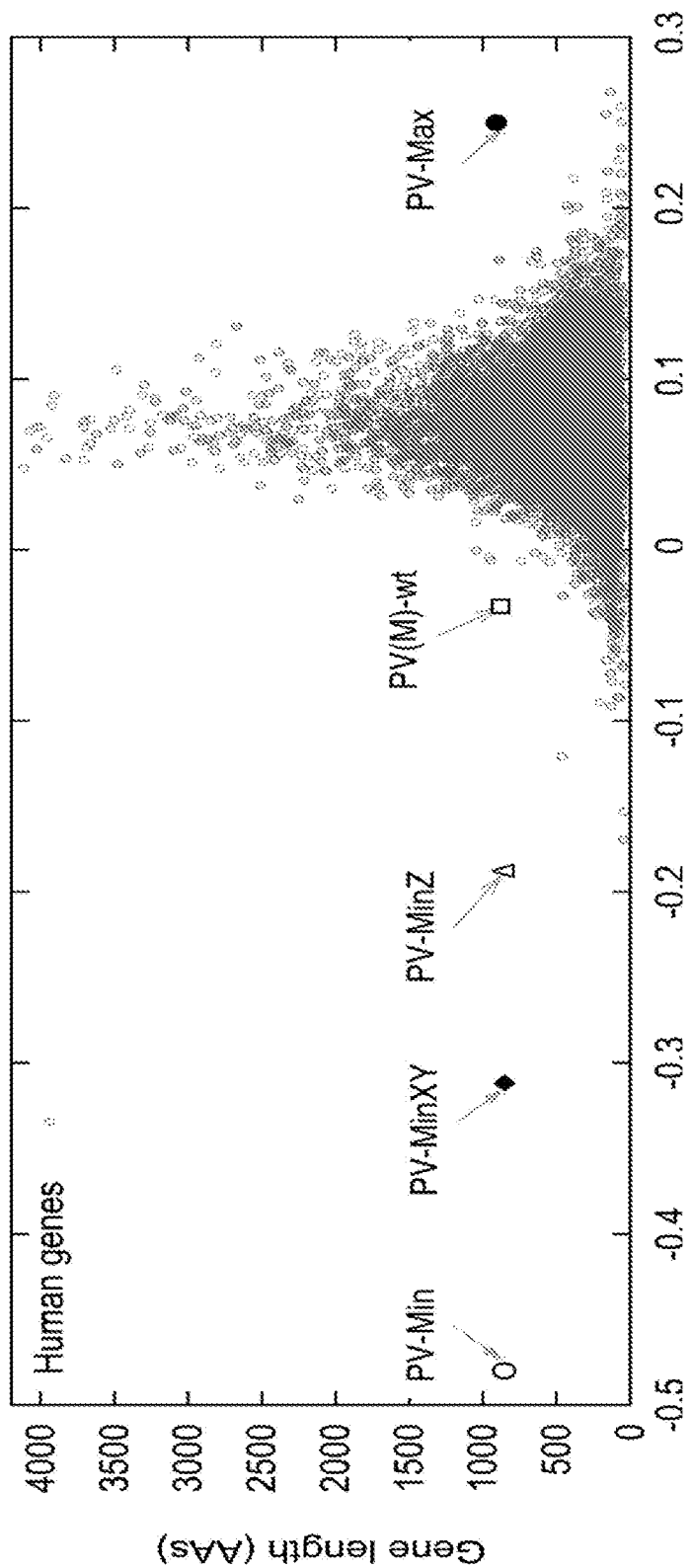
FIG. 1 depicts Codon-pair bias of all Human ORFs and synthetic P1 regions. Calculated codon pair bias (CPB) score for all 14,795 annotated human genes. Each gray dot represents the calculated CPB score of a gene plotted against its amino acid length. The CPB of the PV(M)-wt P1 region as well as the CPB of the designed synthetic poliovirus capsids PV-Min, PV-MinXY, PV-MinZ, and PV-Max, are indicated by arrows and labels.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Viral Modification by Deoptimizing Codon Pair Bias

According to aspects of the invention, codon pair bias can be altered independently of codon usage. For example, in a protein encoding sequence of interest, codon pair bias can be altered simply by directed rearrangement of its codons. In particular, the same codons that appear in the parent sequence, which can be of varying frequency in the host organism, are used in the altered sequence, but in different positions. In the simplest form, because the same codons are used as in the parent sequence, codon usage over the protein coding region being considered remains unchanged (as does the encoded amino acid sequence). Nevertheless, certain codons appear in new contexts, that is, preceded by and/or followed by codons that encode the same amino acid as in the parent sequence, but employing a different nucleotide triplet. Ideally, the rearrangement of codons results in codon pairs that are less frequent than in the parent sequence. In practice, rearranging codons often results in a less frequent codon pair at one location and a more frequent pair at a second location. By judicious rearrangement of codons, the codon pair usage bias over a given length of coding sequence can be reduced relative to the parent sequence. Alternatively, the codons could be rearranged so as to produce a sequence that makes use of codon pairs which are more frequent in the host than in the parent sequence.

Codon pair bias is evaluated by considering each codon pair in turn, scoring each pair according to the frequency that the codon pair is observed in protein coding sequences of the host, and then determining the codon pair bias for the sequence, as disclosed herein. It will be appreciated that one can create many different sequences that have the same codon pair bias. Also, codon pair bias can be altered to a greater or lesser extent, depending on the way in which codons are rearranged. The codon pair bias of a coding sequence can be altered by recoding the entire coding sequence, or by recoding one or more subsequences. As used herein, "codon pair bias" is evaluated over the length of a coding sequence, even though only a portion of the sequence may be mutated. Because codon pairs are scored in the context of codon usage of the host organism, a codon pair bias value can be assigned to wild type viral sequences and mutant viral sequences. According to aspects of the invention, a virus can be modified by recoding all or portions of the protein encoding sequences of the virus so as to reduce its codon pair bias.

According to aspects of the invention, codon pair bias is a quantitative property determined from codon pair usage of a host. Accordingly, absolute codon pair bias values may be determined for any given viral protein coding sequence. Alternatively, relative changes in codon pair bias values can be determined that relate a deoptimized viral protein coding sequence to a "parent" sequence from which it is derived. As viruses come in a variety of types (i.e., types I to VII by the Baltimore classification), and natural (i.e., virulent) isolates of different viruses yield different values of absolute codon pair bias, it is relative changes in codon pair bias that are usually more relevant to determining desired levels of attenuation. Accordingly, the invention provides modified viruses and methods of making such, wherein the modified viruses comprise viral genomes in which one or more protein encoding nucleotide sequences have codon pair bias reduced by mutation, and using these viruses and therapies for malignant tumors. In viruses that encode only a single protein (i.e., a polyprotein), all or part of the polyprotein can be mutated to a desired degree to reduce codon pair bias, and all or a portion of the mutated sequence can be provided in a recombinant viral construct. For a virus that separately encodes multiple proteins, one can reduce the codon pair bias of all of the protein encoding sequences simultaneously, or select only one or a few of the protein encoding sequences for modification. The reduction in codon pair bias is determined over the length of a protein encoding sequences, and is at least about 0.05, or at least about 0.1, or at least about 0.15, or at least about 0.2, or at least about 0.3, or at least about 0.4. Depending on the virus, the absolute codon pair bias, based on codon pair usage of the host, can be about −0.05 or less, or about −0.1 or less, or about −0.15 or less, or about −0.2 or less, or about −0.3 or less, or about −0.4 or less.

It will be apparent that codon pair bias can also be superimposed on other sequence variation. For example, a coding sequence can be altered both to encode a protein or polypeptide which contains one or more amino acid changes and also to have an altered codon pair bias. Also, in some cases, one may shuffle codons to maintain exactly the same codon usage profile in a codon-bias reduced protein encoding sequence as in a parent protein encoding sequence. This procedure highlights the power of codon pair bias changes, but need not be adhered to. Alternatively, codon selection can result in an overall change in codon usage is a coding sequence. In this regard, it is noted that in certain examples provided herein, (e.g., the design of PV-Min) even if the codon usage profile is not changed in the process of generating a codon pair bias minimized sequence, when a portion of that sequence is subcloned into an unmutated sequence (e.g., PV-MinXY or PV-MinZ), the codon usage profile over the subcloned portion, and in the hybrid produced, will not match the profile of the original unmutated protein coding sequence. However, these changes in codon usage profile have minimal effect of codon pair bias.

Similarly, it is noted that, by itself, changing a nucleotide sequence to encode a protein or polypeptide with one or many amino acid substitutions is also highly unlikely to produce a sequence with a significant change in codon pair bias. Consequently, codon pair bias alterations can be recognized even in nucleotide sequences that have been further modified to encode a mutated amino acid sequence. It is also noteworthy that mutations meant by themselves to increase codon bias are not likely to have more than a small effect on codon pair bias. For example, as disclosed herein, the codon pair bias for a modified virus mutant recoded to maximize the use of nonpreferred codons (PV-AB) is decreased from wild type (PV-1(M)) by about 0.05 (Mueller et al. 2006). Also noteworthy is that such a protein encoding sequence have greatly diminished sequence diversity. To the contrary, substantial sequence diversity is maintained in codon pair bias modified sequences of the invention. Moreover, the significant reduction in codon pair bias obtainable without increased use of rare codons suggests that instead of maximizing the use of nonpreferred codons, it would be beneficial to rearrange nonpreferred codons with a sufficient number of preferred codons in order to more effectively reduce codon pair bias.

The extent and intensity of mutation can be varied depending on the length of the protein encoding nucleic acid, whether all or a portion can be mutated, and the desired reduction of codon pair bias. In an embodiment of the invention, a protein encoding sequence is modified over a length of at least about 100 nucleotides, or at least about 200 nucleotides, or at least about 300 nucleotides, or at least about 500 nucleotides, or at least about 1000 nucleotides.

The term "parent" virus or "parent" protein encoding sequence is used herein to refer to viral genomes and protein encoding sequences from which new sequences, which may be more or less modified, are derived. Accordingly, a parent virus can be a "wild type" or "naturally occurring" prototypes or isolate or variant or a mutant specifically created or selected on the basis of real or perceived desirable properties.

Using de novo DNA synthesis, the capsid coding region (the P1 region from nucleotide 755 to nucleotide 3385) of PV(M) was redesigned to introduce the largest possible number of rarely used codon pairs (virus PV-Min). Cells transfected with PV-Min mutant RNA were not killed, and no viable virus could be recovered. Subcloning of fragments (PV-Min$^{755-2470}$, PV-Min$_{2470-3386}$) of the capsid region of PV-Min into the wt background produced very debilitated, but not dead, virus. This result substantiates the effectiveness of varying the extent of the codon pair deoptimized sequence that is substituted into a wild type parent virus genome in order to vary the codon pair bias for the overall sequence and the attenuation of the viral product.

Virus with deoptimized codon pair bias are attenuated. As exemplified in the reference by Coleman et al. in 2008, CD155tg mice survived challenge by intracerebral injection of attenuated virus in amounts 1000-fold higher than would be lethal for wild type virus. These findings demonstrate the power of deoptimization of codon pair bias to minimize lethality of a virus. Further, the viability of the virus can be balanced with a reduction of infectivity by choosing the degree of codon pair bias deoptimization. Further, once a degree or ranges of degrees of codon pair bias deoptimization is determined that provides desired attenuation properties, additional sequences can be designed to attain that degree of codon pair bias. For example, SEQ ID NO:1 provides a modified virus sequence with a codon pair bias of about −0.2, and mutations distributed over the region encompassing the mutated portions of PV-MinY.

Algorithms for Sequence Design

The inventors have developed several algorithms for gene design that optimize the DNA sequence for particular desired properties while simultaneously coding for the given amino acid sequence. In particular, algorithms for maximizing or minimizing the desired RNA secondary structure in the sequence (Cohen and Skiena, 2003) as well as maximally adding and/or removing specified sets of patterns (Skiena, 2001), have been developed. The former issue arises in designing viable viruses, while the latter is useful to optimally insert restriction sites for technological reasons. The extent to which overlapping genes can be designed that simultaneously encode two or more genes in alternate reading frames has also been studied. This property of different functional polypeptides being encoded in different reading frames of a single nucleic acid is common in viruses and can be exploited for technological purposes such as weaving in antibiotic resistance genes.

The first generation of design tools for synthetic biology has been built, as described by Jayaraj et al. (2005) and Richardson et al. (2006). These focus primarily on optimizing designs for manufacturability (i.e., oligonucleotides without local secondary structures and end repeats) instead of optimizing sequences for biological activity. These first-generation tools may be viewed as analogous to the early VLSI CAD tools built around design rule-checking, instead of supporting higher-order design principles.

As exemplified herein, a computer-based algorithm can be used to manipulate the codon pair bias of any coding region. The algorithm has the ability to shuffle existing codons and to evaluate the resulting CPB, and then to reshuffle the sequence, optionally locking in particularly "valuable" codon pairs. The algorithm also employs a form of "simulated annealing" so as not to get stuck in local minima. Other parameters, such as the free energy of folding of RNA, may optionally be under the control of the algorithm as well in order to avoid creation of undesired secondary structures. The algorithm can be used to find a sequence with a minimum codon pair bias, and in the event that such a sequence does not provide a viable virus, the algorithm can be adjusted to find sequences with reduced, but not minimized biases. Of course, a viable viral sequence could also be produced using only a subsequence of the computer minimized sequence.

Whether or not performed with the aid of a computer, using, for example, a gradient descent, or simulated annealing, or another minimization routine. An example of the procedure that rearranges codons present in a starting sequence can be represented by the following steps:
1) Obtain wild-type viral genome sequence.
2) Select protein coding sequences to target for modified design.
3) Lock down known or conjectured DNA segments with non-coding functions.
4) Select desired codon distribution for remaining amino acids in redesigned proteins.
5) Perform random shuffle of unlocked codon positions and calculate codon-pair score.
6) Further reduce (or increase) codon-pair score optionally employing a simulated annealing procedure.
7) Inspect resulting design for excessive secondary structure and unwanted restriction site:
   a. if yes→go to step (5) or correct the design by replacing problematic regions with wild-type sequences and go to step (8).
8) Synthesize DNA sequence corresponding to virus design.
9) Create viral construct and assess expression:
   a. if too attenuated, prepare subclone construct and go to 9;
   b. if insufficiently attenuated, go to 2.

Alternatively, one can devise a procedure which allows each pair of amino acids to be deoptimized by choosing a codon pair without a requirement that the codons be swapped out from elsewhere in the protein encoding sequence.

Viruses and Modified Viruses

Many viruses can be modified by the methods disclosed herein for use to treat cancer. The virus can be a dsDNA virus (e.g., Adenoviruses, Herpesviruses, Poxviruses), a single stranded "plus" sense DNA virus (e.g., Parvoviruses) a double stranded RNA virus (e.g., Reoviruses), or a single stranded "minus" sense RNA virus (e.g. Orthomyxoviruses, Rhabdoviruses). In certain non-limiting embodiments of the present invention, the virus is poliovirus (PV), rhinovirus, influenza virus, dengue fever virus, West Nile disease virus, chickenpox (varicella-zoster virus), measles (a paramyxovirus), mumps (a paramyxovirus), rabies (Lyssavirus), human papillomavirus, Kaposi's sarcoma-associated herpesvirus, Herpes Simplex Virus (HSV Type 1), or genital herpes (HSV Type 2).

In various embodiments, the modified virus belongs to the Picornaviridae virus family and all related genera, strains, types and isolates.

Poliomyelitis is a disease of the central nervous system caused by infection with poliovirus. Poliovirus is a human enterovirus that belongs to the Picornaviridae family and is classified into three stable serotypes. It is spherical, 20 nm in size, and contains a core of RNA coated with a capsule consisting of proteins. It is transmitted through the mucosa of the mouth, throat or the alimentary canal. All three modified virus serotypes have been reported as causative agents of paralytic poliomyelitis, albeit at different frequencies (type 1>type 2>type 3).

However, infection by modified viruses does not necessarily lead to the development of poliomyelitis. On the contrary, the majority of infections (98-99%) lead to local gastrointestinal replication of the virus causing only mild symptoms, or no symptoms at all. Rarely does modified viruses invade the CNS where it selectively targets spinal cord anterior horn and medullary motor neurons for destruction. Bodian, D., in: *Diseases of the Nervous System*, Minckler, J. ed., McGraw-Hill, New York, pp. 2323-2339 (1972).

The unusually restricted cell tropism of modified viruses leads to unique pathognomonic features. They are characterized by motor neuron loss in the spinal cord and the medulla, giving rise to the hallmark clinical sign of poliomyelitis, flaccid paralysis. Other neuronal components of the central nervous system as well as glial cells typically escape infection. In infected brain tissue under the electron microscope, severe changes are observed in motor neurons whereas no significant alterations are observed in the neuroglial components. Normal astrocytes and oligodendrocytes may be seen next to degenerate neurons or axons without evidence of infection or reaction. Bodian, D., supra. The restricted tropism of modified viruses is not understood. In addition to the restricted cell and tissue tropism, modified viruses only infect primates and primate cell cultures. Other mammalian species remain unaffected.

The isolation of modified viruses in 1908 led to intensive research efforts to understand the mechanisms of infection. The earlier work required the use of monkeys and chimpanzees as animal models. Such animals with longer life cycles are very costly and difficult to use in research. The discovery of the human poliovirus receptor (PVR) also known as CD155, the cellular docking molecule for poliovirus, led to the development of a transgenic mouse expressing the human modified viruses' receptor as a new animal model for poliomyelitis. The pathogenicity of modified viruses may be studied using the transgenic mice.

The early research efforts have also led to the development of attenuated PV strains that lack neuropathogenic potential and soon were tested as potential vaccine candidates for the prevention of poliomyelitis. The most effective of these are the Sabin strains of type 1, 2, and 3, of modified viruses developed by A. Sabin. After oral administration of the live attenuated strains of modified viruses (the Sabin strains) vaccine-associated paralytic poliomyelitis has been observed in extremely rare cases. The occurrence of vaccine-associated paralytic polio has been correlated with the emergence of neurovirulent variants of the attenuated Sabin strains after immunization.

In order to understand the invention, it is important also to have an understanding of the structure of poliovirus. All picornaviruses including enteroviruses, cardioviruses, rhinoviruses, aphthoviruses, hepatovirus and parechoviruses contain 60 copies each of four polypeptide chains: VP1, VP2, VP3, and VP4. These chains are elements of protein subunits called mature "protomers". The protomer is defined as the smallest identical subunit of the virus. Traces of a fifth protein, VP0, which is cleaved to VP2 and VP4 are also observed. Together, these proteins form the shell or coat of poliovirus.

The picornaviral genome has a single strand of messenger-active RNA. The genomic messenger active RNA has a "+" strand which is polyadenylated at the 3' terminus and carries a small protein, VPg, covalently attached to the 5' end. The first picornaviral RNA to be completely sequenced and cloned into DNA was that of a type 1 poliovirus. However, polioviruses lack a 5'm$^7$GpppG cap structure, and the efficient translation of RNA requires ribosomal binding that is accomplished through an internal ribosomal entry site (IRES) within the 5' untranslated region (5'NTR).

Figure 2:
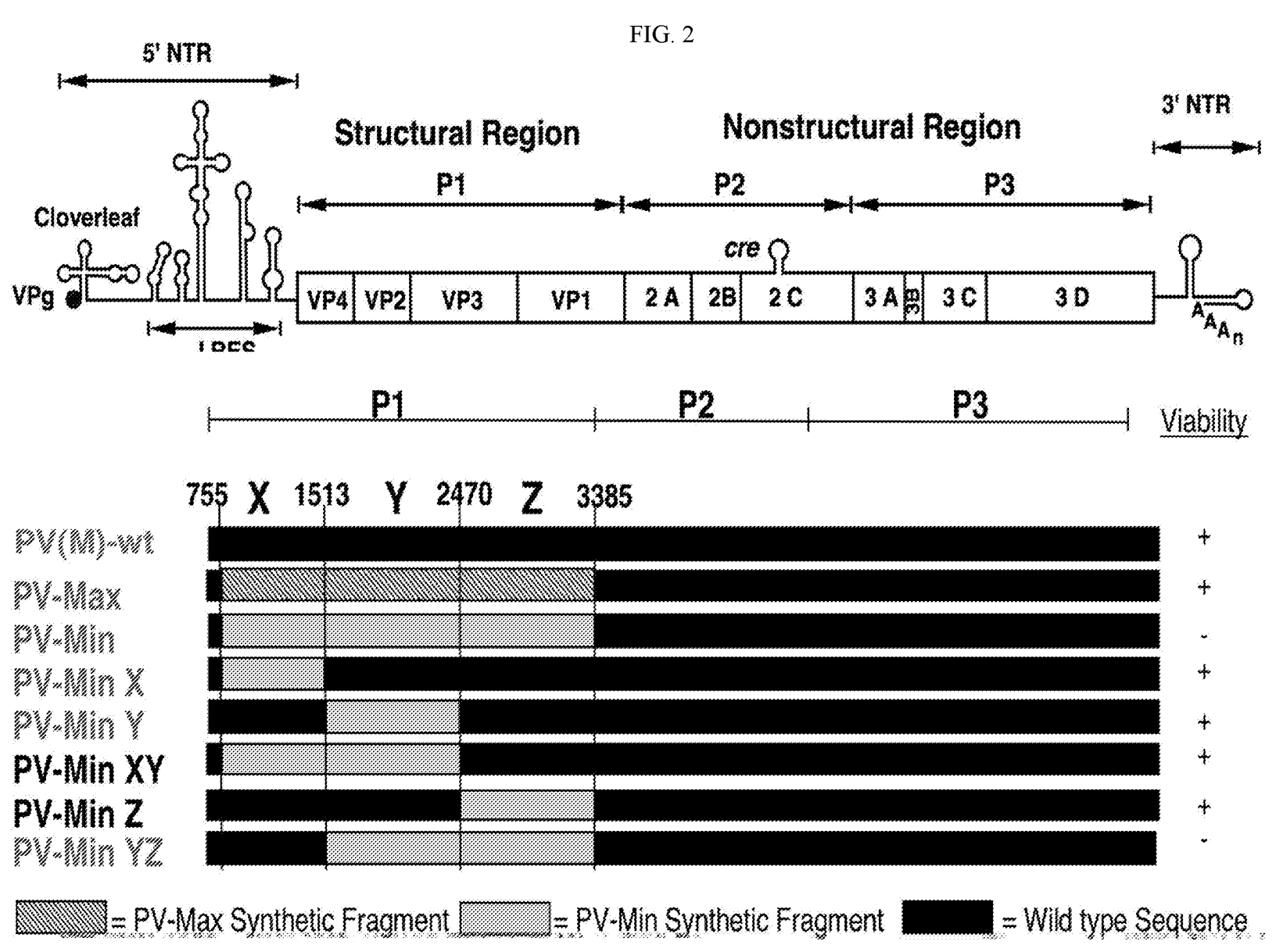

The common organizational pattern of a modified viruses is represented schematically in FIG. 2, which comprises 5'NTR, P1, P2, P3 and 3'NTR with a polyadenylated tail. The 5'NTR comprises 6 domains arbitrarily designated as I, II, III, IV, V, and VI. The IRES comprises domains II-VI. P1 is the coding region for structural proteins also known as the capsid proteins. P2 and P3 encode the non-structural proteins.

In nature, three immunologically distinct modified virus types occur: serotype 1, 2, and 3. These types are distinct by specific sequences in their capsid proteins that interact with specific sets of neutralizing antibodies. All three types occur in different strains, and all naturally occurring types and strains can cause poliomyelitis. They are, thus, neurovirulent. The genetic organization and the mechanism of replication of the serotypes are identical; the nucleotide sequences of their genomes are >90% identical. Moreover, all polioviruses, even the attenuated vaccine strains, use the same cellular receptor (CD155) to enter and infect the host cells; and they express the same tropism for tissues in human and susceptible transgenic animals.

The neuropathogenicity of modified viruses can be attenuated by mutations in the regions specifying the P1 and P3 proteins as well as in the internal ribosomal entry site (IRES) within the 5'NTR. The Sabin vaccine strains of type 1, 2, and 3 carry a single mutation each in domain V of their IRES elements that has been implicated in the attenuation phenotype. Despite their effectiveness as vaccines, the Sabin strains retain a neuropathogenic potential in animal models for poliomyelitis. Albeit at a very low rate, they can cause the disease in vaccines.

Indeed, the single point mutations in the IRES element of each Sabin vaccine strain can revert in a vaccine within a period of 36 hours to several days. Overall, vaccine associated acute poliomyelitis occurs in the United States at a rate of 1 in 530,000 vaccines. The polioviruses isolated from vaccinated patients with poliomyelitis may also have mutations reverted in different positions of their genomes.

In other embodiments, the modified virus is derived from influenza virus A, influenza virus B, or influenza virus C. In further embodiments, the influenza virus A belongs to but is not limited to subtype H10N7, H10N1, H10N2, H10N3, H10N4, H10N5, H10N6, H10N7, H10N8, H10N9, H11N1, H11N2, H11N3, H11N4, H11N6, H11N8, H11N9, H12N1, H12N2, H12N4, H12N5, H12N6, H12N8, H12N9, H13N2, H13N3, H13N6, H13N9, H14N5, H14N6, H15N2, H15N8, H15N9, H16N3, H1N1, H1N2, H1N3, H1N5, H1N6, H1N8, H1N9, H2N1, H2N2, H2N3, H2N4, H2N5, H2N6, H2N7, H2N8, H2N9, H3N1, H3N2, H3N3, H3N4, H3N5, H3N6, H3N8, H3N9, H4N1, H4N2, H4N3, H4N4, H4N5, H4N6, H4N7, H4N8, H4N9, H5N1, H5N2, H5N3, H5N4, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H8N2, H8N4, H8N5, H9N1, H9N2, H9N3, H9N4, H9N5, H9N6, H9N7, H9N8, H9N9 and unidentified subtypes. In various embodiments, the modified virus is H1N1 M101/V6 as disclosed herein. In various embodiments, one or more segments of influenza virus A is recoded (e.g., deoptimized). In various embodiments the HA segment is recoded. In various embodiments, the NA segment is recoded. In various embodiments, both the HA segment and the NA segments are recoded. In various embodiments, the recoded influenza virus A has a codon bias or a codon pair bias reduction as discussed herein for other viruses.

In various embodiments, the modified virus belongs to the Flaviviridae virus family and all related genera, strains, types and isolates. In various embodiments, the modified virus is the Zika virus species, as further discussed herein.

In various embodiments, the modified virus belongs to the Adenoviridae virus family and all related genera, strains, types and isolates for example but not limited to human adenovirus A, B C.

In various embodiments, the modified virus belongs to the Herpesviridae virus family and all related genera, strains, types and isolates for example but not limited to herpes simplex virus.

In various embodiments, the modified virus belongs to the Reoviridae virus family and all related genera, strains, types and isolates.

In various embodiments, the modified virus belongs to the Papillomaviridae virus family and all related genera, strains, types and isolates.

In various embodiments, the modified virus belongs to the Poxviridae virus family and all related genera, strains, types and isolates.

In various embodiments, the modified virus belongs to the Paramyxoviridae virus family and all related genera, strains, types and isolates.

In various embodiments, the modified virus belongs to the Orthomyxoviridae virus family and all related genera, strains, types and isolates.

In various embodiments, the modified virus belongs to the Bunyaviridae virus family and all related genera, strains, types and isolates.

In various embodiments, the modified virus belongs to the Nidovirales virus family and all related genera, strains, types and isolates.

In various embodiments, the modified virus belongs to the Caliciviridae virus family and all related genera, strains, types and isolates.

In various embodiments, the modified virus belongs to the Rhabdoviridae family and all related genera, strains, types and isolates.

In various embodiments, the modified virus belongs to the Togaviridae family and all related genera, strains, types and isolates.

In various embodiments, the modified virus is any one of SEQ ID NOs: 1, 2, 3, 4, 5 or 6.

Modified Zika Virus

Embodiments of the invention uses attenuated Zika viruses in which expression of viral proteins is reduced, which have excellent growth properties useful to vaccine production, yet possess an extraordinary safety profile and enhanced protective characteristics. The attenuated viruses proliferate nearly as well as wild type virus, have highly attenuated phenotypes, as revealed by $LD_{50}$ values, are unusually effective in providing protective immunity against challenge by Zika virus of the same strain, and also provide protective immunity against challenge by Zika virus of other strains.

In certain embodiments of the invention, the attenuated Zika viruses of the invention comprise a recoded pre-membrane/Envelope (E) encoding region, a recoded non-structural protein 3 (NS3) encoding region, or both E and NS3 encoding regions. That the C, NS1, NS2, NS4, or NS5 protein encoding regions are not recoded does not exclude mutations and other variations in those sequences, but only means that any mutations or variations made in those sequences have little or no effect on attenuation. Little or no effect on attenuation includes one or both of the following: 1) The mutations or variations in the That the C, NS1, NS2, NS4, or NS5 encoding regions do not reduce viral replication or viral infectivity more than 20% when the variant C, NS1, NS2, NS4, or NS5 encoding region is the only variant in a test Zika virus; 2) Mutations or variations in any of the C, NS1, NS2, NS4, or NS5 encoding regions represent fewer than 10% of the nucleotides in that coding sequence.

The Zika viruses used the invention are highly attenuated. In embodiments of the invention, compared to wild type, the Zika viruses are at least 5,000 fold attenuated, or at least 10,000 fold attenuated, or at least 20,000 fold attenuated, or at least 33,000 fold attenuated, or at least 50,000 fold attenuated, of at least 100,000 fold attenuated in the AG129 mouse model compared to a wild type virus having proteins of the same sequence but encoded by a different nucleotide sequence.

The attenuated Zika viruses used in the invention also exhibit a large margin of safety (i.e., the difference between $LD_{50}$ and $PD_{50}$), thus have high safety factors, defined herein as the ratio of $LD_{50}/PD_{50}$. In certain embodiments of the invention, the safety factor is at least $10^2$, or at least $10^3$, or at least $10^4$, or at least $10^5$, or at least $2\times10^5$, or at least $5\times10^5$, or at least $10^6$, or at least $2\times10^6$, or at least $5\times10^6$. In certain embodiments, the safety factor is from $10^2$ to $10^3$, or from $10^3$ to $10^4$, or from $10^4$ to $10^5$, or from $10^5$ to $10^6$.

The recoding of E and NS3 protein encoding sequences of the attenuated viruses of the invention can have been made utilizing any algorithm or procedure known in the art or newly devised for recoding a protein encoding sequence. According to the invention, nucleotide substitutions are engineered in multiple locations in the E and NS3 coding sequences, wherein the substitutions introduce a plurality of synonymous codons into the genome. In certain embodiments, the synonymous codon substitutions alter codon bias, codon pair bias, the density of infrequent codons or infrequently occurring codon pairs, RNA secondary structure, CG and/or TA (or UA) dinucleotide content, C+G content, translation frameshift sites, translation pause sites, the presence or absence of microRNA recognition sequences or any combination thereof, in the genome. The codon substitutions may be engineered in multiple locations distributed throughout the E and NS3 coding sequences, or in the multiple locations restricted to a portion of the E and NS3 coding sequences. Because of the large number of defects (i.e., nucleotide substitutions) involved, the invention provides a means of producing stably attenuated viruses and live vaccines.

As discussed herein, in some embodiments, a virus coding sequence is recoded by substituting one or more codon with synonymous codons used less frequently in the Zika host (e.g., humans, mosquitoes). In some embodiments, a virus coding sequence is recoded by substituting one or more codons with synonymous codons used less frequently in the Zika virus. In certain embodiments, the number of codons substituted with synonymous codons is at least 5. In some embodiments, at least 10, or at least 20 codons are substituted with synonymous codons.

In some embodiments, virus codon pairs are recoded to reduce (i.e., lower the value of) codon-pair bias. In certain embodiments, codon-pair bias is reduced by identifying a codon pair in an E or NS3 coding sequence having a codon-pair score that can be reduced and reducing the codon-pair bias by substituting the codon pair with a codon pair that has a lower codon-pair score. In some embodiments, this substitution of codon pairs takes the form of rearranging existing codons of a sequence. In some such embodiments, a subset of codon pairs is substituted by rearranging a subset of synonymous codons. In other embodiments, codon pairs are substituted by maximizing the number of rearranged synonymous codons. It is noted that while rearrangement of codons leads to codon-pair bias that is reduced (made more negative) for the virus coding sequence overall, and the rearrangement results in a decreased CPS at many locations, there may be accompanying CPS increases at other locations, but on average, the codon pair scores, and thus the CPB of the modified sequence, is reduced. In some embodiments, recoding of codons or codon-pairs can take into account altering the G+C content of the E and NS3 coding sequences. In some embodiments, recoding of codons or codon-pairs can take into account altering the frequency of CG and/or TA dinucleotides in the E and NS3 coding sequences.

In certain embodiments, the recoded E protein-encoding sequence has a codon pair bias less than −0.1, or less than −0.2, or less than −0.3, or less than −0.4. In certain embodiments, the recoded (i.e., reduced-expression) NS3 protein-encoding sequence has a codon pair bias less than −0.1, or less than −0.2, or less than −0.3, or less than −0.4. In certain embodiments, the codon pair bias of the recoded HA protein encoding sequence is reduced by at least 0.1, or at least 0.2, or at least 0.3, or at least 0.4, compared to the parent E protein encoding sequence from which it is derived. In certain embodiments, the codon pair bias of the recoded NS3 protein encoding sequence is reduced by at least 0.1, or at least 0.2, or at least 0.3, or at least 0.4, compared to the parent NS3 protein encoding sequence from which it is derived. In certain embodiments, rearrangement of synonymous codons of the E protein-encoding sequence provides a codon-pair bias reduction of at least 0.1, or at least 0.2, or at least 0.3, or at least 0.4, parent E protein encoding sequence from which it is derived. In certain embodiments, rearrangement of synonymous codons of the NS3 protein-encoding sequence provides a codon-pair bias reduction of at least 0.1, or at least 0.2, or at least 0.3, or at least 0.4, parent NS3 protein encoding sequence from which it is derived.

Usually, these substitutions and alterations are made and reduce expression of the encoded virus proteins without altering the amino acid sequence of the encoded protein. In certain embodiments, the invention also includes alterations in the E and/or NS3 coding sequences that result in substitution of non-synonymous codons and amino acid substitutions in the encoded protein, which may or may not be conservative.

Most amino acids are encoded by more than one codon. See the genetic code in Table 6. For instance, alanine is encoded by GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy.

TABLE 6

Genetic Code

| U | C | A | G | |
|---|---|---|---|---|
| U | Phe | Ser | Tyr | Cys | U |
|   | Phe | Ser | Tyr | Cys | C |
|   | Leu | Ser | STOP | STOP | A |
|   | Leu | Ser | STOP | Trp | G |
| C | Leu | Pro | His | Arg | U |
|   | Leu | Pro | His | Arg | C |
|   | Leu | Pro | Gln | Arg | A |
|   | Leu | Pro | Gln | Arg | G |
| A | Ile | Thr | Asn | Ser | U |
|   | Ile | Thr | Asn | Ser | C |
|   | Ile | Thr | Lys | Arg | A |
|   | Met | Thr | Lys | Arg | G |
| G | Val | Ala | Asp | Gly | U |
|   | Val | Ala | Asp | Gly | C |
|   | Val | Ala | Glu | Gly | A |
|   | Val | Ala | Glu | Gly | G |

[a] The first nucleotide in each codon encoding a particular amino acid is shown in the left-most column; the second nucleotide is shown in the top row; and the third nucleotide is shown in the right-most column.

According to the invention, viral attenuation is accomplished by reducing expression viral proteins through codon pair deoptimization of E and NS3 coding sequences. One way to reduce expression of the coding sequences is by a reduction in codon pair bias, but other methods can also be used, alone or in combination. While codon bias may be changed, adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties.

Codon pair bias of a protein-encoding sequence (i.e., an open reading frame) is calculated as set forth above and described in Coleman et al., 2008.

Viral attenuation and induction or protective immune responses can be confirmed in ways that are well known to one of ordinary skill in the art, including but not limited to, the methods and assays disclosed herein. Non-limiting examples include plaque assays, growth measurements, reduced lethality in test animals, and protection against subsequent infection with a wild type virus.

In various embodiments, the invention uses viruses that are highly attenuated. Such Zika virus varieties include viruses in the so-called African and Asian lineages. Examples of attenuated Zika protein coding sequences include SEQ ID Nos. 2, 3, and 4.

Codon Substitutions

In certain embodiments, the synonymous codon substitutions for the modified virus alter codon bias, codon pair bias, density of deoptimized codons and deoptimized codon pairs, RNA secondary structure, CpG dinucleotide content, C+G content, translation frameshift sites, translation pause sites, the presence or absence microRNA recognition sequences or any combination thereof, in the genome. The codon substitutions may be engineered in multiple locations distributed throughout the genome, or in the multiple locations restricted to a portion of the genome.

In further embodiments, the portion of the genome is the capsid coding region.

In further embodiments, the portion of the genome is the structural protein coding region of the genome.

In further embodiments, the portion of the genome is the non-structural protein coding region of the genome.

Modified Oncolytic Virus Composition

This invention further provides a method of synthesizing any of the modified viruses described herein, the method comprising (a) identifying codons in multiple locations within at least one non-regulatory portion of the viral genome, which codons can be replaced by synonymous codons; (b) selecting a synonymous codon to be substituted for each of the identified codons; and (c) substituting a synonymous codon for each of the identified codons.

In certain embodiments of the instant methods, steps (a) and (b) are guided by a computer-based algorithm for Synthetic Attenuated Virus Engineering (SAVE) that permits design of a viral genome by varying specified pattern sets of deoptimized codon distribution and/or deoptimized codon-pair distribution within preferred limits. The invention also provides a method wherein, the pattern sets alternatively or additionally comprise, density of deoptimized codons and deoptimized codon pairs, RNA secondary structure, CpG dinucleotide content, UpA dinucleotide content C+G content, overlapping coding frames, restriction site distribution, frameshift sites, or any combination thereof.

In other embodiments, step (c) is achieved by de novo synthesis of DNA containing the synonymous codons and/or codon pairs and substitution of the corresponding region of the genome with the synthesized DNA. In further embodiments, the entire genome is substituted with the synthesized DNA. In still further embodiments, a portion of the genome is substituted with the synthesized DNA. In yet other embodiments, said portion of the genome is the capsid coding region.

A "subject" means any animal or artificially modified animal. Animals include, but are not limited to, humans, non-human primates, cows, horses, sheep, pigs, dogs, cats, rabbits, ferrets, rodents such as mice, rats and guinea pigs, and birds. Artificially modified animals include, but are not limited to, SCID mice with human immune systems, and CD155tg transgenic mice expressing the human poliovirus receptor CD155. In a preferred embodiment, the subject is a human. Preferred embodiments of birds are domesticated poultry species, including, but not limited to, chickens, turkeys, ducks, and geese.

In various embodiments, the modified virus is derived from a wild-type virus or a previously modified virus, by substituting at least one genomic region of the wild-type virus with a codon-pair deoptimized region encoding a similar protein sequence, wherein the codon pair bias of the modified sequence is less than the codon pair bias of the parent virus, and is reduced by at least about 0.05, or at least about 0.1, or at least about 0.2.

In various embodiments, the modified virus is derived from a wild-type virus or a previously modified virus, by substituting at least one genomic region of the wild-type virus with a region with increased CpG di-nucleotide encoding a similar protein sequence, wherein in the increase of the CpG di-nucleotide is at least 41 instances above the parent, or at least 21 instances above the parent viral genome.

In various embodiments, the modified virus is derived from a wild-type virus or a previously modified virus, by substituting at least one genomic region of the wild-type virus with a region with increased UpA di-nucleotide encoding a similar protein sequence, wherein in the increase of the UpA di-nucleotide is at least 26 instances above the parent, or at least 13 instances above the parent viral genome.

In various embodiments, the modified virus is derived from a wild-type virus or a previously modified virus, by substituting at least one genomic region of the wild-type virus with a region with increased UpA and the CpG di-nucleotide encoding a similar protein sequence, wherein in the increase of the UpA and the CpG di-nucleotide was at least 42 instances combined above the parent.

Synthesis of Recombinant Polioviruses

Recombinant modified viral chimeras can be synthesized by well-known recombinant DNA techniques. Any standard manual on DNA technology provides detailed protocols to produce the modified viral chimeras of the invention.

Determination of Reduced Pathogenicity of Modified Virus

The neurovirulence of the PV-Min chimeras XY and Z and PV-Max was tested in CD155tg mice via intracerebral injection with increasing doses of the viruses. Specifically, groupings of four to six, 6-8 week-old CD155tg mice were inoculated with varying doses and then observed for the onset of poliomyelitis. Control groupings of mice were injected in parallel experiments with PV(M)-wt. Injection doses were based on particles rather than PFU so as to normalize the quantity of virions inserted into the brain. The mice were monitored daily for the onset of flaccid paralysis, the characteristic symptom of poliomyelitis. The standard value used to quantify the virulence of a virus is the Lethal Dose 50 ($LD_{50}$). This value indicates the dose of inoculating virus at which fifty percent of the animals live and fifty percent die. The synthetic viruses PV-MinXY and PV-MinZ had a higher $LD_{50}$ than PV(M)-wt and therefore were, 1,500-fold based on particles or 20-fold based on PFU, less pathogenic (Table 4).

Assessment of the Oncolytic Properties of Poliovirus

The oncolytic properties of the modified viral chimeras of the present invention may also be assessed in vivo as follows. Experimental tumors are produced in athymic mice by subcutaneous or stereotactic intracerebral implantation of malignant cells. Tumor progression in untreated athymic mice and athymic mice that have been administered oncolytic modified virus recombinants following various treatment regimens are followed by clinical observation and pathological examination. The technique of tumor implantation into athymic mice is standard procedure described in detail in Fogh, J., et al.

Pharmaceutical Compositions

The modified viral chimeras of this invention are useful in prophylactic and therapeutic compositions for treating malignant tumors in various organs, such as: breast, colon, bronchial passage, epithelial lining of the gastrointestinal, upper respiratory and genito-urinary tracts, liver, prostate, the brain, or any other human tissue. In various embodiments, the modified viral chimers of the present invention are useful for treating solid tumors. In particular embodiments, the tumors treated is glioblastoma, adenocarcinoma, melanoma, or neuroblastoma. In various embodiments, the tumors treated is a triple-negative breast cancer.

The pharmaceutical compositions of this invention may further comprise other therapeutics for the prophylaxis of malignant tumors. For example, the modified viral chimeras of this invention may be used in combination with surgery, radiation therapy and/or chemotherapy. Furthermore, one or more modified viral chimeras may be used in combination with two or more of the foregoing therapeutic procedures. Such combination therapies may advantageously utilize lower dosages of the administered therapeutic agents, thus avoiding possible toxicities or adverse effects associated with the various monotherapies.

The pharmaceutical compositions of this invention comprise a therapeutically effective amount of one or more modified viral chimeras according to this invention, and a pharmaceutically acceptable carrier. By "therapeutically effective amount" is meant an amount capable of causing lysis of the cancer cells to cause tumor necrosis. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the modified viral chimeras.

The compositions of this invention may be in a variety of forms. These include, for example, liquid dosage forms, such as liquid solutions, dispersions or suspensions, injectable and infusible solutions. The preferred form depends on the intended mode of administration and prophylactic or therapeutic application. The preferred compositions are in the form of injectable or infusible solutions.

Prophylactic and Therapeutic Cancer Treatments

The present invention relates to the production of modified viruses that can be used as oncolytic therapy to treat different tumor types and methods of treating tumors and cancer by administering the modified viruses described herein.

Accordingly, various embodiments of the invention provide a modified virus, which comprises a modified viral genome containing nucleotide substitutions engineered in one or multiple locations in the genome, wherein the substitutions introduce a plurality of synonymous codons into the genome and/or a change of the order of existing codons for the same amino acid (change of codon pair utilization). In both cases, the original, wild-type amino acid sequences of the viral gene products are retained within 98%.

Most amino acids are encoded by more than one codon. See the genetic code in Table 1. For instance, alanine is encoded by GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy. Thus, to replace a given codon in a nucleic acid by a synonymous but less frequently used codon is to substitute a "deoptimized" codon into the nucleic acid.

Treatment of Existing Cancer

Various embodiments of the present invention provide for a method of inducing an oncolytic effect on a tumor or cancer cell. In various embodiments, this type of treatment can be made when a subject has been diagnosed with cancer. The method comprises administering a modified virus to a subject in need thereof, wherein the modified virus is derived from a wild-type virus or from a previously modified virus, by substituting at least one genomic region of the wild-type virus with a codon-pair deoptimized region encoding a similar protein sequence, wherein the codon pair bias of the modified sequence is less than the codon pair bias of the parent virus, and is reduced by at least about 0.05, or at least about 0.1, or at least about 0.2.

Various embodiments of the present invention provide for a method of inducing an oncolytic effect on a malignant tumor, comprising: administering a modified virus to a subject in need thereof, wherein the modified virus is derived from a wild-type virus or from a previously modified virus, by substituting at least one genomic region of the wild-type virus with a region with increased CpG di-nucleotide encoding a similar protein sequence, wherein in the increase of the CpG di-nucleotide is at least 41 instances above the parent, or at least 21 instances above the parent viral genome.

Various embodiments of the present invention provide for a method of inducing an oncolytic effect on a malignant tumor, comprising: administering a modified virus to a subject in need thereof, wherein the modified virus is derived from a wild-type virus or from a previously modified virus, by substituting at least one genomic region of the wild-type virus with a region with increased UpA di-nucleotide encoding a similar protein sequence, wherein in the increase of the UpA di-nucleotide is at least 26 instances above the parent, or at least 13 instances above the parent viral genome Various embodiments of the present invention provide for a method of inducing an oncolytic effect on a malignant tumor, comprising: administering a modified virus to a subject in need thereof, wherein the modified virus is derived from a wild-type virus or from a previously modified virus, by substituting at least one genomic region of the wild-type virus with a region with increased UpA and the CpG di-nucleotide encoding a similar protein sequence, wherein in the increase of the UpA and the CpG di-nucleotide was at least 42 instances combined above the parent.

Examples of other attenuated viruses that can also be utilized as the prime and/or boost dosages includes family and all related genera, strains, types and isolates of viruses described herein (e.g., in the "Viruses and Modified Viruses" section above) as well as attenuated viruses belonging to the Picornaviridae virus family and all related genera, strains, types and isolates; attenuated viruses belonging to the Herpesviridae virus family and all related genera, strains; attenuated viruses belonging to the Rhabdoviridae virus family and all related genera, strains, types and isolates; attenuated viruses belonging to the Reoviridae virus family and all related genera, strains; attenuated viruses belonging to the Poxviridae virus family and all related genera, strains; attenuated viruses belonging to the Togaviridae virus family and all related genera, strains.

In various embodiments, inducing an oncolytic effect on a malignant tumor results in treating the malignant tumor.

In various embodiments, the treatment further comprises administering a PD-1 inhibitor. In other embodiments, the treatment further comprises administering a PD-L1 inhibitor. In still other embodiments, the treatment further comprises administering both an PD-1 inhibitor and a PD-L1 inhibitor.

In various embodiments, the PD-1 inhibitor is an anti-PD1 antibody. In various embodiments, the PD-L1 inhibitor is an anti-PD-L1 antibody. Examples of PD-1 inhibitors and PD-L1 inhibitors are provided herein.

In various embodiments, the treatment of the malignant tumor decreases the likelihood of recurrence of the malignant tumor. It can also decrease the likelihood of having a second cancer that is different from the malignant tumor. If the subject develops a second cancer that is different from the malignant tumor and the treatment of the malignant tumor results in slowing the growth of the second cancer. In some embodiments, after remission of the malignant tumor, the subject develops a second cancer that is different from the malignant tumor and the treatment of the malignant tumor results in slowing the growth of the second cancer.

Prime-Boost Treatments

Various embodiments of the present invention provide for a method of eliciting an immune response and inducing an oncolytic effect on a tumor or cancer cell, using a prime-boost-type treatment regimen. In various embodiments, eliciting the immune response and inducing an oncolytic effect on the tumor or cancer cell results in treating a malignant tumor.

A prime dose of an attenuated virus or a modified virus of the present invention is administered to elicit an initial immune response. Thereafter, a boost dose of an attenuated virus or a modified virus of the present invention is administered to induce oncolytic effects on the tumor and/or to elicit an immune response comprising oncolytic effect against the tumor.

In various embodiments, the prime dose and the boost dose contains the same attenuated virus or modified virus of the present invention. In other embodiments, the prime dose and the boost does are different attenuated viruses or modified viruses of the present invention.

In various embodiments, the method comprises administering a prime dose of a modified virus to a subject in need thereof; and administering one or more boost dose of a modified virus to the subject in need thereof, wherein the prime dose and boost dose of the modified virus are each independently selected from (1) an attenuated virus produced by a method other than codon-pair deoptimization, (2) a modified virus derived from a wild-type virus or a previously modified virus, by substituting at least one genomic region of the wild-type virus with a codon-pair deoptimized region encoding a similar protein sequence, wherein the codon pair bias of the modified sequence is less than the codon pair bias of the parent virus, and is reduced by at least about 0.05, or at least about 0.1, or at least about 0.2, (3) a modified virus derived from a wild-type virus or a previously modified virus, by substituting at least one genomic region of the wild-type virus with a region with increased CpG di-nucleotide encoding a similar protein sequence, wherein in the increase of the CpG di-nucleotide is at least 41 instances above the parent, or at least 21 instances above the parent viral genome, (4) a modified virus derived from a wild-type virus or a previously modified virus, by substituting at least one genomic region of the wild-type virus with a region with increased UpA di-nucleotide encoding a similar protein sequence, wherein in the increase of the UpA di-nucleotide is at least 26 instances above the parent, or at least 13 instances above the parent viral genome, (5) a modified virus derived from a wild-type virus or a previously modified virus, by substituting at least one genomic region of the wild-type virus with a region with increased UpA and the CpG di-nucleotide encoding a similar protein sequence, wherein in the increase of the UpA and the CpG di-nucleotide was at least 42 instances combined above the parent, or (6) combinations thereof.

In various embodiments, the prime dose is administered subcutaneously, intramuscularly, intradermally, intranasally or intravenously.

In various embodiments, the one or more boost dose is administered intratumorally, intravenously, intrathecally or intraneoplastically (directly into the tumor). A preferred mode of administration is directly to the tumor site.

The timing between the prime and boost dosages can vary, for example, depending on the type of cancer, the stage of cancer, and the patient's health. In various embodiments, the first of the one or more boost dose is administered about 2 weeks after the prime dose. That is, the prime dose is administered and about two weeks thereafter, the boost dose is administered.

In various embodiments, the one or more boost dose is administered about 2 weeks after a prime dose. In various embodiments, 2, 3, 4, or 5 boost doses are administered. In various embodiments, the intervals between the boost doses can be 1, 2, 3, 4, 5, 6, 7, 8, 9, or 10 weeks. In additional embodiments, the intervals between the boost doses can be 1, 2, 3, 4, 5, 6, 7, 8, 9, 10, 11 or 12 months. As a non-limiting example, the prime dose can be administered, about two weeks thereafter a first boost dose can be administered, about one month after the first boost dose, a second boost dose can be administered, about 6 months after the second boost dose, a third boost dose can be administered. As another non-limiting example, the prime dose can be administered, about two weeks thereafter a first boost dose can be administered, about six months after the first boost dose, a second boost dose can be administered, about 12 months after the second boost dose, a third boost dose can be administered. In further embodiments, additional boost dosages can be periodically administered; for example, every year, every other year, every 5 years, every 10 years, etc.

In various embodiments, the dosage amount can vary between the prime and boost dosages. As a non-limiting example, the prime dose can contain fewer copies of the virus compare to the boost dose.

In other embodiments, the type of attenuated virus produced by a method other than codon-pair deoptimization or modified virus of the present invention can vary between the prime and boost dosages. In one non-limiting example, a modified virus of the present invention can be used in the prime dose and an attenuated virus (produced by a method other than codon-pair deoptimization) of the same or different family, genus, species, group or order can be used in the boost dose.

In other embodiments, the type of attenuated virus produced by a method other than codon-pair deoptimization or modified virus of the present invention can also be utilized as the prime and boost dosages. In one non-limiting example, an attenuated virus can be used in the prime dose and an attenuated virus (produced by a method other than codon-pair deoptimization) of the same or different family, genus, species, group or order can be used in the boost dose.

Examples of other attenuated viruses that can also be utilized as the prime and/or boost dosages includes family and all related genera, strains, types and isolates of viruses described herein (e.g., in the "Viruses and Modified Viruses" section above) as well as attenuated viruses belonging to the Picornaviridae virus family and all related genera, strains, types and isolates; attenuated viruses belonging to the Herpesviridae virus family and all related genera, strains; attenuated viruses belonging to the Rhabdoviridae virus family and all related genera, strains, types and isolates; attenuated viruses belonging to the Reoviridae virus family and all related genera, strains; attenuated viruses belonging to the Poxviridae virus family and all related genera, strains; attenuated viruses belonging to the Togaviridae virus family and all related genera, strains.

In other embodiments, the route of administration can vary between the prime and the boost dose. In a non-limiting example, the prime dose can be administered subcutaneously, and the boost dose can be administered via injection into the tumor; for tumors that are in accessible, or are difficult to access, the boost dose can be administered intravenously.

In various embodiments, the treatment further comprises administering a PD-1 inhibitor. In other embodiments, the treatment further comprises administering a PD-L1 inhibitor. In still other embodiments, the treatment further comprises administering both an PD-1 inhibitor and a PD-L1 inhibitor. In particular embodiments, the PD-1 inhibitor, the PD-L1 inhibitor, or both are administered during the treatment (boost) phase, and not during the priming phase.

In various embodiments, the PD-1 inhibitor is an anti-PD1 antibody. In various embodiments, the PD-L1 inhibitor is an anti-PD-L1 antibody. Examples of PD-1 inhibitors and PD-L1 inhibitors are provided herein.

Prime-Boost Treatment Before Having Cancer

Various embodiments of the present invention provide for a method of eliciting an immune response in a subject who does not have cancer and inducing an oncolytic effect on a tumor or cancer cell if and when the tumor or cancer cell develops in the subject. The method uses a prime-boost-type treatment regimen. In various embodiments, eliciting the immune response and inducing an oncolytic effect on the tumor or cancer cell results in treating a malignant tumor if and when the subject develops cancer.

A prime dose of an attenuated virus or a modified virus of the present invention is administered to elicit an initial immune response when the subject does not have cancer or when the subject is not believed to have cancer. The latter may be due to undetectable or undetected cancer.

A prime dose of an attenuated virus can be an attenuated virus produced by a method other than codon-pair deoptimization or a modified virus of the present invention can also be utilized as the prime and boost dosage when the subject does not have cancer or when the subject is not believed to have cancer. Again, the latter may be due to undetectable or undetected cancer.

Thereafter, in some embodiments, a boost dose of an attenuated virus or a modified virus of the present invention is administered periodically to continue to elicit the immune response. For example, a boost dose can be administered about every 1, 2, 3, 4, 5, 6, 7, 8, 9, or 10 years. In particular embodiments, the boost dose can be administered about every 5 years.

Alternatively, in other embodiments, a boost dose of an attenuated virus or a modified virus of the present invention is administered after the subject is diagnosed with cancer. For example, once the subject is diagnosed with cancer, a treatment regimen involving the administration of a boost dose can be started shortly thereafter to induce oncolytic effects on the tumor and/or to elicit an immune response comprising an oncolytic effect against the tumor. In further embodiments, additional boost doses can be administered to continue to treat the cancer.

While not wishing to be bound by any particular theory, or set regimen, it is believed that the prime dose and boost dose(s) "teach" the subject's immune system to recognize virus-infected cells. Thus, when the subject develops cancer and the boost dose is administered, the subject's immune system recognizes the virus infected cells; this time, the virus infected cells are the cancer cells. During the immune response to the virus infected cancer cells, the immune system is also primed with cancer antigens, and thus enhances the anti-cancer immunity as the immune system will also target the cells expressing the cancer antigens.

As such, in various embodiments, the treatment of the malignant tumor decreases the likelihood of recurrence of the malignant tumor. It can also decrease the likelihood of having a second cancer that is different from the malignant tumor. If the subject develops a second cancer that is different from the malignant tumor and the treatment of the malignant tumor results in slowing the growth of the second cancer. In some embodiments, after remission of the malignant tumor, the subject develops a second cancer that is different from the malignant tumor and the treatment of the malignant tumor results in slowing the growth of the second cancer.

One can think of the prime and boost doses as an anti-cancer vaccine, preparing the immune system to target treated tumor cells when cancer develops.

In various embodiments, the prime dose and the boost dose contains the same attenuated virus or modified virus of the present invention. In other embodiments, the prime dose and the boost does are different attenuated viruses or modified viruses of the present invention.

In various embodiments, the method comprises administering a prime dose of a modified virus to a subject in need thereof; and administering one or more boost dose of a modified virus to the subject in need thereof, wherein the prime dose and boost dose of the modified virus are each independently selected from (1) an attenuated virus produced by a method other than codon-pair deoptimization, (2) a modified virus derived from a wild-type virus or a previously modified virus, by substituting at least one genomic region of the wild-type virus with a codon-pair deoptimized region encoding a similar protein sequence, wherein the codon pair bias of the modified sequence is less than the codon pair bias of the parent virus, and is reduced by at least about 0.05, or at least about 0.1, or at least about 0.2, (3) a modified virus derived from a wild-type virus or a previously modified virus, by substituting at least one genomic region of the wild-type virus with a region with increased CpG di-nucleotide encoding a similar protein sequence, wherein in the increase of the CpG di-nucleotide is at least 41 instances above the parent, or at least 21 instances above the parent viral genome, (4) a modified virus derived from a wild-type virus or a previously modified virus, by substituting at least one genomic region of the wild-type virus with a region with increased UpA di-nucleotide encoding a similar protein sequence, wherein in the increase of the UpA di-nucleotide is at least 26 instances above the parent, or at least 13 instances above the parent viral genome, (5) a modified virus derived from a wild-type virus or a previously modified virus, by substituting at least one genomic region of the wild-type virus with a region with increased UpA and the CpG di-nucleotide encoding a similar protein sequence, wherein in the increase of the UpA and the CpG di-nucleotide was at least 42 instances combined above the parent, or (6) combinations thereof.

In various embodiments, the prime dose is administered subcutaneously, intramuscularly, intradermally, intranasally or intravenously.

In various embodiments, the one or more boost dose, when it is administered to a subject who does not have cancer, or is not suspected to have cancer, it is administered subcutaneously, intramuscularly, intradermally, intranasally or intravenously.

In various embodiments, the one or more boost dose, when it is administered to a subject who had been diagnosed with cancer, it is administered intratumorally, intravenously, intrathecally or intraneoplastically (directly into the tumor). A preferred mode of administration is directly to the tumor site.

The timing between the prime and boost dosages can vary, for example, depending on the type of cancer, the stage of cancer, and the patient's health. In various embodiments, the first of the one or more boost dose is administered about every 1, 2, 3, 4, 5, 6, 7, 8, 9, or 10 years after the prime dose, if the subject does not have cancer or is not suspected to have cancer. In particular embodiments, the boost dose is administered about every 5 years.

In various embodiments, for example, when the subject is diagnosed with cancer the one or more boost dose is administered after the diagnosis of cancer. In various embodiments, 2, 3, 4, or 5 boost doses are administered. In various embodiments, the intervals between the boost doses can be 1, 2, 3, 4, 5, 6, 7, 8, 9, or 10 weeks. In additional embodiments, the intervals between the boost doses can be 1, 2, 3, 4, 5, 6, 7, 8, 9, 10, 11 or 12 months. As a non-limiting example, the prime dose can be administered, about five years thereafter, a first boost dose can be administered, about one year after the first boost dose, the subject is diagnosed with cancer, and a second boost dose can be administered, about 2 weeks after the second boost dose, a third boost dose can be administered, about 2 weeks after the third boost dose, a fourth boost dose can be administered, and about 1 month after the fourth boost dose a fifth boost dose can be administered. Once the cancer is determined to be in remission, additional periodic boost doses can be administered; for example, every 6 months, every year, every 2, years, every 3, years, every 4 years or every 5 years.

In various embodiments, the dosage amount can vary between the prime and boost dosages. As a non-limiting example, the prime dose can contain fewer copies of the virus compare to the boost dose.

In other embodiments, the type of attenuated virus produced by a method other than codon-pair deoptimization or modified virus of the present invention can vary between the prime and boost dosages. In one non-limiting example, a modified virus of the present invention can be used in the prime dose and an attenuated virus (produced by a method other than codon-pair deoptimization) of the same or different family, genus, species, group or order can be used in the boost dose.

Examples of other attenuated viruses that can also be utilized as the prime and/or boost dosages includes family and all related genera, strains, types and isolates of viruses described herein (e.g., in the "Viruses and Modified Viruses" section above) as well as attenuated viruses belonging to the Picornaviridae virus family and all related genera, strains, types and isolates; attenuated viruses belonging to the Herpesviridae virus family and all related genera, strains; attenuated viruses belonging to the Rhabdoviridae virus family and all related genera, strains, types and isolates; attenuated viruses belonging to the Reoviridae virus family and all related genera, strains; attenuated viruses belonging to the Poxviridae virus family and all related genera, strains; attenuated viruses belonging to the Togaviridae virus family and all related genera, strains.

In other embodiments, the route of administration can vary between the prime and the boost dose. In a non-limiting example, the prime dose can be administered subcutaneously, and the boost dose can be administered via injection into the tumor; for tumors that are in accessible, or are difficult to access, the boost dose can be administered intravenously.

In various embodiments, subjects that receive these treatments (e.g., prime dose before having cancer, or prime and boost doses before having cancer, and then followed by boost doses after having cancer) can be a subject who are at a higher risk of developing cancer. Examples of such subject include but are not limited to, subjects with genetic dispositions (e.g., BRCA1 or BRCA2 mutation, TP53 mutations, PTEN mutations, KRAS mutations, c-Myc mutations, any mutation deemed by the National Cancer institute as a cancer-predisposing mutation, etc.), family history of cancer, advanced age (e.g., 40, 45, 55, 65 years or older), higher than normal radiation exposure, prolonged sun exposure, history of tobacco use (e.g., smoking, chewing), history of alcohol abuse, history of drug abuse, a body mass index>25, history of a chronic inflammatory disease(s) (e.g., inflammatory bowel diseases, ulcerative colitis, Crohn disease, asthma, rheumatoid arthritis, etc.), history of immune suppression, history of chronic infections known to have a correlation to increased cancer risk (e.g., Hepatitis C, Hepatitis B, EBV, CMV, HPV, HIV, HTLV-1, MCPyV, *H. Pylori*, etc.).

In various embodiments, subjects that receive these treatments (e.g., prime dose and boost dose before having cancer, or prime and boost doses before having cancer, and then followed by boost doses after having cancer) can be subjects who do not fall into the higher risk category but are prescribed the prime and boost doses by their clinician as a preventive measure for future cancer risk.

In various embodiments, the treatment further comprises administering a PD-1 inhibitor. In other embodiments, the treatment further comprises administering a PD-L1 inhibitor. In still other embodiments, the treatment further comprises administering both an PD-1 inhibitor and a PD-L1 inhibitor. In particular embodiments, the PD-1 inhibitor, the PD-L1 inhibitor, or both are administered during the treatment (boost) phase, and not during the priming phase.

In various embodiments, the PD-1 inhibitor is an anti-PD1 antibody. In various embodiments, the PD-L1 inhibitor is an anti-PD-L1 antibody. Examples of PD-1 inhibitors and PD-L1 inhibitors are provided herein.

Inflammatory Response

The administration of the modified viruses of the present invention stimulate IL-1B. While not wishing to be bound by any particular theory, the modified viruses of the present invention provide for stimulation of RIG-I, STNG, IRF3, IRF7, and NFkB, which promote a sustained inflammatory response and provide, in part, the therapeutic efficacy.

In various embodiments, the administration of the modified viruses of the present invention to stimulate endogenous IL-1B production in the subject. While not wishing to be bound by any particular theory, the modified viruses of the present invention provide for stimulation of innate immune receptors RIG-I and STNG, which stimulates and promotes a sustained inflammatory response and provide, in part, the therapeutic efficacy.

In various embodiments the administration of the modified viruses of the present invention to stimulate endogenous IL-1B production in the subject. While not wishing to be bound by any particular theory, the modified viruses of the present invention provide for stimulation of innate immune transcription factors IRF3, IRF7, and NFkappaB, which stimulates and promotes a sustained inflammatory response and provide, in part, the therapeutic efficacy.

In various embodiments the administration of the modified viruses of the present invention to maintain a therapeutically effective amount of IL-1B production in the subject to promote a sustained inflammatory response and provide, in part, the therapeutic efficacy.

In various embodiments, the administration of the modified viruses of the present invention to stimulate endogenous Type-1 interferon production in the subject which provides, in part, the therapeutic efficacy.

In various embodiments, the administration of the modified viruses of the present invention to maintain a therapeutically effective amount of Type-1 interferon production in the subject which provides, in part, the therapeutic efficacy.

In still other embodiments, the administration of the modified viruses of the present invention to activate of Type I Interferon in a subject to maintain ionizing radiation and chemotherapy sensitization in the subject.

In various embodiments the administration of the modified viruses of the present invention to recruit pro-inflammatory immune cells including CD45+ Leukocytes, Neutrophils, B-cells, CD4+ T-cells, and CD8+ immune cells to the site of cancer, which provides, in part, the therapeutic efficacy.

In various embodiments the administration of the modified viruses of the present invention to decrease anti-inflammatory immune cells such as FoxP3+ T-regulatory cells or M2-Macrophages from the site of cancer, which provides, in part, the therapeutic efficacy.

In various embodiments, the treatment of the malignant tumor decreases the likelihood of recurrence of the malignant tumor. It can also decrease the likelihood of having a second cancer that is different from the malignant tumor. If the subject develops a second cancer that is different from the malignant tumor and the treatment of the malignant tumor results in slowing the growth of the second cancer. In some embodiments, after remission of the malignant tumor, the subject develops a second cancer that is different from the malignant tumor and the treatment of the malignant tumor results in slowing the growth of the second cancer.

PD-1 Inhibitors and PD-L1 Inhibitors

Examples of anti-PD1 antibodies that can be used as discussed herein include but are not limited to pembrolizumab, nivolumab, pidilizumab, AMP-224, AMP-514, spartalizumab, cemiplimab, AK105, BCD-100, BI 754091, JS001, LZM009, MGA012, Sym021, TSR-042, MGD013, AK104, XmAb20717, and tislelizumab.

Additional examples of PD-1 inhibitors include but are not limited PF-06801591, anti-PD1 antibody expressing pluripotent killer T lymphocytes (PIK-PD-1), and autologous anti-EGFRvIII 4SCAR-IgT cells.

Examples of anti-PD-L1 antibody include but are not limited to BGB-A333, CK-301, FAZ053, KN035, MDX-1105, MSB2311, SHR-1316, atezolizumab, avelumab, durvalumab, BMS-936559, and CK-301. An additional example of an anti-PD-L1 inhibitor is M7824.

Routes of Administration

In additional to those discussed above, therapeutic oncolytic modified viruses can be delivered intratumorally, intravenously, intrathecally or intraneoplastically (directly into the tumor). A preferred mode of administration is directly to the tumor site. The inoculum of virus applied for therapeutic purposes can be administered in an exceedingly small volume ranging between 1-10 µl.

It will be apparent to those of skill in the art that the therapeutically effective amount of modified viral chimeras of this invention can depend upon the administration schedule, the unit dose of modified viral chimeras administered, whether the modified virus chimera is administered in combination with other therapeutic agents, the status and health of the patient.

The therapeutically effective amounts of oncolytic recombinant virus can be determined empirically and depend on the maximal amount of the recombinant virus that can be administered safely, and the minimal amount of the recombinant virus that produces efficient oncolysis.

Therapeutic inoculations of oncolytic modified viruses can be given repeatedly, depending upon the effect of the initial treatment regimen. Should the host's immune response to a particular oncolytic modified virus administered initially limit its effectiveness, additional injections of an oncolytic modified viruses with a different modified viruses' serotype can be made. The host's immune response to a particular modified virus can be easily determined serologically. It will be recognized, however, that lower or higher dosages than those indicated above according to the administration schedules selected.

For that purpose, serological data on the status of immunity against any given modified viruses can be used to make an informed decision on which variant of the modified viruses to be used. For example, if a high titer against modified viruses serotype 1 is evident through serological analysis of a candidate patient for treatment with oncolytic viruses, an alternate modified virus preparation should be used for tumor therapy.

TABLE 7

Sequences

| Name | Sequence | SEQ ID NO |
|---|---|---|
| PV-Min Y | ttaaaacagctctggggttgtacccacccagaggcccacgtggcggctagtactccggtattgcggtaccctt gtacgcctgttttatactcccttcccgtaacttagacgcacaaaaccaagttcaatagaagggggtacaaaccagt accaccacgaacaagcacttctgtttccccggtgatgtcgtatagactgcttgcgtggttgaaagcgacggatcc gttatccgcttatgtacttcgagaagcccagtaccacctcggaatcttcgatgcgttgcgctcagcactcaaccc agagtgtagcttaggctgatgagtctggacatccctcaccggtgacggtggtccaggctgcgttggcggcctac ctatggctaacgccatgggacgctagttgtgaacaaggtgtgaagagcctattgagctacataagaatcctccg gcccctgaatgcggctaatcccaacctcggagcaggtggtcacaaaccagtgattggcctgtcgtaacgcgca agtccgtggcggaaccgactactttgggtgtccgtgtttcctttttattttattgtggctgcttatggtgacaatcacag att TABLE 7-continued Sequences

| Name | Sequence | SEQ ID NO |
|---|---|---|
| | aggttttatacgctagacaccgtgtcttggacgaaagagtcgcgagggtggtggtggaagttgcctgatgcact gagggacatgggactctttgggcaaaatatgtactaccactacctaggtaggtccgggtacaccgtgcatgtac agtgtaacgcctccaaattccaccaggggcactaggggtattcgccgtaccagagatgtgtctggccgggga tagcaacaccactaccatgcacaccagctatcaaaatgccaatcctggcgagaaaggaggcactttcacgggt acgttcactcctgacaacaaccagacatcacctgcccgcaggttctgcccggtggattacctccttggaaatggc acgttgtttgggGAATGCCTTCGTATTCCCACACCAGATAATTAACTTACGG ACTAACAATTGCGCAACCCTAGTGTTGCCATACGTTAACTCACTGT CAATCGATAGTATGGTGAAACATAACAATTGGGGGATCGCAATATT ACCGTTAGCGCCACTGAATTTCGCCAGCGAATCGTCACCTGAGATA CCGATTACCCTTACAATCGCACCTATGTGTTGCGAGTTCAACGGAT TGCGTAATATAACCCTACCACGGTTGCAGGGGTTGCCCGTTATGAA TACCCCAGGGTCTAACCAATACCTTACCGCCGATAATTTCCAATCC CCTTGCGCACTGCCAGAGTTCGACGTAACCCCTCCAATCGACATAC CCGGCGAGGTTAAGAATATGATGGAGTTAGCCGAAATCGATACTA TGATACCGTTCGATCTATCCGCTACGAAAAGAATACTATGGAGAT GTATCGCGTGAGATTGTCCGATAAGCCACATACCGACGATCCGATA CTGTGTCTGTCACTGTCACCCGCCAGCGATCCTAGGTTGTCCCATAC AATGTTAGGCGAGATACTGAATTACTATACCCATTGGGCCGGTAGT CTGAAATTCACATTTCTGTTTTGCGGATCTATGATGGCGACCGGAA AGCTGTTAGTGTCATACGCTCCACCCGGAGCCGATCCACCTAAAAA ACGCAAGGAAGCGATGCTCGGTACACACGTGATATGGGATATCGG ACTGCAATCGTCATGTACTATGGTCGTGCCATGGATATCGAATACG ACTTATAGACAGACAATCGACGATAGCTTTACCGAGGGGGGGTAT ATTAGCGTATTCTATCAGACACGTATCGTAGTGCCACTGTCAACCC CTAGAGAGATGGACATACTCGGATTCGTATCCGCATGTAACGACTT TAGCGTGAGACTGTTACGCGATACTACCCATATCGAACAGAAAGC Gctagcacaggggttaggtcagatgcttgaaagcatgattgacaacacagtccgtgaaacggtgggggcggc aacatctagagacgctctcccaaacactgaagccagtggaccaacacactccaaggaaattccggcactcacc gcagtggaaactggggccacaaatccactagtcccttctgatacagtgcaaaccagacatgttgtacaacatag gtcaaggtcagagtctagcatagagtctttcttcgcgcggggtgcatgcgtgaccattatgaccgtggataaccc agcttccaccacgaataaggataagctttttgcagtgtgaagatcacttataaagatactgtccagttacggagg aaattggagttcttcacctattctagatttgatatggaacttaccttgtggttactgcaaatttcactgagactaacaa tggccatgcattaaatcaagtgtaccaaattatgtacgtaccaggcgctccagtgcccgaaaaatgggacg actacacatggcaaacctcatcaaatccatcaatcttttacacctacgggacagctccagcccggatctcggtac cgtatgttggtatttcgaacgcctattcacacttttacgacggttttttccaaagtaccactgaaggaccagtcggca gcactaggtgactccctttatggtgcagcatctctaaatgacttcggtattttggctgttagagtagtcaatgatcac aacccgaccaaggtcacctccaaaatcagagtgtatctaaaaccaaacacatcagagtctctggtgcccgcgtcc accgagggcagtggcgtactacggccctggagtggattacaaggatggtacgcttacacccctctccaccaag gatctgaccacatggattcggacaccaaaacaaagcggtgtacactgcaggttacaaaatttgcaactacca cttggccactcaggatgatttgcaaaacgcagtaacgtcatgtggagtagagaccttagtcacagaatcaag agcccagggcaccgattcaatcgcaaggtgcaattgcaacgcagggggtgtactactgcgagtctagaaggaa atactacccagtatccttcgttggcccaacgttccagtacatggaggctaataactattaccccagctaggtaccag tcccatatgctcattggccatggattcgcatctcaggggattgtggtggcatactcagatgtcaccacggggtg ataggatcattactgctggtggagaaagggttggttgcattttcagacattagagacttgtatgcctacgaagaag aagccatggacaaggcctcaccaattacatagagtcacttggggcgccatttggaagtggatttactcagcag attagcgacaaaataacagagttgaccaatatggtgaccagtaccatcactgaaaagctacttaagaacttgatc aagatcatatcctcactagttattataactaggaactatgaagacaccacaacagtgctcgctaccctggcccttct tgggtgtgatgcttcaccatggcagtggcttagaaagaaagcatgcgatgttctggagataccttatgtcatcaag caaggtgcagttggttgaagaagtttactgaagcatgcaagcagctaagggactggagtgggtgtcaaaca aaatctcaaattcattgattggctcaaggagaaaattatcccacaagctagagataagttggaatttgtaacaaa acttagacaactagaaatgctggaaaaccaaatctcaactatacaccaatcatgcccctagtcaggaacaccagg aaattctattcaataatgtcagatggttatccatccagtctaagaggtttgcccctcttttacgcagtggaagccaaa agaatacagaaactcgagcatactattaacaactacatacagttcaagagcaaacaccgtattgaaccagtatgtt tgctagtacatggcagccccggaacaggtaaatctgtagcaaaccaacctgattgctagagccatagctgaaaga gaaaacacgtccacgtactcgctaccccggatccatcacactcgacggatacaaacaacagggagtggtga ttatggacgacctgaatcaaaacccagatggtgcggacatgaagctgttctgtcagatggtatcaacagtggagt ttataccacccatggcatccctggaggagaaaggaatcctgtttacttcaaattacgttctagcatccacaaactca agcagaatttccccccccactgtggcacacagtgacgcgttagccaggcgctttgcgttcgacatggacattca ggtcatgaatgagtattctagagatgggaaattgaacatggcatggctactgaaatgtgtaagaactgtcacca accagcaaactttaagagatgctgtcctttagtgtgtggtaaggcaatttcaattaatgacaaatcttccagagtta gatacagtattgaccagatcactacaatgattatcaatgagagaaacagaagatccaacattggcaattgtatgg aggctttgtttcaaggaccactccagtataaagacttgaaaattgacatcaaggacagctcccctcctgaatgtat caatgacttgctccaagcagttgactcccaggaggtgagagttactgtgagaagaagggttggatagttaacat caccagccaggttcaaacagaaaggaacatcaacagggcaatgacaattctacaagcggtgacaaccttcgc cgcagtggctggagttgtctatgtcatgtataaactgtttgctggacaccagggagcatacactggtttaccaaac aaaaaaccaacgtgcccaccattcggacagcaaaggtaacagcaaaggttcgattacgcagtggctatg gctaaaagaaacattgttacagcaactactagcaaggagagttcactatgttaggagtccacgacaacggc tattttaccaacccacgcttcacctggtgaaagcattgtgatcgatggcaaagaagtggagatcttggatgccaa agcgctcgaagatcaagcaggaaccaatcttgaaatcactataatcactctaaagagaaatgaaaagttcagag acattagacacattacctactcaaatcactgagacaaatgtggactcttgatcgtgaacactagcaagtacc ccaatatgtatgttcctcggtgctgtgactgaacagggatatggtaaatctcggtgggcgccaaactgctcgtac tctaatgtcaacttttccaaccagagcaggacagtgtggtggagtcatcacatgtactgggaaagtcatcggat gcatgttggtgggaacggttcacacgggtttgcagcggccctgaagcgatcatacttcactcagagtcaaggtg aaatccagtggatgagaccttcgaaggaagtgggatatccaatcataaatgccccgtccaaaaccaagcttgaa cccagtgctttccactatgtgtttgaaggggtgaaggaaccagcagtcctcactaaaaacgatcccaggcttaag | |

TABLE 7-continued

Sequences

| Name | Sequence | SEQ ID NO |
|---|---|---|
| | acagactttgaggaggcaatttttctccaagtacgtgggtaacaaaattactgaagtggatgagtacatgaaagag gcagtagaccactatgctggccagctcatgtcactagacatcaacatagaacaaatgtgcttggaggatgccat gtatggcactgatggtctagaagcacttgatttgtccaccagtgctggctacccttatgtagcaatgggaaagaa gaagagagacatcttgaacaaacaaaccagagacactaaggaaatgcaaaaactgctcgacacatatggaatc aacctcccactggtgacttatgtaaaggatgaacttagatccaaaacaaaggttgagcaggggaaatccagatt aattgaagcttctagtttgaatgactcagtggcaatgagaatggcttttgggaacctatatgctgcttttcacaaaaa cccaggagtgataacaggttcagcagtggggtgcgatccagatttgttttggagcaaaattccggtattgatgga agagaagctgtttgcttttgactacacagggtatgatgcatctctcagccctgcttggttcgaggcactaaagatg gtgcttgagaaaatcggattcggagacagagttgactacatcgactacctaaaccactcacaccacctgtacaa gaataaaacatactgtgtcaagggcggtatgccatctggctgctcaggcacttcaattttttaactcaatgattaaca acttgattatcaggacactcttactgaaaacctacaagggcatagatttagaccacctaaaaatgattgcctatggt gatgatgtaattgcttcctaccccatgaagttgacgctagtctcctagcccaatcaggaaaagactatggactaa ctatgactccagctgacaaatcagctacatttgaaacagtcacatgggagaatgtaacattcttgaagagattcttc agggcagacgagaaatacccatttcttattcatccagtaatgccaatgaaggaaattcatgaatcaattagatgga caaaagatcctaggaacactcaggatcacgttcgctctctgtgccttttagcttggcacaatggcgaagaagaat ataacaaattcctagctaaaatcaggagtgtgccaattgaagagctttattgctcccagagtactcaacattgtac cgccgttggcttgactcattttagtaaccctacctcagtcgaattggattgggtcatactgTtgtaggggtaaatttt tctttaattcggag | |
| Zika E-Min (MR766 E-Min) | AGTTGTTGATCTGTGTGAGTCAGACTGCGACAGTTCGAGTCTGAAG CGAGAGCTAACAACAGTATCAACAGGTTTAATTTGGATTTGGAAAC GAGAGTTTCTGGTCATGAAAAACCCAAAGAAGAAATCCGGAGGAT TCCGGATTGTCAATATGCTAAAACGCGGAGTAGCCCGTGTAAACCC CTTGGGAGGTTTGAAGAGGTTGCCAGCCGGACTTCTGCTGGGTCAT GGACCCATCAGAATGGTTTTGGCGATACTAGCCTTTTTGAGATTTA CAGCAATCAAGCCATCACTGGGCCTTATCAACAGATGGGGTTCCGT GGGGAAAAAGAGGCTATGGAAATAATAAAGAAGTTCAAGAAAG ATCTTGCTGCCATGTTGAGAATAATCAATGCTAGGAAAGAGAGGA AGAGACGTGGCGCAGACACCAGCATCGGAATCATTGGCCTCCTGCT GACTACAGCCATGGCAGCCGAAATTACGAGAAGGGGGTCCGCATA CTATATGTATCTGGATAGGTCCGACGCCGGTAAGGCAATCTCATTC GCAACGACACTCGGAGTGAATAAGTGTCACGTTCAGATTATGGACT TAGGGCATATGTGCGACGCTACTATGTCATACGAATGCCCTATGCT TGACGAAGGCGTTGAGCCAGACGACGTCGACTGTTGGTGCAATAC GACTAGCACATGGGTCGTGTACGGTACATGCCATCACAAAAAGGG CGAAGCGAGACGGTCTAGAAGGGCCGTTACGTTGCCGTCACACTCT ACGAGAAAGTTGCAGACTAGGTCTCAGACTTGGTTGGAGTCACGC GAATACACTAAGCATCTGATTAAGGTCGAGAATTGGATTTTTAGGA ACCCAGGGTTCGCACTAGTCGCCGTCGCAATCGCTTGGTTGTTGGG GTCTAGTACGAGTCAGAAAGTGATATACTTAGTGATGATACTGTTG ATCGCACCCGCATACTCTATTAGGTGTATCGGAGTGAGTAATCGCG ATTTCGTCGAGGGTATGAGCGGAGGGACATGGGTCGACGTTGTGCT TGAGCACGGGGGTGCGTTACCGTTATGGCCCAAGACAAACCGAC AGTCGATATCGAACTGGTTACGACTACCGTTTCGAACATGGCCGAA GTGAGATCGTATTGTTACGAGGCTAGCATAAGCGATATGGCTAGCG ATAGTAGGTGCCCAACACAGGGCGAAGCGTATCTCGATAAGCAAT CCGATACGCAATACGTTTGCAAACGGACATTGGTCGATAGGGGGT GGGGTAACGGATGCGGACTGTTCGGTAAGGGGTCACTAGTGACAT GCGCTAAGTTTACATGCTCTAAAAAAATGACCGGTAAGTCAATCCA ACCCGAAAACCTTGAGTATAGGATTATGTTGAGCGTACACGGATCG CAACACTCCGGTATGATCGTTAACGATACCGGATACGAGACTGACG AGAATAGGGCTAAGGTCGAGGTGACACCTAACTCACCTAGAGCCG AAGCGACATTGGGGGGGTTCGGATCTCTCGGACTGGATTGCGAACC TAGAACCGGATTGGACTTTAGCGATCTGTACTATCTGACTATGAAC AATAAGCATTGGTTGTGCATAAGGAGTGGTTTCACGACATACCAC TGCCATGGCACGCCGGAGCCGATACCGGTACGCCACATTGGAATA ACAAAGAGGCACTAGTCGAGTTTAAGGACGCTCACGCTAAGAGAC AGACCGTAGTCGTGTTGGGGTCACAGGAGGGAGCCGTGCATACCG CACTAGCCGGCGCACTCGAGGCCGAAATGGACGGAGCGAAAGGGA GACTGTTTAGCGGACACCTTAAGTGTAGACTGAAAATGGACAAGTT GCGACTTAAGGGCGTTAGCTATAGCCTATGTACCGCCGCATTTACG TTTACGAAAGTGCCAGCCGAAACGTTGCACGGAACCGTTACCTCG AGGTGCAATACGCCGGAACCGACGGACCATGCAAGATACCCGTGC AAATGGCCGTCGATATGCAGACACTGACACCAGTCGGACGGTTGA TTACCGCTAACCCAGTGATAACCGAGTCAACCGAAAACTCTAAGAT GATGCTCGAGCTTGACCCCACCATTCGGCGACTCATATATCGTTATC GGAGTCGGCGACAAAAAGATTACGCATCATTGGCATAGATCCGGA TCGACAATCGGTAAGGCATTCGAAGCGACAGTGAGAGGCGCTAAG CGTATGGCCGTATTGGGCGATACCGCATGGGACTTCGGATCCGTCG GCGGAGTGTTTAACTCACTCGGTAAGGGGATACACCAGATATTCGG AGCCGCATTCAAATCGTTGTTCGGCGGAATGTCATGGTTTAGTCAG ATACTGATCGGAACACTGCTTGTGTGGTTGGGGTTGAACACTAAGA ACGGATCGATTAGTCTGACATGCTTAGCCTTAGGCGGAGTGATGAT TTTTCTGTCAACCGCCGTTAGCGCAGACGTGGGGTGCTCAGTGGACt ctcaaaaaaggaaacgagatgtggcacgggggtattcatctataatgatgttgaagcctggagggaccggtac | 2 |

TABLE 7-continued

Sequences

| Name | Sequence | SEQ ID NO |
|---|---|---|
| | aagtaccatcctgactcccccgcagattggcagcagcagtcaagcaggcctgggaagaggggatctgtggg<br>atctcatccgtttcaagaatggaaaacatcatgtggaaatcagtagaaggggagctcaatgctatcctagaggag<br>aatggagttcaactgacagttgttgtgggatctgtaaaaaacccatgtggagaggtccacaaagattgccagtg<br>cctgtgaatgagctgccccatggctggaaagcctgggggaaatcgtattttgttagggcggcaaagaccaaca<br>acagttttgttgtcgacggtgacacactgaaggaatgtccgcttgagcacagagcatggaatagttttcttgtgga<br>ggatcacggggtttggagtcttccacaccagtgtctggcttaaggtcagagaagattactcattagaatgtgaccca<br>gccgtcataggaacagctgttaagggaagggaggccgcgcacagtgatctgggctattggattgaaagtgaaa<br>agaatgacacatggaggctgaagagggcccacctgattgagatgaaaacatgtgaatggccaaagtctcacac<br>attgtggacagatggagtagaagaaagtgatcttatcatacccaagtcttttagctggtccactcagccaccacaa<br>caccagagagggttacagaacccaagtgaaagggccatggcacagtgaagaActtgaaatccggtttgagg<br>aatgtccaggcaccaaggtttacgtggaggagacatgcgaactagaggaccatctctgagatcaactactgc<br>aagtgaaagggtcattgaggaatggctgtgtagggaatgcacaatgcccccactatcgttttcgagcaaaagac<br>ggctgctggtatggaatggagataaggcccaggaaagaaccagagagcaacttagtgaggtcaatggtgaca<br>gcggggtcaaccgatcatatggaccacttctctcttggagtgcttgtgattctactcatggtgcaggaggggttga<br>agaagagaatgaccacaaagatcatcatgagcacatcaatggcagtgctggtagtcatgatcttggggaggatttt<br>caatgagtgacctggccaagcttgtgatcctgatgggtgctactttcgcagaaatgaacactggagggagatgta<br>gctcacttggcattggtagcggcatttaaagtcagaccagcctctgctggtGtccttcattttcagagccaattgga<br>cacccgtgagagcatgctgctagccctggcttcgtgtcttctgcaaactgcgatctctgctcttgaaggtgactt<br>gatggtcctcattaatggatttgctttggcctggttggcaattcgagcaatggccgtgccacgcactgacaacatc<br>gctctaccaatcttggctgctctaacaccactagctcgaggcacactgctcgtggcatggaggagcgggcctggc<br>tacttgtggagggatcatgctcctctccctgaaagggaaaggtagtgtgaagaagaacctgccatttgtcatggc<br>cctgggattgacagctgtgagggtagtagaccctattaatgtggtaggactactgttactcacaaggagtgggaa<br>gcggagctggccccctagtgaagttctcacagccgttggcctgatatgtgcactggccgagggtttgccaag<br>gcagacattgagatggctggacccatcggctgcagtaggcttgctaattgtcagctatgtggtGtcgggaaagag<br>tgtggacatgtacattgaaagagcaggAgacatcactgggaaaagtc<br>ctcggcttgacgtggcactggatgagagtggtgatttctccttggtagaggaagatggtccacccatgagagag<br>atcatactcaaggtggtcctgatggccatctgtggcatgaacccaatagctataccttttgctgcaggagcgtggt<br>atgtgtatgtgaagactgggaaaaggagtggcgccctctgggacgtgcctgctcccaaagaagtgaagaaag<br>gagaAaccacagatggagtgtacagagtgatgactcgcagactgctaggttcaacacaggttggagtgggag<br>tcatgcaagaggggagtcttccacaccatgtggcacgttacaaaaggagccgcactgaggagcggtgagggaa<br>gacttgatccatactgggggatgtcaagcaggacttggtgtcatactgtgggccttggaagttggatgcagctt<br>gggatggactcagcgaggtacagcttttggccgtacctcccggagagagggccagaaacattcagaccctgc<br>ctgaaatattcaagacaaaggacggggacatcggagcagttgctctgaactaccctgcagggaccctcaggatc<br>tccgatcctagacaaatgtggaagagtgataggactctatgcaatggggttgtgatcaagaatggaagctatgt<br>tagtgctataacccagggaaagagggaggaggagactccggttgaatgtttcgaaccctcgatgctgaagaag<br>aagcagctaactgtcttggatctgcatccaggagccggaaaaaccaggagagttcttcctgaaatagtccgtga<br>agccataaaaaagagactccggacagtgatcttggccaccaactaggttgtcgctgctgagatgaggaggcc<br>ttgagaggacttccggtgcgttacatgacaacagcagtcaacgtcacccattctgggacagaaatcgttgatttg<br>atgtgccatgccactttcacttcacgcttactacaacccatcagagtccctaattacaatctcAacatcatggatga<br>agcccacttcacagacccctcaagtatagctgcaagaggatacatatcaacaaggggttgaaatgggcgaggcg<br>gctgccattttttatgactgccacaccaccaggaacccgtgatgcgtttctgactctaactccaccaatcatggaca<br>cagaagtggaagtcccagagagagcctggagctcaggctttgattgggtgacagaccattctgggaaaacagt<br>ttggttcgttccaagcgtgagaaacggaaatgaaatcgcagcctgtctgacaaaggctggaaagcgggtcata<br>cagctcagcaggaagacttttgagacagaatttcagaaaacaaaaaatcaagagtgggactttgtcataacaact<br>gacatctcagagatgggcgccaacttcaaggctgaccgggtcatagactctaggagatgcctaaaaccagtca<br>tacttgatggtgagagagtcatcttggctgggcccatgcctgtcacgcatgctagtgctgctcagagagagga<br>cgtataggcaggaaccctaacaaacctggagatgagtacatgtatggaggtgggtgtgcagagactgatgaag<br>gccatgcacactggcttgaagcaagaatgcttcttgacaacatctacctccaggatggcctcatagcctcgctct<br>atcggcctgaggccgataaggtagccgccattgagggagagttaagctgaggacagagcaaaggaagacct<br>tcgtggaactcatgaagagaggGgaccttcccgtctggctagccatcaggttgcatctgccgaataacttac<br>acagacagaagatggtgctttgatggcacaaccaacaacaccataatggaagacagcgtaccagcagaggtg<br>tggacaaagtatggagagaagagtgctcaaaccgagatggatggatgctagggtctgttcagaccatgcgg<br>ccctgaagtcgttcaaagaattcgccgctggaaaaagaggagcggctttgggagtaatggaggccctgggaa<br>cactgccaggacacatgacagaggtttcaggaagccattgacaacctcgccgtgctcatgcgagcagaga<br>ctggaagcaggcctataaggcagcggcagcccaactgccggagacTctagagacAattatgctcttaggttt<br>gctgggaacagtttcactggggatcttcttcgtcttgatgcggaataagggcatcggaagatgggctttggaat<br>ggtaacccttggggccagtgcatggctcatgtggctttcggaaattgaaccagccagaattgcatgtgtcctcatt<br>gttgtgtttttattactggtggtgctcataccgagccagagaagcaaagatctcccaagataaccagatggca<br>attatcatcatgtggcagtgggccttctaggtttgataactgcaaacgaacttggatggctggaaagaacaaaa<br>aatgacatagctcatcaatgggaaggagaagaaggagcaaccatgggattctcaatggacattgatctgcg<br>gccagcctccgcctgggctatctatgccgcattgacaactctcatcaccccagctgtccaacatgcggtaacca<br>cttcatacaacaactactccttaatggcgatggccacaagctggagtgctgtttggcatggcgaggaagacct<br>ccattttatgcatgggaccttggagtcccgctgctaatgatgggtgctattcacaattaacacccctgactctgata<br>gtagctatcattctgcttgtggcgcactacatgtacttgatcccaggcctacaagcggcagcagcgcgtgctgcc<br>cagaaaaggacagcagctggcatcatgaagaatcccgttgtggatggaatagtggtaactgacattgacacaat<br>gacaatagaccccaggtggaagaagaatgtggcacaagtgttactcatagcagtagccatctccagtgctgtg<br>ctgctgcggaccgcctgggatgggggaggctgagctctgatcacagcagcgacctccaccttgtgggaa<br>ggctctccaaacaaatactggaactcctctacagccacctcactgtgcaacatcttcagaggaagctatctggca<br>ggagcttcccttatctatacagtgacgagaaacgctggcctggttaagagacgtggaggtgggacgggagag<br>actctgggagagaagttggaaagctcgtctgaatcagatgtcggccctggagttctactcttataaaaagtcaggt<br>atcactgaagtgtgtagagaggaggctcgccgtgccctcaaggatggagtggccacaggaggacatgccgta<br>tcccggggaagtgcaaagctcagatggttggtggagagaggatatctgcagcccatgggaaggttgttgacct<br>cggatgtggcagagggggctggagctattatgccgccaccatccgcaaagtgcaggaggtgagaggataca<br>caaagggaggtccccggtcatgaagaacccatgctggtgcaaagctatgggtggaacatagttcgtctcaagag<br>tggagtggacgtcttccacatggccggctgagccgtgtgacactctgctgtgtgacataggtgagtcatcatctag | |

TABLE 7-continued

Sequences

| Name | Sequence | SEQ ID NO |
|---|---|---|
| | tcctgaagtggaagagacacgaacactcagagtgctctctatggtgggggactggcttgaaaaaagaccagg<br>ggccttctgtataaaggtgctgtgcccatacaccagcactatgatggaaaccatggagcgactgcaacgtaggc<br>atgggggaggattagtcagagtgccattgtctcgcaactccacacatgagatgtactgggtGtctggggcaaa<br>gagcaacatcataaaaagtgtgtccaccacaagtcagctcctcctgggacgcatggatggccccaggaggcc<br>agtgaaatatgaggaggatgtgaacctcggctcgggtacacgagctgtggcaagctgtgctgaggctcctaac<br>atgaaaatcatcggcaggcgcattgagagaatccgcaatgaacatgcagaaacatggttcttgatgaaaacca<br>cccatacaggacatgggcctaccatggagctacgaagcccccacgcaaggatcagcgtcttccctcgtgaa<br>cgggggttgttagactcctgtcaaagccttgggacgtggtgactggagttacaggaatagccatgactgacacca<br>caccatacggccaacaaagagtcttcaaagaaaaagtggacaccagggtgccagatccccaagaaggcactc<br>gccaggtaatgaacatagtctcttcctggctgtgaaggagctggggaaacgcaagcggccacgcgtctgca<br>ccaaagaagagtttatcaacaaggtgcgcagcaatgcagcactgggagcaatatttgaagaggaaaaagaatg<br>gaagacggctgtggaagctgtgaatgatccaaggttttgggccctagtggatagggagagaacaccacctg<br>agaggagagtgtcacagctgtgtgtacaacatgatgggaaaaagagaaaagaagcaaggagagttcgggaa<br>agcaaaaggtagccgcgccatctggtacatgtggttgggagccagattcttggagtttgaagcccttggattctt<br>gaacgaggaccattggatgggaagagaaaactcaggaggtggagtcgaagggttaggattgcaaagacttgg<br>atacattctagaagaaatgaatcgggcaccaggaggaaagatcacgcagatgacactgctggctgggacac<br>ccgcattagtaagtttgatctggagaatgaagctctgattaccaaccaaatggaggaagggcacagaactctgg<br>cgttggccgtgattaaatacacataccaaaacaaagtggtgaaggttctcagaccagctgaaggaggaaaaac<br>agttatggacatcattttcaagacaagaccagagagggagtggacaagttgtcacttatgctctcaacacattcac<br>caacttggtggtgcagcttatccggaacatgcaagctgaggaagtgcagatgcaagactatggttgttgag<br>gaagccagagaaaagtgaccagatggttgcagagcaatggatgggatagactcaaacgaatggcggtcagtg<br>gagatgactgcgttgtgaagccaatcgatgataggtttgcacatgccctcaggttcttgaatgacatggaaaag<br>ttaggaaagacacacaggagtggaaaccctcgactggatggagcaattgggaagaagtcccgttctgctccca<br>ccacttcaacaagctgtacctcaaggatgggagatccattgtggtcccttgccgccaccaagatgaactgattgg<br>ccgagctcgcgtctcaccaggggcaggatggagcatccgggagactgcctgtcttgcaaaatcatatgcgcag<br>atgtggcagctcctttatttcacagaagGgaccttcgactgatggctaatgccatttgctcggctgtgccagttg<br>actgggtTccaactgggagaaccacctggtcaatccatgaaagggagaatggatgaccactgaggacatgc<br>tcatggtgtggaatagagtgtggattgaggagaacgaccatatggaggacaagactcctgtaacaaaatggac<br>agacattccctatctaggaaaaagggaggacttatggtgtgaagtccccttataggggcacagacagccccgcaccactt<br>gggctgaaaacatcaaagacacagtcaacatggtgcgcaggatcataggtgatgaagaaaagtacatggacta<br>tctatccacccaagtccgctacttgggtgaggaagggtccacacccggagtgttgtaagcaccaattttagtgttg<br>tcaggcctgctagtcagccacagtttggggaaagctgtgcagcctgtaaccccccaggagaagctgggaaa<br>ccaagctcatagtcaggccgagaacgccatgcacgggaagaagccatgctgcctgctgagccctcagagga<br>cactgagtcaaaaaacccacgcgcttggaagcgcaggatgggaaaagaaggtggcgaccttccccacccctt<br>caatctgggccctgaactggagactagctgtgaatctccagcagagggactagtggttagaggagaccccccc<br>ggaaaacgcacaacagcatattgacgctgggaaagaccagagactccatgagtttccaccacgctggccgcc<br>aggcacagatcgccgaacTTCGGCGGCCGGTGTGGGGAAATCCATGGTTTCT | |
| Zika<br>E-W/Min<br>(MR766<br>E-W/Min) | AGTTGTTgatctgtgtgagtcagactgcgacagttcgagtctgaagcgagagctaacaacagtatcaaca<br>ggtttaatttggatttggaaacgagagtttctggtcatgaaaaacccaaagaagaaatccggaggattccggatt<br>gtcaatatgctaaaacgcggagtagcccgtgtaaacccctttggaggatttgccagccggacttct<br>gctgggtcatggaccocatcagaatgttttggcgatactagcctttttgagatttacagcaatcaagccatcactg<br>ggccttatcaacagatggggttccgtggggaaaaaagaggctatggaaataataaagaagttcaagaaagatct<br>tgctgccatgttgagaataatcaatgctaggaaagagaggaagagacgtggcgcagacaccagcatcggaat<br>cattggcctcctgctgactacagcccatggcagcagagatcactgacgcgggagtgcatactcatgtctacttgg<br>ataggagcgatgccggaaggccatttcgtttgctaccacattggggagtgaacaagtgccacgtacagatcatg<br>gacctcgggcacatgtgtgacgccaccatgagttatgagtgccctatgctggatgagggagtggaaccagatg<br>atgtcgattgctggtgcaacacgacatcaacttgggttgtgtacggaaccctgtcatcacaaaaaggtgaggca<br>cggcgatctagGagaaccgtgacgctccctctcactctacaaggaagttgcaaacgcggtcgcagacctggt<br>tagaatcaagagaatacacgaagcacttgatcaaggttgaaaactggatattcaggaaccccgggttttgcgcta<br>gtggccgttgccattgcctggcttttgggaagctcgacgagccaaaaagtcatatactttggtcatgatactgctga<br>ttgccccggcatacagtatcaggtgcattggagtcagcaatagagacttcgtggagggcatgtcaggtgggac<br>ctgggttgatgttgtcttgaacatggaggctgcgttaccgtgatggcacaggacaagccaacagttgacatag<br>agttggtcacgacgacggttagtaacatggccgaggtaagatcctattgctacgaggcatcgatatcggacatg<br>gcttcggacagtcgttgcccaacacaaggtgaagcctaccttgacaagcaatcagacactcaatatgtctgcaa<br>aagaacattagtggacagaggttggggaaacggttgtggactttttggcaaagggagcttggtgacatgtgcca<br>agtttacgtgttctaagaagatgaccggCaagagcattcaaccggaaaatctggagtatcggataatgctatca<br>gtgcatgctcccagcatagcgggatgattgtcaatgatacaggatatgtgaaactgacgaaaatagagcgaaagt<br>cgaggttacgCCTAACTCACCTAGAGCCGAAGCGACATTGGGGGGGTTC<br>GGATCTCTCGGACTGGATTGCGAACCTAGAACCGGATTGGACTTTA<br>GCGATCTGTACTATCTGACTATGAACAATAAGCATTGGTTGGTGCA<br>TAAGGAGTGGTTTCACGACATACCACTGCCATGGCACGCCGGAGCC<br>GATACCGGTACGCCACATTGGAATAACAAAGAGGCACTAGTCGAG<br>TTTAAGGACGCTCACGCTAAGAGACAGACCGTAGTCGTGTTGGGGT<br>CACAGGAGGGAGCCGTGCATACCGCACTAGCCGGCGCACTCGAGG<br>CCGAAATGGACGGAGCGAAAGGGAGACTGTTTAGCGGACACCTTA<br>AGTGTAGACTGAAAATGGACAAGTTGCGACTTAAGGGCGTTAGCT<br>ATAGCCTATGTACCGCCGCATTTACGTTTACGAAAGTGCCAGCCGA<br>AACGTTGCACGGAACCGTTACCGTCGAGGTGCAATACGCCGGAAC<br>CGACGGACCATGCAAGATACCCGTGCAAATGGCCGTCGATATGCA<br>GACACTGACACCAGTCGGACGGTTGATTACCGCTAACCCAGTGATA<br>ACCGAGTCAACCGAAAACTCTAAGATGATGCTCGAGCTTGACCCAC<br>CATTCGGCGACTCATATATCGTTATCGGAGTCGGCGACAAAAAGAT<br>TACGCATCATTGGCATAGATCCGGATCGACAATCGGTAAGGCATTC<br>GAAGCGACAGTGAGAGGCGCTAAGCGTATGGCCGTATTGGGCGAT | 3 |

TABLE 7-continued

Sequences

| Name | Sequence | SEQ ID NO |
|---|---|---|
| | ACCGCATGGGACTTCGGATCCGTCGGCGGAGTGTTTAACTCACTCG | |
| | GTAAGGGGATACACCAGATATTCGGAGCCGCATTCAAATCGTTGTT | |
| | CGGCGGAATGTCATGGTTTAGTCAGATACTGATCGGAACACTGCTT | |
| | GTGTGGTTGGGGTTGAACACTAAGAACGGATCGATTAGTCTGACAT | |
| | GCTTAGCCTTAGGCGGAGTGATGATTTTTCTGTCAACCGCCGTTAG | |
| | CGCAGACGTGGGGTGCTCAGTGGACTTCTCAAAAAAGGAAACGAG | |
| | ATGTGGCACGGGGGTATTCATCTATAATGATGTTGAAGCCTGGAGG | |
| | GACCGGTACAAGTACCATCCTGACTCCCCCCGCAGATTGGCAGCAG | |
| | CAGTCAAGCAGGCCTGGGAAGAGGGGATCTGTGGGATCTCATCCG | |
| | TTTCAAGAATGGAAAACATCATGTGGAAATCAGTAGAAGGGGAGC | |
| | TCAATGCTATCCTAGAGGAGAATGGAGTTCAACTGACAGTTGTTGT | |
| | GGGATCTGTAAAAAACCCCATGTGGAGAGGTCCACAAAGATTGCC | |
| | AGTGCCTGTGAATGAGCTGCCCCATGGCTGGAAAGCCTGGGGGAA | |
| | ATCGTATTTTGTTAGGGCGGCAAAGACCAACAACAGTTTTGTTGTC | |
| | GACGGTGACACACTGAAGGAATGTCCGCTTGAGCACAGAGCATGG | |
| | AATAGTTTTCTTGTGGAGGATCACGGGTTTGGAGTCTTCCACACCA | |
| | GTGTCtggcttaaggtcagagaagattactcattagaatgtgacccagccgtcataggaacagctgttaagg | |
| | gaagggaggccgcgcacagtgatctgggctattggattgaaagtgaaaagaatgacacatggaggctgaaga | |
| | gggcccacctgattgagatgaaaacatgtgaatggccaaagtctcacacattgtggacagatggagtagaaga | |
| | aagtgatcttatcatacccaagtcttttagctggtccactcagccaccacaacaccagagagggttacagaaccca | |
| | agtgaaagggccatggcacagtgaagaActtgaaatccggtttgaggaatgtccaggcaccaaggtttacgtg | |
| | gaggagacatgcggaactagaggaccatctctgagatcaactactgcaagtggaagggtcattgaggaatggt | |
| | gctgtagggaatgcacaatgcccccactatcgtttcgagcaaaagacggctgctggtatggaatggagataag | |
| | gcccaggaaagaaccagagagcaacttagtgaggtcaatggtgacagcggggtcaaccgatcatatgacca | |
| | cttctctcttggagtgcttgtgattctactcatggtgcaggaggggttgaagaagagaatgaccacaaagatcatc | |
| | atgagcacatcaatggcagtgctggtagtcatgatcttggaggattttcaatgagtgacctggccaagcttgtga | |
| | tcctgatgggtgctactttcgcagaaatgaacactggaggagatgtagctcacttggcattggtagcggcatttaa | |
| | agtcagaccagccttgctggtGtccttcattttcagagccaattggacacccgtgagagcatgctgctagccct | |
| | ggcttcgtgtcttctgcaaactgcgatctctgctcttgaaggtgacttgatggtcctcattaatggatttgctttggcc | |
| | tggttggcaattcgagcaatggccgtgccacgcactgacaacatcgctctaccaatcttggctgctctaacacca | |
| | ctagctcgaggcacactgctcgtggcatggagagcgggcctggctacttgtggagggatcatgctcctctccct | |
| | gaaagggaaggtagtgtgaagaagaacctgccatttgtcatggccctgggattgacagctgtgagggtagta | |
| | gaccctattaatgtggtaggactactgttactcacaaggagtgggaagcggagctggccccctagtgaagttctc | |
| | acagccgttggcctgatatgtgcactggccggagggtttgccaaggcagacattgagatggctggacccatgg | |
| | ctgcagtaggcttgctaattgtcagctatgtggtGtcgggaaagagtgtggacatgtacattgaaagagcagg | |
| | Agacatcacatgggaaaaggacgcggaagtcactggaaacagtcctcggcttgacgtggcactggatgaga | |
| | gtggtgatttctccttggtagaggaagatggtccacccatggaggagatcatactcaaggtggtcctgatggcca | |
| | tctgtggcatgaacccaatagctataccttttgctgcaggagcgtggtatgtgtatgtgaagactgggaaaagga | |
| | gtggcgccctctgggacgtgcctgctcccaaagaagtgaagaaaggagaAccacagatggagtgtacaga | |
| | gtgatgactcgcagactgctaggttcaacacaggttggagtgggagtcatgcaagagggagtcttccacaccat | |
| | gtggcacgttacaaaaggagccgcactgaggagcggtgagggaagacttgatccatactggggggatgtcaa | |
| | gcaggacttggtgtcatactgtgggccttggaagttggatgcagcttgggatggactcagcgaggtacagcttt | |
| | ggccgtacctcccgagagagggcagaaacattcagaccctgcctggaatattcaagacaaaggacggg | |
| | acatcggagcagttgctctggactaccctgcagggacctcaggatctccgatcctagacaaatgtggaagagtg | |
| | ataggactctatggcaatgggttgtgtcaagaatgtgaagatcgttgtatgcatataaccagggaaagaggga | |
| | ggaggagactccggttgaatgtttcgaaccctcgatgctgaagaagaagcagctaactgtcttggatctgcatcc | |
| | aggagccggaaaaaccaggagagttcttcctgaaatagtccgtgaagccataaaaaagagactccggacagt | |
| | gatcttggcaccaactagggttgtcgctgctgagatggaggaggccttgagaggacttccggtgcgttacatga | |
| | caacagcagtcaacgtcacccattctgggacagaaatcgttgatttgatgtgccatgccactttcacttcacgctta | |
| | ctacaacccatcagagtccctaattacaatctcAacatcatggatgaagcccacttcacagaccccctcaagtata | |
| | gctgcaagaggatacatatcaacaaggggttgaaatgggcgaggcggctgccattttttatgactgccacaccacc | |
| | aggaacccgtgatgcgtttcctgactctaactcaccaatcatggacacagaagtggaagtcccagagagagcct | |
| | ggagctcaggctttgattgggtgacagaccattctgggaaaacagtttggttcgttccaagcgtgagaaacgga | |
| | aatgaaatcgcagcctgtctgacaaaggctggaaagcgggtcatacagctcagcaggaagactttttgacagag | |
| | aatttcagaaaacaaaaaatcaagagtgggactttgtcataacaactgacatctcagagatgggcgccaacttca | |
| | aggctgaccgggtcatagactctaggagatgcctaaaaccagtcatacttgatggtgagagagtcatcttggctg | |
| | gcccatgcctgtcacgcatgctagtgctgctcagaggagaggacgtataggcaggaaccctaacaaacctg | |
| | gagatgagtacatgtatggaggtgggtgtgcagagactggtaaggccatgcacactggcttgaagcaagaat | |
| | gcttcttgacaacatctacctccaggatggcctcatagcctcgctctatcggcctgaggccgataaggtagccgc | |
| | cattgagggagagtttaagctgaggacagagcaaaggaagaccttcgtgaactcatgaagagaggGgacc | |
| | ttcccgtctggctagcctatcaggttgcatctgccggaataacttacacagacagaagatggtgctttgatggcac | |
| | aaccaacaacaccataatggaagacagcgtaccagcaaagtatgggaagatgagaagagtgc | |
| | tcaaaccgagatggatggatgctagggtctgttcagaccatgcgggcctgaagtcgttcaaagaattcgccgct | |
| | ggaaaaaagaggagcggctttggagtaatggaggccctgggaacactgccaggacacatgacagagaggtt | |
| | tcaggaagccattgacaacctcgccgtgctcatgcgagcagagactggaagcaggccttataaggcagcggc | |
| | agcccaactgccgggagacTctagagacAattatgctcttaggtttgctgggaacagtttcactggggatcttctt | |
| | cgtcttgatgcggaataagggcatcgggaagatgggctttgaatggttaaccctcgggggcagtgcatggctca | |
| | tgtggcttcggaaattgaaccagccagaattgcatgtgtcctcattgttgtgttttttattactggtggtgctcatacc | |
| | cgagccagagaagcaaagatctccccaagataaccagatggcaattatcatcatggtggcagtgggccttcta | |
| | ggtttgataactgcaaccagactatggctggaaagaacaaaaaatgactctctaatgggaagag | |
| | agaagaggagcaaccatgggattctcaatggacattgatctgcggccagcctccgcctgggctatctatgccg | |
| | cattgacaactctcatcaccccagctgtccaacatgcggtaaccacttcataccacaactactacttaatggcgat | |
| | ggccacacaagctggagtgctgtttggcatgggcaaagggatgccattttatgcatgggaccttggagtcccgc | |
| | tgctaatgatgggttgctattcacaattaacaccccctgactctgatagtagctatcattctgcttgtggcgcactaca | |
| | tgtacttgatcccaggcctacaagcggcagcagcgcgtgctgcccagaaaaggacagcagctggcatcatga | |

TABLE 7-continued

Sequences

| Name | Sequence | SEQ ID NO |
|---|---|---|
| | agaatcccgttgtggatggaatagtggtaactgacattgacacaatgacaatagaccccccaggtggagaagaa<br>gatgggacaagtgttactcatagcagtagccatctccagtgctgtgctgctgcggaccgcctggggatgggggg<br>gaggctggagctctgatcacagcagcgacctccaccttgtggggaaggctctccaaacaaatactggaactcctc<br>tacagccacctcactgtgcaacatcttcagaggaagctatctggcaggagcttcccttatctatacagtgacgag<br>aaacgctggcctggttaagagacgtggaggtgggacgggagagactctgggagagaagtggaaagctcgtc<br>tgaatcagatgtcggccctggagttctactcttataaaaagtcaggtatcactgaagtgtgtagagaggaggctc<br>gccgtgccctcaaggatggagtggccacaggaggacatgccgtatcccggggaagtgcaaagctcagatgg<br>ttggtggagaggatatctgcagccctatgggaaggttgttgacctcggatgtggcagaggggggctggagct<br>attatgccgccaccatccgcaaagtgcaggaggtgagaggatacacaaagggaggtcccggtcatgaagaac<br>ccatgctggtgcaaagctatgggtggaacatagttcgtctcaagagtggagtggacgtcttccacatggcggct<br>gagccgtgtgacactctgctgtgtgacataggtgagtcatcatctagtcctgaagtggaagagacacgaacact<br>cagagtgctctctatggtgggggactggcttgaaaaaagaccagggggccttctgtataaaggtgctgtgcccat<br>acaccagcactatgatggaaaccatggagcgactgcaacgtaggcatggggggaggattagtcagagtgccatt<br>gtctcgcaactccacacatgagatgtactgggtGtctggggcaaagagcaacatcataaaaagtgtgtccacc<br>acaagtcagctcctcctgggacgcatggatggccccaggaggccagtgaaatatgaggaggatgtgaacctc<br>ggctcgggtacacgagctgtggcaagctgtgctgaggctcctaacatgaaaatcatcggcaggcgcattgaga<br>gaatccgcaatgaacatgcagaaacatggtttcttgatgaaaaccacccatacaggacatgggcctaccatggg<br>agctacgaagccccacgcaaggatcagcgtcttccctcgtgaacggggttgttagactcctgtcaaagccttg<br>ggacgtggtgactggagttacaggaatagccatgactgacaccacaccatacggccaacaaagagtcttcaaa<br>gaaaaagtggacaccagggtgccagatccccaagaaggcactcgccaggtaatgacatagtctcttcctggc<br>tgtggaaggagctggggaaacgcaagcggccacgcgtctgcaccaaaagaagagtttatcaacaaggtgcgc<br>agcaatgcagcactgggagcaatatttgaagaggaaaaagaatggaagacggctgtggaagctgtgaatgat<br>ccaaggttttgggcccctagtggatagggagagagaacaccacctgagaggagagtgtcacagctgtgtgtaca<br>acatgatgggaaaaagagaaaaagaagcaaggagagttcgggaaagcaaaaggtagccgcgccatctggtac<br>atgtggttgggagccagattcttggagtttgaagccctgggatttcttgaacgaggaccatggatggaagagaa<br>aactcaggaggtggagtcgaagggttaggattgcaaagacttggatacattctagaagaaatgaatcggcac<br>caggaggaaagatgtacgcagatgacactgctggctgggacacccgcattagtaagtttgatctggagaatga<br>agctctgattaccaaccaaatggaggaagggcacagaactctggcgttggccgtgattaaatacacataccaaa<br>acaaagtggtgaaggttctcagaccagctgaaggaggaaaaacagttatggacatcatttcaagacaagacca<br>gagagggagtggacaagttgtcacttatgctctcaacacattcaccaacttggtggtgcagcttatccggaacat<br>ggaagctgaggaagtgttagagatgcaagacttatggttgttgaggaagccagagaaagtgaccagatggttg<br>cagagcaatggatgggatagactcaaacgaatggcggtcagtggagatgactgcgttgtgaagccaatcgatg<br>ataggtttgcacatgccctcagggtgcttgaatgacatgatgggaaaagttaggaaaagacacacaggagtgggaaaccc<br>tcgactggatggagcaattgggaagaagtcccgttctgctcccaccactcaacaagctgtacctcaaggatgg<br>gagatccattgtggtccctgtcgccaccaagatgaactgattggccgagctcgcgtctcaccaggggcagga<br>tggagcatccggagactgcctgtcttgcaaaatcatatgcgcagatgtggcagctcctttattccacagaagG<br>gacctttgactgatcggctaatgccatttgctcggctgtgccagttgactgggtTccaactgggagaaccacctg<br>gtcaatccatgaaagggagaatggatgaccactgaggacatgctcatggtgtgaatagagtgtggattgag<br>gagaacgaccatatggaggacaagactcctgtaacaaaatggacagacattcctatctaggaaaaaggag<br>gacttatggtgtggatcccttataggcacagaccccgcaccacttgggctgaaaacatcaaagacacagtcaa<br>catgtgcgcaggatcataggtgatgaagaaaagtacatgtgactatctatccacccaagtcagctcacttgggtg<br>aggaagggtccacacccggagtgttgtaagcaccaatttttagtgttgtcaggcctgctagtcagccacagtttgg<br>ggaaagctgtgcagcctgtaaccccccaggagaagctgggaaaccaagctcatagtcaggccgagaacgc<br>catggcacggaagaagccatgctgcctgtgagcccctcagaggacactgagtcaaaaaacccccacgcgcttg<br>gaagcgcaggatggaaaagaaggtggcgaccttcccaccctteaatctggggcctgaactggagactagc<br>tgtgaatctccagcagagggactagtggttagaggagacccccggaaaacgcacaacagcatattgacgct<br>gggaaagaccagagactccatgagtttccaccacgctggccgccaggcacagatcgccgaacTTCGGC<br>GGCCGGTGTGGGGAAATCCATGGTTTCT | |
| Zika E-W/W/Min (MR766 E-W/W/min) | AGTTGTTgatctgtgtgagtcagactgcgacagttcgagtctgaagcgagag

TABLE 7-continued

Sequences

| Name | Sequence | SEQ ID NO |
|------|----------|-----------|
| | GCGTTAGCTATAGCCTATGTACCGCCGCATTTACGTTTACGAAAGT | |
| | GCCAGCCGAAACGTTGCACGGAACCGTTACCGTCGAGGTGCAATA | |
| | CGCCGGAACCGACGGACCATGCAAGATACCCGTGCAAATGGCCGT | |
| | CGATATGCAGACACTGACACCAGTCGGACGGTTGATTACCGCTAAC | |
| | CCAGTGATAACCGAGTCAACCGAAAACTCTAAGATGATGCTCGAG | |
| | CTTGACCCACCATTCGGCGACTCATATATCGTTATCGGAGTCGGCG | |
| | ACAAAAAGATTACGCATCATTGGCATAGATCCGGATCGACAATCG | |
| | GTAAGGCATTCGAAGCGACAGTGAGAGGCGCTAAGCGTATGGCCG | |
| | TATTGGGCGATACCGCATGGGACTTCGGATCCGTCGGCGGAGTGTT | |
| | TAACTCACTCGGTAAGGGGATACACCAGATATTCGGAGCCGCATTC | |
| | AAATCGTTGTTCGGCGGAATGTCATGGTTTAGTCAGATACTGATCG | |
| | GAACACTGCTTGTGTGGTTGGGGTTGAACACTAAGAACGGATCGAT | |
| | TAGTCTGACATGCTTAGCCTTAGGCGGAGTGATGATTTTTCTGTCA | |
| | ACCGCCGTTAGCGCAGACGTGGGGTGCTCAGTGGACTTCTCAAAAA | |
| | AGGAAACGAGATGTGGCACGGGGGTATTCATCTATAATGATGTTG | |
| | AAGCCTGGAGGGACCGGTACAAGTACCATCCTGACTCCCCCCGCA | |
| | GATTGGCAGCAGCAGTCAAGCAGGCCTGGGAAGAGGGGATCTGTG | |
| | GGATCTCATCCGTTTCAAGAATGGAAAACATCATGTGGAAATCAGT | |
| | AGAAGGGGAGCTCAATGCTATCCTAGAGGAGAATGGAGTTCAACT | |
| | GACAGTTGTTGTGGGATCTGTAAAAAACCCCATGTGGAGAGGTCCA | |
| | CAAAGATTGCCAGTGCCTGTGAATGAGCTGCCCCATGGCTGGAAA | |
| | GCCTGGGGGAAATCGTATTTTGTTAGGGCGGCAAAGACCAACAAC | |
| | AGTTTTGTTGTCGACGGTGACACACTGAAGGAATGTCCGCTTGAGC | |
| | ACAGAGCATGGAATAGTTTTCTTGTGGAGGATCACGGGTTTGGAGT | |
| | CTTCCACACCAGTGTCtggcttaaggtcagagaagattactcattagaatgtgacccagccgtcat | |
| | aggaacagctgttaagggaagggaggccgcgcacagtgatctgggctattggattgaaagtgaaaagaatga | |
| | cacatgcgaggctgaagagggcccacctgattgagatgaaaacatgtgaatggccaaagtctcacacattgtgg | |
| | acagatggagtagaagaaagtgatcttatcataccccaagtctttagctggtccactcagccaccacaacaccag | |
| | agagggttacagaacccaagtgaaagggccatggcacagtggacagActtgaaatccggtttgaggaatgtcc | |
| | aggcaccaaggtttacgtggaggagacatgcggaactagaggaccatctctgagatcaactactgcaagtgga | |
| | agggtcattgaggaatggtgctgtagggaatgcacaatgcccccactatcgtttcgagcaaaagacggctgctg | |
| | gtatggaatggagataaggcccaggaaagaaccagagagcaacttagtgaggtcaatggtgacagcgggt | |
| | caaccgatcatatggaccacttctctcttggagtgcttgttgattctactcatggtgcaggaggggttgaagaagag | |
| | aatgaccacaaagatcatcatgagcacatcaatggcagtgctggtagtcatgatcttggaggatttttcaatgagt | |
| | gacctggccaagcttgtgatcctgatgggtgctactttcgcagaaatgaacactggaggagatgtagctcacttg | |
| | gcattggtagcggcatttaaagtcagaccagccttgctggtGtccttcattttcagagccaattggacacccgtg | |
| | agagcatgctgctagccctggcttcgtgtcttctgcaaactgctctctgctcttgaaggtgacttgatggtcctc | |
| | attaatggatttgctttggcctggttggcaattcgagcaatggccgtgccacgcactgacaacatcgctctaccaa | |
| | tcttggctgctctaacaccactagctcgaggcacactgctcgtggcatggagagcgggcctggctacttgtgga | |
| | gggatcatgctcctctccctgaaagggaaaggtagtgtgaagaagaacctgccatttgtcatggcccctgggatt | |
| | gacagctgagggtagtagaccctattaatgtggtaggactactgttactcacaaggagtgggaagcggagct | |
| | ggccccctagtgaagttctcacagccgttggcctgatatgtgcactggccggagggtttgccaaggcagacatt | |
| | gagatggctggacccatggctgcagtaggcttgctaattgtcagctatgtggtGtcgggaaagagtgtggacat | |
| | gtacattgaaagagcaggAgacatcacatgggaaaaggacgcggaagtcactggaaacagtcctcggcttg | |
| | acgtggcactggatgagagtggtgatttctccttggtagagagaaatggtccacccatgagagatcatactc | |
| | aaggtggtcctgatggccatctgtggcatgaacccaatagctataccttttgctgcaggagcgtggtatgtgtatg | |
| | tgaagactgggaaaaggagtggcgccctctgggacgtgcctgctcccaaagaagtgaagaaaggagaAac | |
| | cacagatggagtgtacagagtgatgactcgcagactgctaggttcaacacaggttggagtgggagtcatgcaa | |
| | gagggagtcttccacacatgtggcacgttacaaaaggagccgcactgaggagcggtgagggaagacttgat | |
| | ccatactggggggatgtcaagcaggacttggtgtcatactgtgggccttggaagttggatgcagcttgggatgg | |
| | actcagcgaggtacagcttttggccgtacctcccggagagagggcagaaacattcagaccctgcctggaata | |
| | ttcaagacaaaggacggggacatcggagcagttgctctggactaccctgcagggacctcaggatctccgatcc | |
| | tagacaaatgtggaagagtgataggactctatggcaatgggttgtgatcaagaatggaagctatgttagtgcta | |
| | taacccaggaaagaggggaggaggagactccggttgaatgtttcgaaccctcgatgctgaagaagaagcagc | |
| | taactgtcttggatctgcatccaggagccggaaaaaccaggagagttcttcctgaaatagtccgtgaagccataa | |
| | aaaagagactccggacagtgatcttggcaccaactagggttgtcgctgctgagatggaggaggccttgagagg | |
| | acttccggtgcgttacatgacaacagcagtcaacgtcacccattctgggacagaaatcgttgatttgatgtgccat | |
| | gccactttcacttcacgcttactacaacccatcagagtcctaatttacaatctcAacatcatggatgaagcccact | |
| | tcacagaccccctcaagtatagctgcaagaggatacatatcaacaagggttgaaatgggcgaggcggctgccat | |
| | ttttatgactgccacaccaccaggaacccgtgatgcgtttcctgactctaactcaccaatcatggacacagaagtg | |
| | gaagtcccagagagagcctggagctcaggctttgattgggtgacagaccattctgggaaaacagtttggttcgtt | |
| | ccaagcgtgagaaacgaaatgaatcgcgcctgtctctgaaaagcgggtcatacagtcagc | |
| | aggaagactttgagacagaattcagaaaacaaaaatcaagagtgggactttgtcataacaactgacatctca | |
| | gagatgggcgccaacttcaaggctgaccgggtcatagactctaggagatgcctaaaaccagtcatacttgatgg | |
| | tgagagagtcatcttggctgggcccatgcctgtcacgcatgctagtgctgctcagaggagaggacgtataggc | |
| | aggaaccctaacaaacctggagatgagtacatgtatgaggtgggtgcagagactgatgaaggcctatgca | |
| | cactggcttgaagcaagaatgcttcttgacaacatctacctccaggatggcctcatagcctcgtctatcggcctg | |
| | aggccgataaggtagccgcccattgagggagagtttaagctgaggacagacaaaggaagaccttcgtggaac | |
| | tcatgaagagaggGgaccttcccgtctggctagcctatcaggttgcatctgccgaataacttacacagacaga | |
| | agatggtgcttttgatgcacaaccaacaacaccataatggaagacagcgtaccagaggtgtggacaaagt | |
| | atggagaagagagtgctcaaaccgagatggatggatgctagggtctgttcagaccatgcgggccctgaagtc | |
| | gttcaaagaattcgccgctggaaaaagaggagcggctttgggagtaatggaggccctgggaacactgccagg | |
| | acacatgacagagaggtttcaggaagccattgacaacctcgccgtgctcatgcgagcagagactggaagcag | |
| | gccttataaggcagcggcagcccaactgccggagacTctagagacAattatgctcttaggtttgctgggaaca | |
| | gtttcactgggatcttcttcgtcttgatgcggaataagggcatcggggaagatgggcttggaatggtaacccttg | |

TABLE 7-continued

Sequences

| Name | Sequence | SEQ ID NO |
|---|---|---|
| | gggccagtgcatggctcatgtggctttcggaaattgaaccagccagaattgcatgtgtcctcattgttgtgtttttat<br>tactggtggtgctcataccgagccagagaagcaaagatctccccaagataaccagatggcaattatcatcatg<br>gtggcagtgggccttctaggtttgataactgcaaacgaacttggatggctggaagaacaaaaaatgacatagc<br>tcatctaatggaaggagagaagaaggagcaaccatgggattctcaatggacattgatctgcggccagcctcc<br>gcctgggctatctatgccgcattgacaactctcatcaccccagctgtccaacatgcggtaaccacttcatacaac<br>aactactccttaatggcgatggccacacaagctggagtgctgtttggcatgggcaaagggatgccatttatgca<br>tgggaccttggagtcccgctgctaatgatgggttgctattcacaattaacacccctgactctgatagtagctatcat<br>tctgctgtggcgcactacatgtacttgatcccaggcctacaagcggcagcagcgcgtgctgcccagaaaagg<br>acagcagctggcatcatgaagaatcccgttgtggatggaatagtggtaactgacattgacacaatgacaataga<br>ccccaggtggagaagaagatgggacaagtgttactcatagcagtagccatctccagtgctgtgctgctgcgg<br>accgcctggggatgggggaggctggagctctgatcacagcagcgacctccaccttgtgggaaggctctcca<br>aacaaatactggaactcctctacagccacctcactgtgcaacatcttcagaggaagctatctggcaggagcttcc<br>cttatctatacagtgacgagaaacgctggcctggttaagagacgtggaggtgggacgggagagactctggga<br>gagaagtggaaagctcgtctgaatcagatgtcggccctggagttctactcttataaaaagtcaggtatcactgaa<br>gtgtgtagagaggaggctcgccgtgccctcaaggatggagtggccacaggaggacatgccgtatcccgggg<br>aagtgcaaagctcagatggttggtggagaggtatctgcagccctatgggaaggttgttgacctcggatgtg<br>gcagaggggctggagctattatgccgccaccatccgcaaagtgcaggaggtgagaggatacacaaaggga<br>ggtcccggtcatgaagaacccatgctggtgcaaagctatgggtgaacatagttcgtctcaagagtggagtgg<br>acgtcttccacatggcggctgagccgtgtgacactctgctgtgtgacataggtgagtcatcatcagtcctgaagt<br>ggaagagacacgaacactcagagtgctctctatggtggggggactggcttgaaaaaagaccagggggccttctgt<br>ataaaggtgctgtgcccatacaccagcactatgatggaaaccatgcgagcgactgcaacgtaggcatggggga<br>ggattagtcagagtgccattgtctcgcaactccacacatgagatgtactgggtGtctggggcaaagagcaacat<br>cataaaaagtgtgtccaccacaagtcagctcctcctgggacgcatggatggcccaggaggccagtgaaatat<br>gaggaggatgtgaacctcggctcgggtacacgagctgtggcaagctgtgctgaggctcctaacatgaaaatca<br>tcggcaggcgcattgagagaatccgcaatgaacatgcagaaacatgtttcttgatgaaaacaccccatcagg<br>acatgggcctaccatgggagctacgaagccccacgcaaggatcagcgtcttccctcgtgaacggggttgtta<br>gactcctgtcaaagccttgggacgtggtgactggagttacaggaatagccatgactgacaccacaccatacgg<br>ccaacaaagagtcttcaaagaaaaagtggacaccagggtgccagatcccaagaaggcactcgccaggtaat<br>gaacatagtctcttcctggctgtgaaagagctgggaaacgcaagcggccacgcgtctgcaccaaagaaga<br>gtttatcaacaaggtgcgcagcaatgcagcactgggagcaatatttgaagaggaaaaagaatggaagacggct<br>gtggaagctgtgaatgatccaaggttttgggccctagtggataggagagagaacaccctgagaggagag<br>tgtcacagctgtgtgtacaacatgatgggaaaagagaaaagaagcaaggagagttcgggaaagcaaaaggt<br>agccgccatctggtcatgtggttgggagccagattcttggagtttgaagcccttggattcttgaacgaggac<br>cattggatgggaagagaaaactcaggaggtggagtcgaagggttaggattgcaaagacttggatacattctag<br>aagaaatgaatcggcaccaggaggaaagatgtacgcagatgacactgctggctgggacacccgcattagta<br>agtttgatctggagaatgaagctctgattaccaaccaaatggaggaagggcacagaactctggccgttggccgtg<br>attaaatacacataccaaaacaaagtggtgaaggttctcagaccagctgaaggaggaaaaacagttatggacat<br>catttcaagacaagaccagagagggagtggacaagttgtcacttatgctctcaacacattcaccaacttggtggt<br>gcagcttatccggaacatgaagctgaggaagtgttagagatgcaagacttatggttgttgaggaagccagag<br>aaagtgaccagatggttgcagagcaatggatgggatagactcaaacgaatggcggtcagtggagatgactgc<br>gttgtgaagccaatcgatgataggtttgcacatgccctcaggttcttgaatgacatgggaaaagttaggaaagac<br>acacaggagtggaaaccctcgactggatggagcaatgggaagaagtcccgttctgctcccaccacttcaaca<br>agctgtacctcaaggatgggagatccattgtggtcccttgccgccaccaagatgaactgattggccgagctcgc<br>gtctcaccaggggcaggatggagcatccgggagactgcctgtcttgcaaaatcatatgcgcagatgtggcagc<br>tccttttatttccacagaagGgaaccttcgactgatggctaatgccatttgctcggctgtgccagttgactgggtTcc<br>aactgggagaaccacctggtcaatccatggaaaggggagaatggatgaccactgaggacatgctcatggtgtg<br>gaatagagtgtggattgaggagaacgaccatatggaggcaagactcctgtaacaaaatggacagacattccc<br>tatctaggaaaaagggaggacttatggtgtggatcccttatagggcacagaccccgcaccacttgggctgaaaa<br>catcaaagacacagtcaacatggtgcgcaggatcatcaggtgatgaagaaaagtacatggactatctatccaccc<br>aagtccgctacttgggtgaggaagggtccacacccggagtgttgtaagcaccaatttttagtgttgtcaggcctgc<br>tagtcagccacagtttggggaaagctgtgcagcctgtaaccccccaggagaagctgggaaaccaagctcata<br>gtcaggccgagaacgccatggcacggaagaagccatgctgcctgtgagcccctcagaggacactgagtcaa<br>aaaaccccacgcgcttggaagcgcaggatgggaaaagaaggtggcgaccttcccccaccctttcaatctggggc<br>ctgaactggagactagctgtgaatctccagcagagggactagtggttagaggagaccccccggaaaacgcac<br>aacagcatattgacgctgggaaagaccagagactccatgagtttccaccacgctggccgccaggcacagatc<br>gccgaacTTCGGCGGCCGGTGTGGGGAAATCCATGGTTTCT | |
| A/California/<br>07/2009M100/<br>V6-<br>HA-Min<br>(CodaVax-<br>H1N1<br>M101/V6) | agcaaaagcaggggaaaataaaagcaacaaaaatgaaggc TABLE 7-continued Sequences

| Name | Sequence | SEQ ID NO |
|---|---|---|
| | acgccgaaatgttagtgttactcgaaaacgaaagaacactagactatcacgattcaaacgttaagaatctatacg<br>aaaaagtgagatcgcaattgaaaaataacgctaaagagatagggaatgggtgtttcgaattctatcataaatgcg<br>ataatacatgtatggaatccgttaaaaacggaacatacgattaccctaagtatagcgaagaggctaaactgaata<br>gggaagagatagacggagtggaacttgaatcaactaggatttatcagatactcgcaatttatagtacggttgcca<br>gttcattggtactggtagtctccctgggggcaatcagtttctggatgtgctctaatgggtctctacagtgtagaatat<br>gtatttaacattaggatttcagaagcatgagaaaaacacccttgtttctact | |
| A/California/<br>07/2009M100/<br>V6-NA-<br>Min<br>(CodaVax-<br>H1N1<br>M101/V6) | agcaaaagcaggggtttaaaATGAATCCAAACCAAAAGATAATAACCATTGGT<br>TCGGTCTGTATGACAATTGGAATGGCTaacttaatattacaaattggaaacataatctca<br>atatggattagccactcaatccaattggggaatcagaatcaaatcgaaacatgcaatcaatccgtaattacatacg<br>agaataatacttgggtgaatcagacatacgttaacatatcgaatactaatttcactgccggacaatccgtcgtgagt<br>gtgaaactagccggtaatagtagtctatgtcccgttagcggatgggctatatactctaaagacaatagcgttagaa<br>tcggatctaaaggcgacgtattcgttatacgcgaaccattcataagttgtagtccattagagtgtaggactttttttct<br>gacacagggcgcactattgaacgataagcattctaacggtacaatcaaagataggtcaccatatagaacactaa<br>tgtcatgtccgataggcgaagtgcctagtccatacaatagtagattcgaatccgtcgcttggtccgctagcgcatg<br>ccatgacggtattaattggttgacaatcgggattagcggaccccgataacggcgcagtcgcgcgtacttaagtataa<br>cggtataattaccgatactattaagagttggcgaaataatatattgcgaacacaggaatccgaatgcgcatgcgtt<br>aacggatcatgttttaccgttatgactgacggaccatctaacgggcaagcgtcatataagattttttagaatcgaaa<br>aaggtaagatagtgaaatccgtcgaaatgaacgctcctaattatcattacgaagagtgctcatgttatcccgattct<br>agcgaaattacatgcgtatgtagacgacaattggcacggatctaatagaccttgggtgtcattcaatcagaatctag<br>agtatcaaatcgggtatatatgctcagggatattcggagacaatcctagacctaacgataagacagggtcatgcg<br>gaccagtgagttctaacggcgctaacggcgttaaggggtttagtttcaaatacggtaacggcgtatggataggg<br>agaactaagtcaatctctagtagaaacggattcgaaatgatatgggaccctaacggatggaccggaaccgataa<br>taattttcgattaaacaggatatcgtagggattaacgaatggtcagggtatagcggatcattcgtacagcatcca<br>gagttaaccggactcgattgcatacgaccatgttttgggtcgaactgattagggggagaccgaaagagaatact<br>atatggactagcgggagcagcatatcctttgtggtgtaaacagtgacactgtgggttggtcttggccagacggt<br>gctgagttgccatttaccattgacaagtaatttgttcaaaaaactccttgtttctact | 6 |

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Modification of PV Sequences to Alter Codon Pair Score Relative to Human Codon Pair Bias Our algorithm was given the input of the DNA coding sequence for the P1 structural region of poliovirus type-1 Mahoney strain (PV(M)-wt), and the CPB of this region was customized (FIG. 2). After customization using simulated annealing, we produced two novel segments with shuffled codons and thus novel codon-pairs. The first design was PV-Max which had a positive CPB of +0.246. This positive CPB indicated that PV-Max utilized, on average, over-represented codon-pairs. The second design was PV-Min, which had a negative CPB of −0.474. This negative CPB indicated that PV-Min utilized, on average, under-represented codon-pairs (FIG. 1). The first four codons (12 nucleotides) were not changed in PV-Min and PV-Max and left the same as the wild type poliovirus codons. This was done so that translation might initiate equally in all constructs. Also, the P1 region was selected as a suitable region for replacement by a synthetic fragment because it has been demonstrated that the elimination or replacement of this region with foreign, non-polio derived sequence does not affect replication. This tolerance of foreign sequence in the P1 region strongly suggests the absence of replication regulatory elements within this region. The sequence of one candidate, PV-MinY (SEQ ID NO:1) is a non-limiting example.

The computer alteration of the poliovirus P1 region resulted in two novel sequences with extreme CPBs. PV-Max possessed 566 silent mutations when compared to PV(M)-wt and PV-Min possessed 631 silent mutations (FIG. 2). The calculated CPB scores, using the equation mentioned previously, of the novel P1 regions as well as of all annotated human ORFs can be observed in FIG. 1. The designed PV-Max and PV-Min had extreme CPBs, +0.246 and −0.474 respectively, which exceeded the outer limit of naturally occurring human sequences (FIG. 1).

Example 2

Construction of Codon Pair Deoptimized Polioviruses

Plasmids containing the cDNA of the resulting recombinant virus of the above-mentioned genotype or any other variant were amplified, purified and digested with the restriction endonuclease FspI for linearization (this endonuclease cuts within vector sequences). The resulting linearized cDNA (which contains a recognition motif for the DNA-dependent RNA polymerase T7 preceding the 5′ insertion site of the virus cDNA) was used for in vitro transcription using T7 polymerase to produce full-length viral RNA. Viral RNA thus generated was used to transfect HeLa cells by the Dextran-sulfate method in order to produce infectious virus. Transfected cells were observed for the occurrence of the cytopathic effect indicating productive modified virus infection and infectious virus was propagated in HeLa cells, purified and frozen for indefinite storage.

Example 3

Modified Virus is Attenuated Compared to Wild-Type but Grows and Kills Adenocarcinoma Cervical Cancer Cells-HeLa R19 Cells After transfecting the five PV-Min derivate RNAs into HeLa R19 cells, each product virus was passaged twice to ensure the virus was properly amplified because RNA transfection is not as efficient as a natural infection by the virus itself. Next, plaque assays were performed to elucidate the apparent PFU/ml titer for each virus (FIG. 3). These subclones yielded viruses which had varying degrees of attenuation. The viruses containing P1 fragments X and Y were each attenuated by 0.8-1 $\log_{10}$; however, when added together they yielded virus PV-MinXY, which was significantly attenuated by 2.5 orders of magnitude. The virus PV-MinZ was also attenuated on the order of 2.5 $\log_{10}$ like PV-MinXY. Thus, when returning the Y fragment to PV-MinZ, the construct PV-YZ failed to yield viable virus (FIG. 3). These varying degrees of attenuation therefore was due to an apparent additive effect. Thus, one could conclude the null phenotype of the full-length PV-Min construct was due to the sum of defects in the various three sub-regions.

HeLa R19 cells are adenocarcinoma cervical cancer cells that have low or absent p53 gene expression and are positive for keratin by immunoperoxidase staining.

Example 4

CpG and UpA Dinucleotide Frequency Increase in Modified Sequences

Another important observation that provides further description of CPB suggests that the N3-N1 nucleotides (i.e., the last nucleotide of codon A and first nucleotide of codon B) between the codon-pair in fact has the greatest influence on CPB and thus strongly influence pairing. Specifically, that a codon-pair with a C at N3 and G at N1 (designated CpG or $CG_{3-1}$) are avoided, or strongly under-represented. Actually, this dinucleotide is suppressed within codons as well ($CG_{12}$, $CG_{23}$) and it is uncertain why this dinucleotide is avoided. The CpG dinucleotide, within an individual codon or between codons, could have an impact on translation, be repressed due to genomic forces, or the presence of CpG is used to distinguish self from non-self in eukaryotes. It is important to note that the rarest individual codons also contain an internal CG (i.e., $CG_{1-2\ and\ 2-3}$) suggesting this dinucleotide is actively avoided for some purpose.

The first supposition is that CpGs impact translation, firstly because rare codons contain it (i.e., $CG_{1-2\ and\ 2-3}$) and also as a result of incompatible tRNAs corresponding to the $CG_{3-1}$ dinucleotide. Specifically, that this nucleotide pair's high-stacking energy serves to impede the traveling ribosome. Another group supposes that CpG dinucleotides are suppressed within genes as an indirect result of DNA methylation in mammalian genomes; however, CpGs still appear in the mRNA and thus is a less likely target of methylation. Lastly, it is known that CpG-containing DNA and CpG-containing single stranded RNA are immune stimulators, thus the under-representation of CpG within a eukaryotic organism's own genes could be a means to prevent self-reactivity of a cell's own genes stimulating an innate response. This idea of CpG used as a means for self versus non-self recognition has a few supporting observations. Firstly, that codons themselves containing CpGs (i.e., $CG_{1-2\ and\ 2-3}$) are rare codons and codon-pairs with a CpGs ($CG_{3-1}$) at their junction are under-represented. Also viruses, specifically small RNA viruses infecting eukaryotes, suppress CpGs in their genome, possibly because they have evolved to lower their CpG content so as to avoid innate immune recognition and the triggering of a response. Lastly, it has been seen that single-stranded RNA containing CpGs can stimulate monocytes. All of these observations of an effect of nucleic acid composition at the codon-codon junction only serve to further define CPB; however, these observations fail to clarify the biological effects of CPB.

Example 5

Figure 4A:
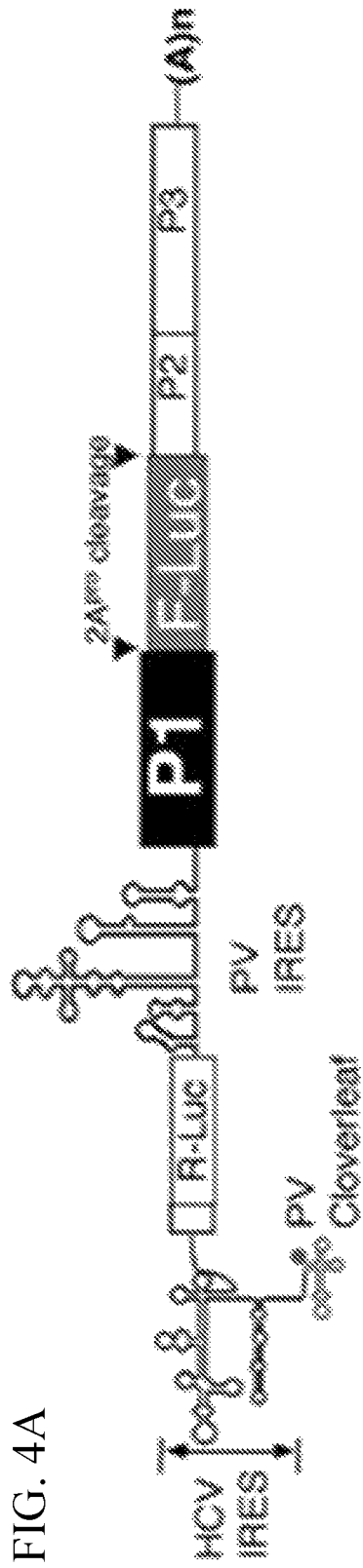

Reduction of Protein Expression by Modification of Codon-Pair Bias and CpG or UpA Increase As depicted in FIG. 4, protein expression was reduced by modification of codon-pair bias.

TABLE 3

| CpG and UpA increase in PV-WT and PV-MinY. | | | |
|---|---|---|---|
| Di-nucleotide | PV-WT | PV-MinY | Increase |
| CpG | 176 | 218 | +41 |
| UpA | 366 | 392 | +26 |

Example 6

In Vivo Attenuation by Modification

The neurovirulence of the PV-Min chimeras XY and Z and PV-Max was tested in CD155tg mice via intracerebral injection with increasing doses of the viruses. Specifically, groupings of four to six, 6-8 week-old CD155tg mice were inoculated with varying doses and then observed for the onset of poliomyelitis. Control groupings of mice were injected in parallel experiments with PV(M)-wt. Injection doses were based on particles rather than PFU so as to normalize the quantity of virions inserted into the brain. The mice were monitored daily for the onset of flaccid paralysis, the characteristic symptom of poliomyelitis. The standard value used to quantify the virulence of a virus is the Lethal Dose 50 ($LD_{50}$). This value indicates the dose of inoculating virus at which fifty percent of the animals live and fifty percent die. The synthetic viruses PV-MinXY and PV-MinZ had a higher $LD_{50}$ than PV(M)-wt and therefore were, 1,500-fold based on particles or 20-fold based on PFU, less pathogenic (Table 3).

TABLE 4

| Calculated $LD_{50}$ for wild type poliovirus, and modified viruses via intracerebral (i.c.) injection. | |
|---|---|
| Virus | $LD_{50}$ (i.c.) Particles) |
| PV(M)-wt | $10^{4.0}$ |
| PV-Min Y | $10^{5.0}$ |
| PV-MinXY | $10^{7.1}$ |
| PV-MinZ | $10^{7.3}$ |

Example 7

In Vivo Oncolysis of Astrocytomas with Chimeric Polioviruses

Figure 5B:
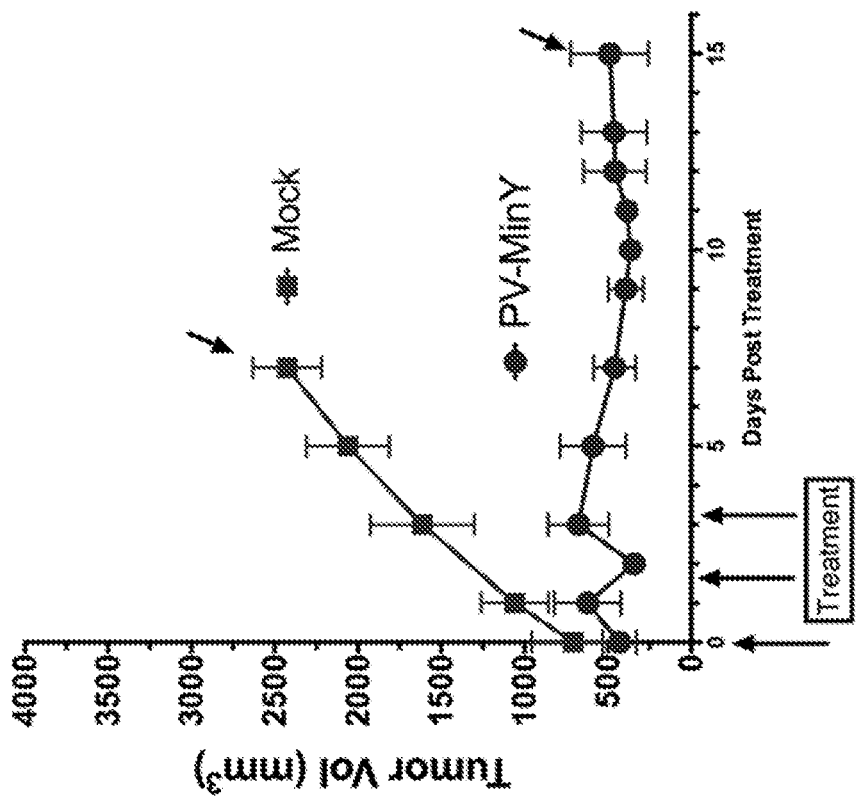
FIGS. 5A-5B depict control of tumor growth in NCR nude mice treated with modified poliovirus MV-MinY. Each mouse (n=7; A) was treated on days 0, 3, and 5 after the tumor reached a size of 0.2 cm$^3$ with $2 \times 10^7$ PFU of PV-MinY or mock injected.
Figure 5A:
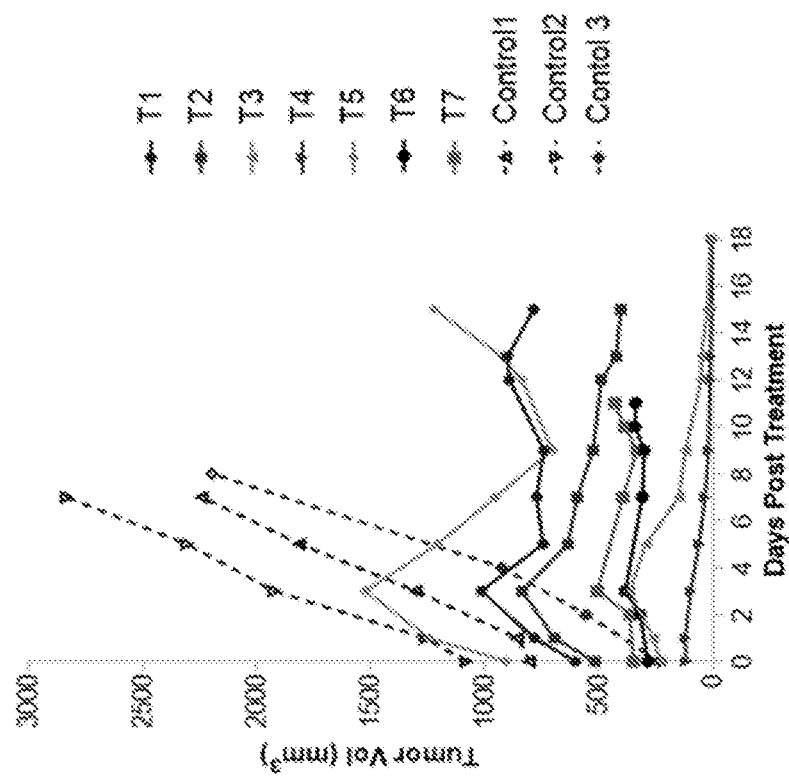
Figure 6:
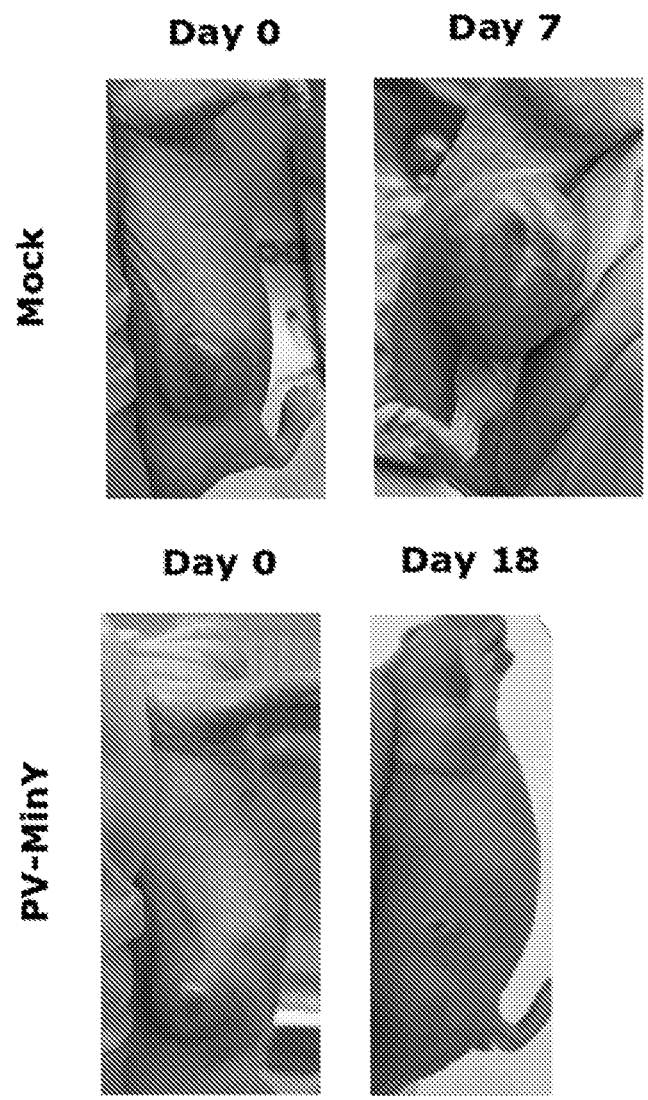
FIG. 6 depict oncolysis of astrocytomas in NCR nude mice by PV-MinY (bottom) compared to untreated control mice (top). NCR Nude mice were injected subcutaneously with $1 \times 10^6$ HTB-14 cells and the experiment was started once the tumors had reached a size of 0.2 cm$^3$. On days 0, 3, and 5 the tumors were injected with mock diluent (top) or $2 \times 10^7$ PFU of PV-MinY (bottom). PV-MinY injected tumor size was maintained or reduced while the animals in the mock treated group had to be euthanized after 7 days due to tumor size.

Using the astrocytoma cell line HTB-14 (obtained from ATCC), malignant gliomas were established through subcutaneous implantation of $10^6$ cells into Taconic Farms NCR nude mice. The mice were treated or mock treated on days 0, 3, and 5 after the tumor reached a size of 0.2 cm$^3$ with $2 \times 10^7$ PFU of PV-MinY, WT PVM, or diluent in a volume of 100 µL. PV-MinY and PVM were effective in preventing the growth of tumors in nude mice (FIGS. 5 and 6).

HTB-14 cells, also known as U-87 MG cells are malignant glioblastoma cells that are a hypodiploid human cancer cell line.

Example 8

Oncolysis of Lung Carcinoma Cells

Figure 7:
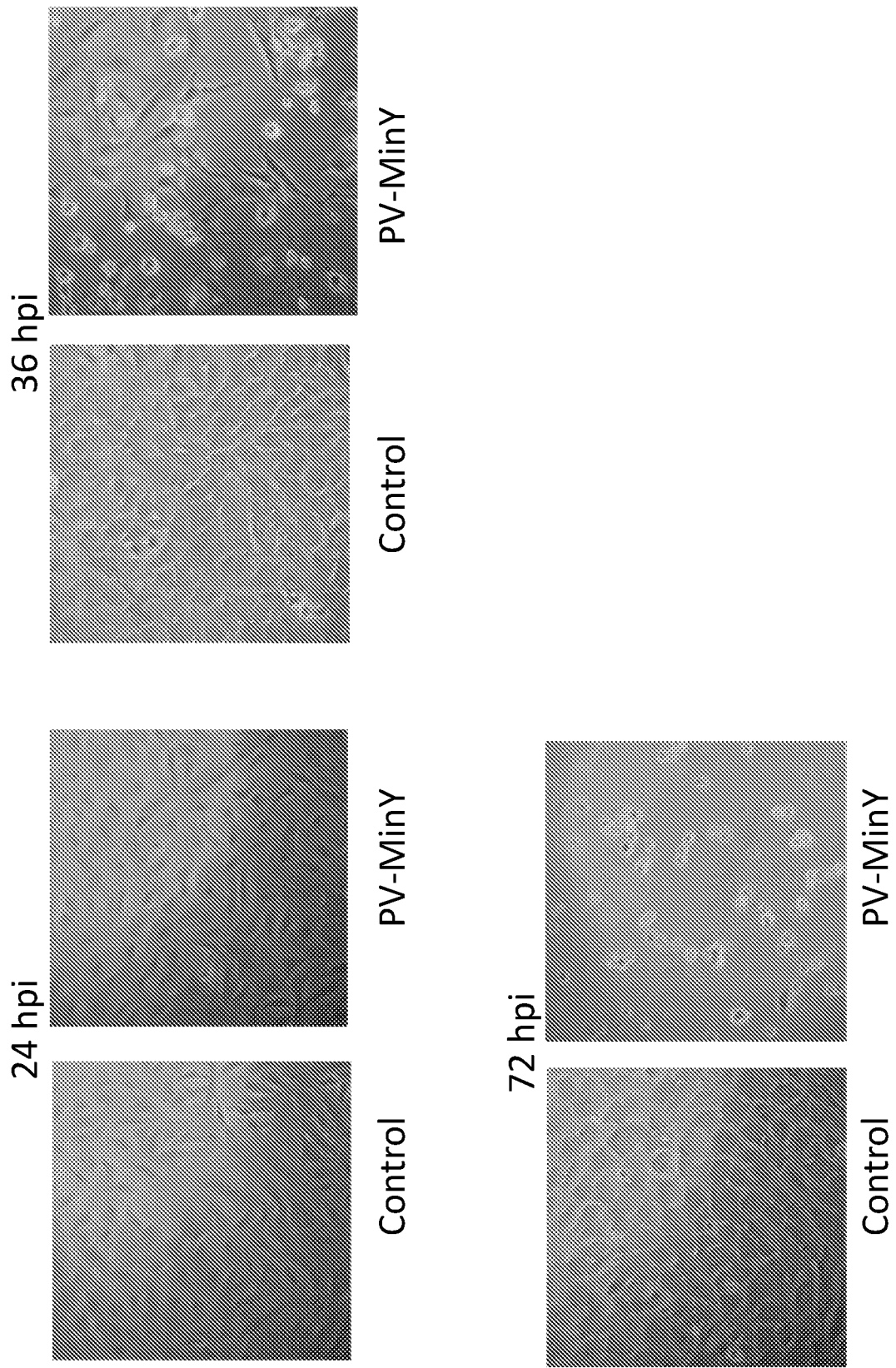
FIG. 7 depicts the oncolysis of A549 cells by the modified virus PV-MinY. A549 cells are cells are a hypotriploid (64, 65, or 66 chromosome count in 40% of cells) human lung epithelial carcinoma cell line (Giard et al., 1973). Chromosomes N2 and N6 had single copies per cell; and N12 and N17 usually had 4 copies. A549 cells are positive for keratin by immunoperoxidase staining. A549 express the isoenzyme G6PD-B of the enzyme glucose-6-phosphate dehydrogenase (G6PD. We used A549 cells as a model for lung carcinoma. A549 cells were infected with at an MOI of 1.0 by PV-MinY. A549 cells were grown in DMEM+10% FBS. Cells were infected at 90% confluences with $10^6$ PFU PV-MinY, after 1 hour rocking at Room temperatures; inoculums were removed and replaced with DMEM+2% FBS. Infected cells were incubated at 37 C, 5% $CO_2$ incubator. As evident by FIG. 7 and in comparison to uninfected lung carcinoma cells, PV-MinY could oncolysis most cells by 36 hours and all cells by 72 hours post infection.

We used the lung carcinoma cell line A549 (ATCC CCL-185) as a model for our oncolytic candidate PV-MinY by infecting A549 cells at an MOI of 1.0 by PV-MinY. A549 cells were grown in DMEM+10% FBS. Cells were infected at 90% confluences with 1e+6 PFU PV-MinY, after 1 hour rocking at Room temperatures, inoculums were removed and replaced with DMEM+2% FBS. Infected cells were incubated at 37 C, 5% $CO_2$ incubator. As evident by FIG. 7 and in comparison to uninfected lung carcinoma cells, PV-MinY could oncolysis most cells by 36 hours and all cells by 72 hours post infection.

A549 cells are a hypotriploid (64, 65, or 66 chromosome count in 40% of cells) human lung epithelial carcinoma cell line (Giard et al., 1973). Chromosomes N2 and N6 had single copies per cell; and N12 and N17 usually had 4 copies. A549 cells are positive for keratin by immunoperoxidase staining. A549 express the isoenzyme G6PD-B of the enzyme glucose-6-phosphate dehydrogenase (G6PD).

Example 9

Figure 8A:
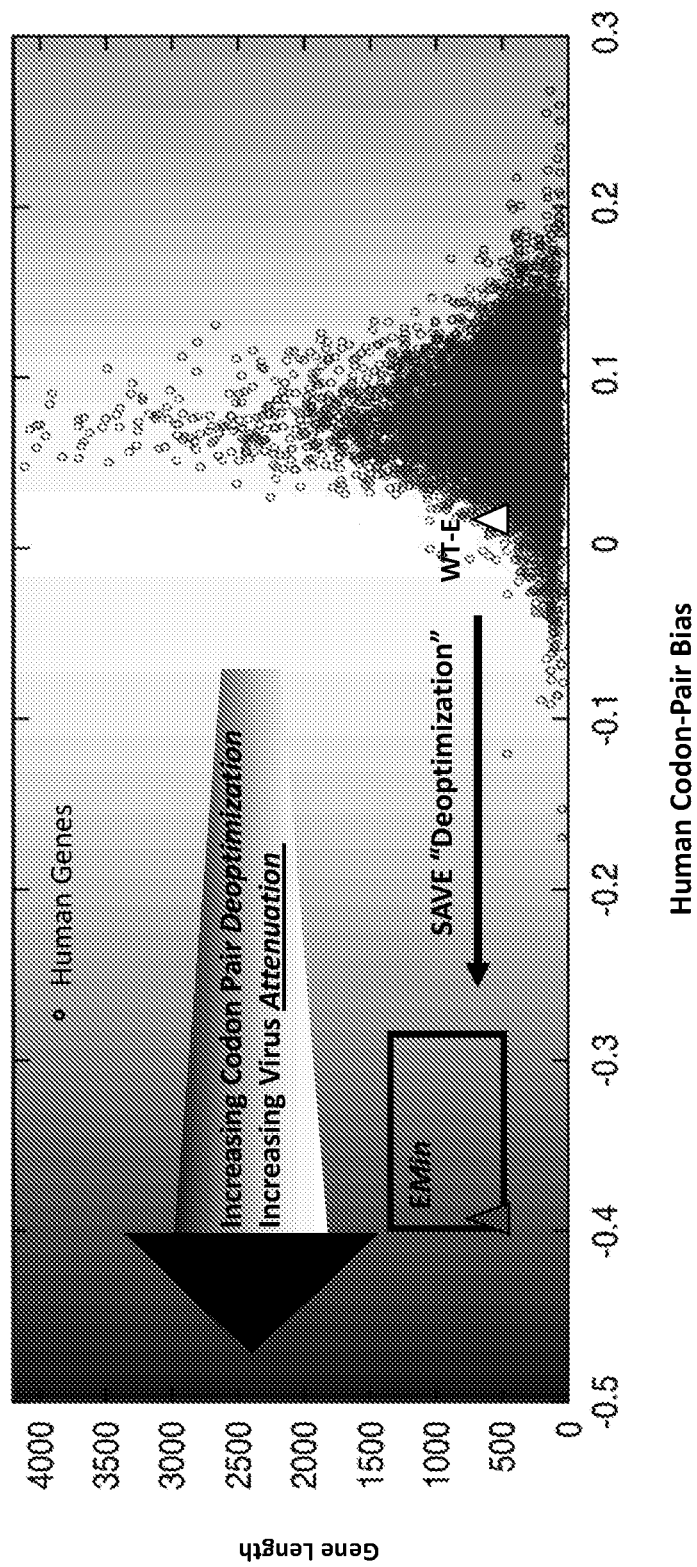

Construction and Characterization of a E, NS3 and E-NS3 Codon Pair-Bias Reduced Zika Virus in Tissue Culture To achieve attenuation of Zika virus strains PRVABC59 and MR766, codon pair bias of the prM/E and NS3 genes was reduced (introducing underrepresented codon pairs) in viral genes according to computer algorithms and chemical synthesis in order to reduce the expression level of the viral genes (FIG. 8).

Example 10

Figure 9:
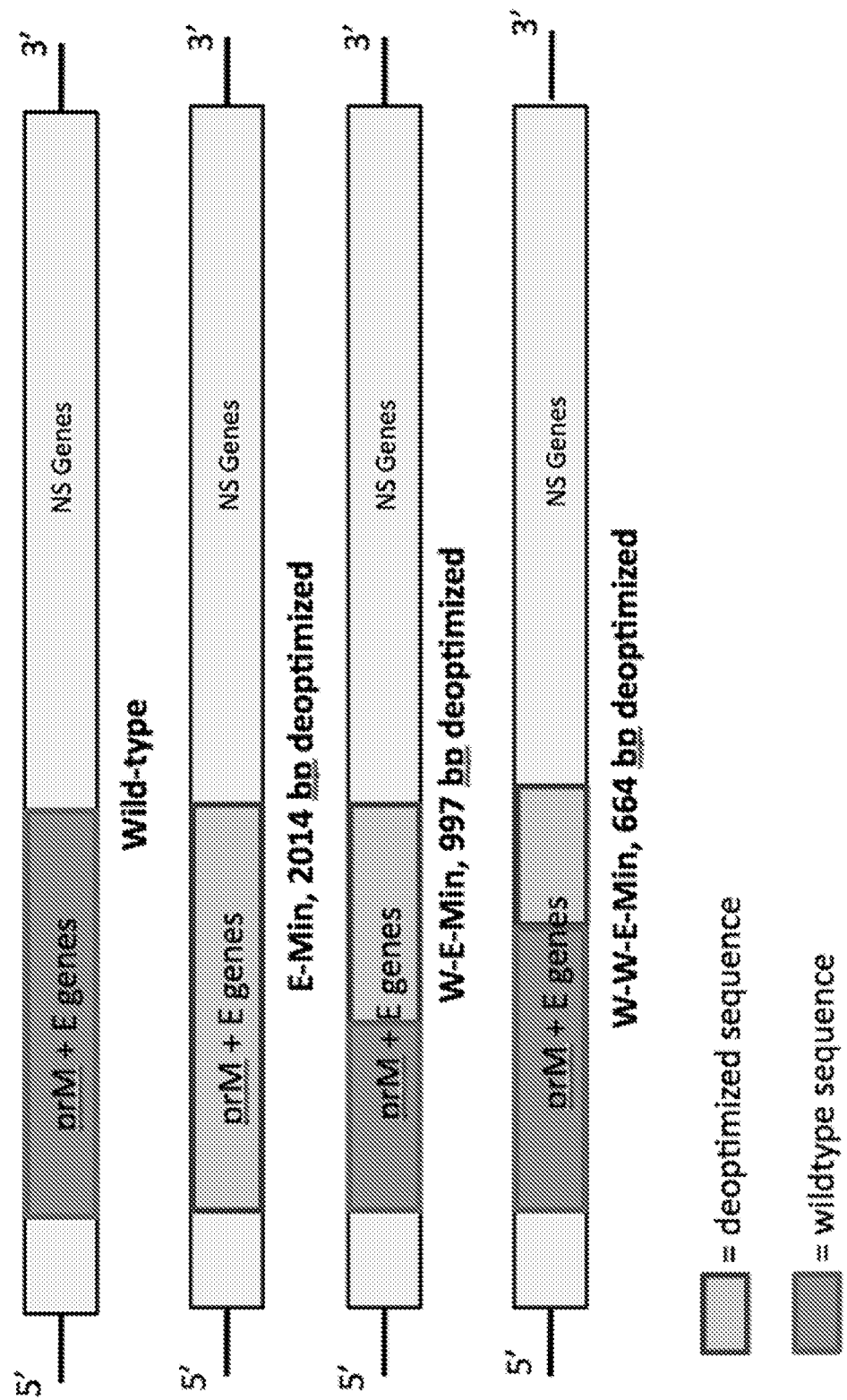
FIG. 9 describes a diagram of subcloning strategies for decreasing attenuation or increasing immunogenicity by reducing the length of deoptimized sequence in the prM+E encoding region. The second generation of Zika vaccine candidates leverages the flexibility of the SAVE platform to reduce the deoptimized region from 2014 bp (E-min) to 997 bp (E-W/Min) or further to 664 bp (E-W/W/Min) while keeping the amino acid sequence 100% identical.

Leveraging SAVE Platform Flexibility to Create Second-Generation Zika Virus Vaccine Candidates To fine-tune attenuation and immunogenicity, a second generation of Zika virus vaccine candidates were constructed using the SAVE platform (FIG. 9). Based on the E-Min design (FIG. 8), the new vaccine candidates contained a smaller proportion of deoptimized sequence lowered from 2014 base-pairs (E-Min) to either 997 base-pairs (E-W/Min) or 664 base-pairs (E-W/W/Min) with the remainder restored to wild-type sequence. The sequences of the three candidates MR766 E-Min (SEQ ID NO: 2), E-W/Min (SEQ ID NO: 3), and E-W/W/Min (SEQ ID NO: 4) are provided herein as non-limiting examples.

Example 11

Neuroattenuation of Reduced Codon-Pair Bias Variants' in Human Neuronal Cell Lines Unlike the older ZIKV strains such as MR766, the current strains of ZIKV cause neurological disease such as microcephaly and Guillain-Barre syndrome. Thus, based on our pre, pre-IND meeting with the FDA, any live-attenuated Zika vaccine would need to demonstrate neuro-attenuation in human neuronal cells in vitro and neuro-attenuation in nonhuman primates in vivo (proposed Phase II work). To begin the pre-clinical development of our lead candidate, we infected two well-characterized human neuronal cell lines HTB-14 (also known as U-87) and HTB-15 (also known as U-118), which have been used previously to characterize Zika virus cell tropism in the developing human brain and to test potential anti-Zika inhibitors. We infected human neuronal cell lines HTB-14 and HTB-15 and quantified peak titers after 4 days. We observed that in human HTB-14 cells, MR766 E-Min was nearly 4 $Log_{10}$s attenuated and in human HTB-15 cells, growth was either undetectable in two independent experiments or at the limit of detection in one experiment (100 PFU/ml) also representing a nearly 4 $Log_{10}$ level of neuro attenuation in vitro (data not shown).

Example 12

Levels of Protein are Reduced in PRVABC59 or MR766 Derived E-Min Infected Cells Western Blot of whole cell lysates taken from ZIKV infected cells were used to compare levels of protein expression between different PRVABC59 and MR766 variants. For virus infection, Vero cells were grown in the OptiPRO medium at 37° C. till 90% confluent. Zika viruses, including synthetic wildtype and de-optimized (E-Min) MR766 and PRVABC59, were diluted to a MOI of 0.5 and were added to the cells. The cells were rocked for 15 min at R.T., then incubated at 33° C. for 2 hrs. Next, the inocula were removed, and the infected cells were continued to culture in OptiPRO medium at 33 C for 24 hrs.

For whole cell lysate preparation after 24 hr incubation, cells were briefly rinsed with cold PBS, then lysed on ice with RIPA buffer (150 mM NaCl, 5 mM b-mercaptoethanol, 1% NP-40, 0.1% sodium dodecyl sulfate, 50 mM Tris-HCl, pH8.0). Whole cell lysates were collected, directly mixed with 6× Laemmli buffer with b-mercaptoethanol, boiled and aliquoted for storage.

For Western blot, an equal volume of WCL from each sample was fractionated by SDS-PAGE and transferred to a nitrocellulose membrane. The membrane was blocked with 5% bovine calf serum (BCS) in PBS for 1 hr at R.T., then incubated with a mouse monoclonal antibody against dengue type-2 envelope(E) protein 4G2 overnight at 4 C, washed three times with PBS-Tween, subsequently incubated with HRP conjugated anti-mouse secondary antibody in 5% BCS for 1 hr at R.T. The membrane was washed three times, and proteins were visualized using Pierce 1-Step Ultra TMB Blotting solution.

Levels of the envelope glycoprotein were found to be reduced in E-Min variants of PRVABC59 and MR766 strains of ZIKV compared to wildtype (FIG. 10).

Example 13

Attenuation in AG129 Mice

As described above, the AG129 adult mouse model is gaining acceptance for studies of flavivirus vaccines and therapeutics. We used AG129 mice to test: 1) each synthetically derived wild-type virus MR766 and PR15 virus at a dose of $10^2$ (positive control); 2) two doses ($10^4$ and $10^2$ PFU) of the vaccine candidates PR15 E-Min or MR766 E-Min and NS3-Min; and 3) a single dose of $10^4$ of the vaccine candidates PR15-NS3/E-Min. In this study we examined attenuation, efficacy, and immunogenicity. Animals were randomly assigned to groups of 5 animals. Groups were infected with various attenuated and synthetic wild-type viruses. Two rounds of vaccination were performed on Day 0 and Day 28 to vaccinate mice. To measure attenuation, survival and weight was measured post-vaccination (FIG. 11).

Figure 12:
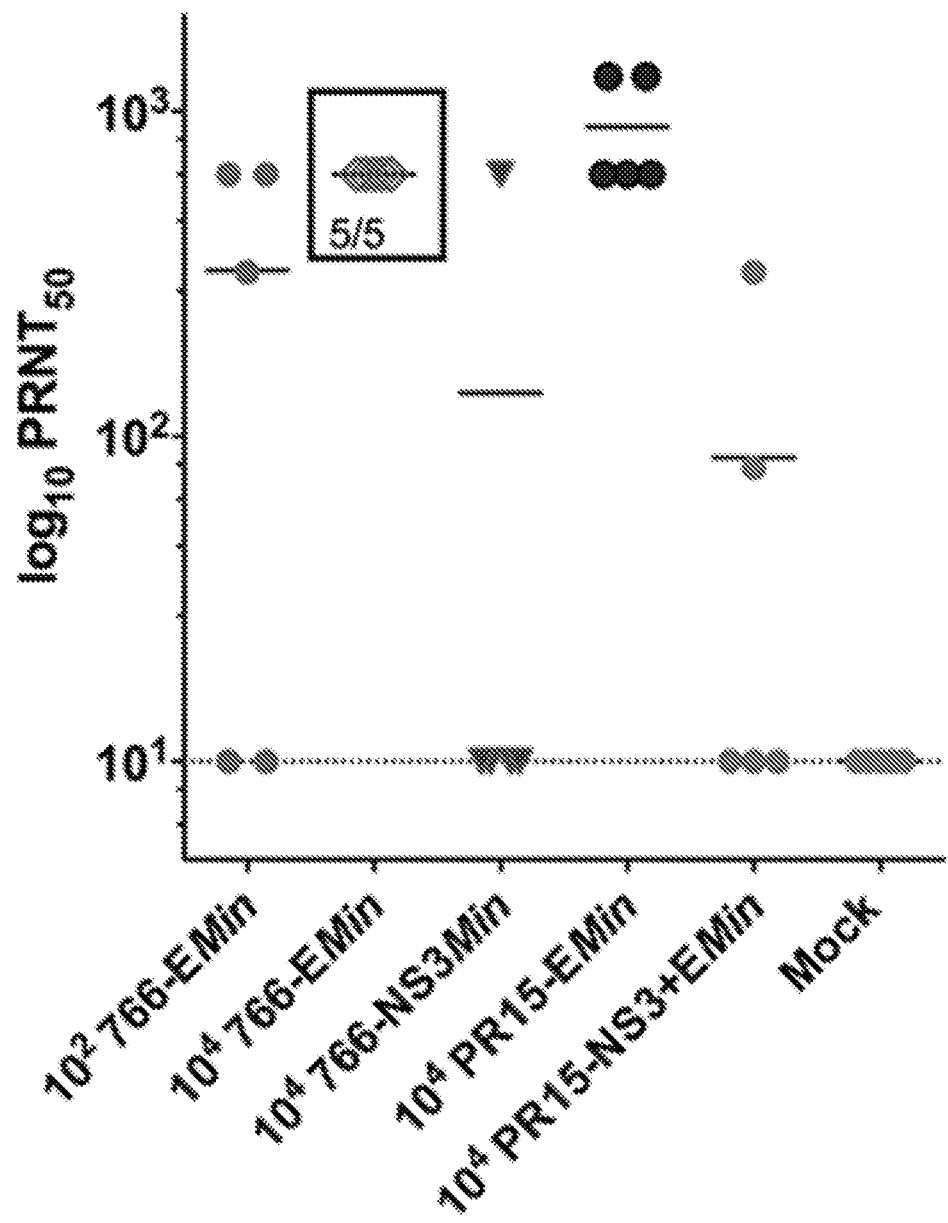
FIG. 12 describes SAVE-attenuated ZIKV vaccine candidates inducing high levels of neutralizing antibodies and protect from lethal challenge in AG129 mice. A) Anti-PR15 Zika antibodies after a single dose. Serum from vaccinated animals was harvested on Day 28 and antibodies were quantified against ZIKV strain PR15 via $PRNT_{50}$ assay on Vero cells. Mice vaccinated with both PR15 E-Min and MR766 E-Min at the $10^4$ dose developed high levels of neutralizing antibodies (2.8 $\log_{10}$ PRNT50).
Figure 13:
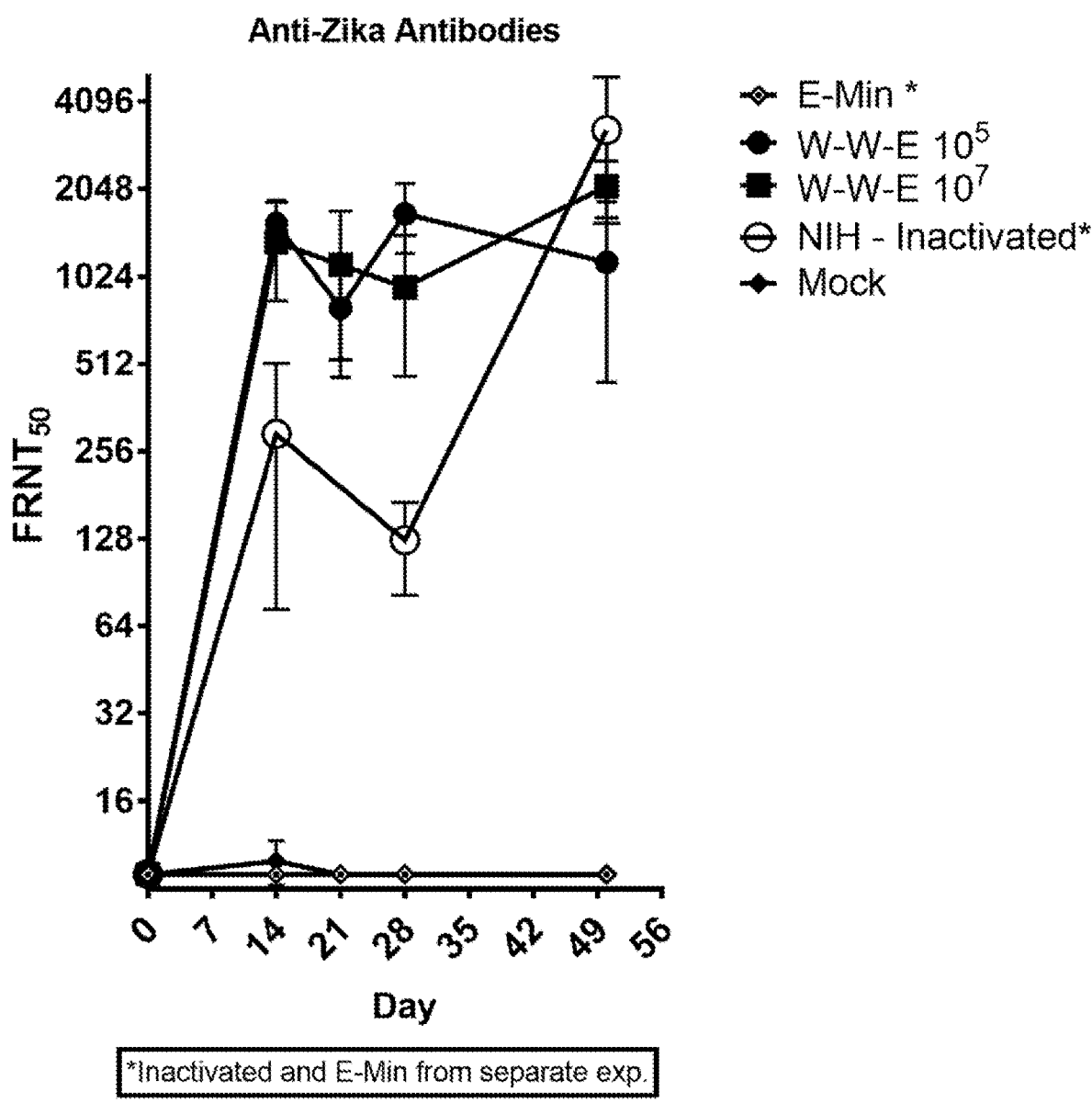
FIG. 13 describes the immunogenicity of E-W/W/Min vaccination in Cynomolgus macaques. Zika virus seronegative macaques were vaccinated with either $10^5$ or $10^7$ plaque-forming units (PFU) of E-W/W/Min delivered subcutaneously in a volume of 0.5 mL. Mock vaccinated animals were injected with 0.5 mL of vaccine diluent. Macaques were initially vaccinated on day 0, and then boosted on day 28. Serum samples were collected on days 0, 14, 21, 28, and 50 and tested for neutralizing activity against wildtype ZIKV strain MR766 using a focus-reduction neutralization 50% ($FRNT_{50}$) assay in Vero cells. Vaccination with $10^7$ or $10^5$ PFU E-W/W/Min was found to be superior to the NIH inactivated ZIKV vaccine candidate after the first vaccination and the two doses triggered comparable levels of neutralizing antibodies. All animals vaccinated with E-W/Min seroconverted by day 14 post-vaccination. No increase in $FRNT_{50}$ titer was observed post-boost on day 28, indicating sterilizing immunity that prevented secondary infection from triggering an anamnestic response. This further indicates that a single, relatively low dose, of E-W/WMin may be sufficient for triggering high levels of neutralizing antibodies (≥1,028 $FRNT_{50}$).
Figure 18:
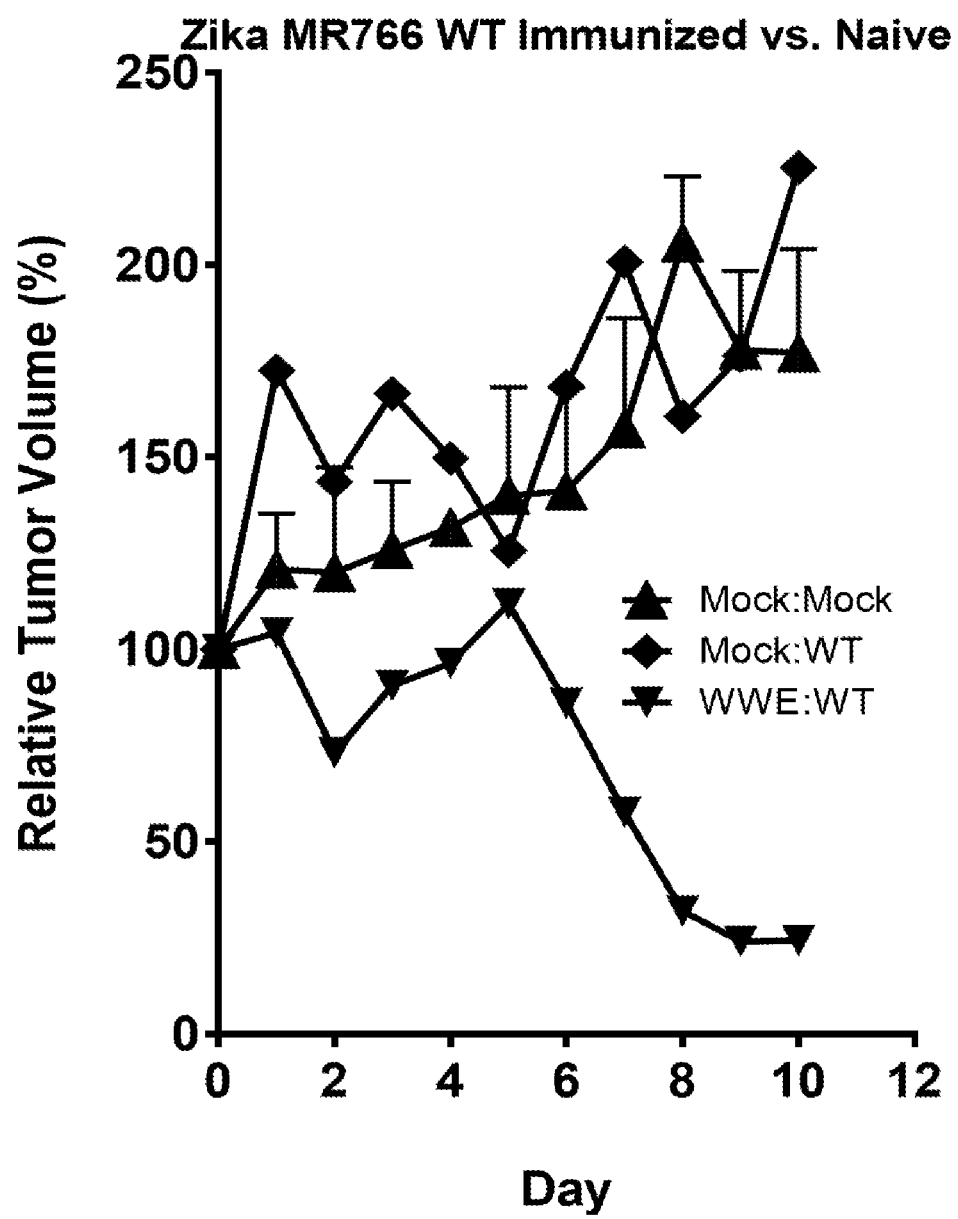
Figure 19:
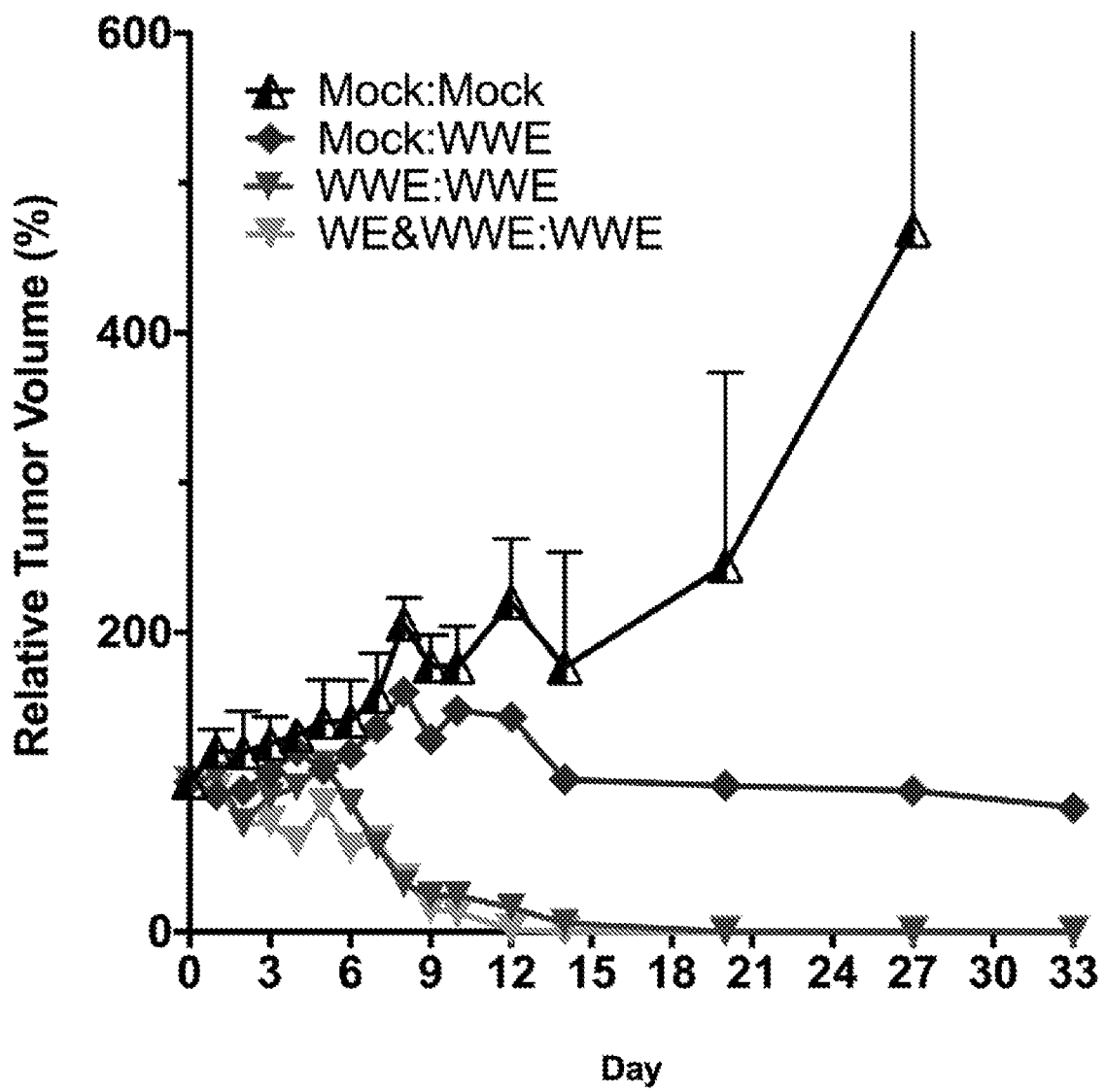
Figure 20:
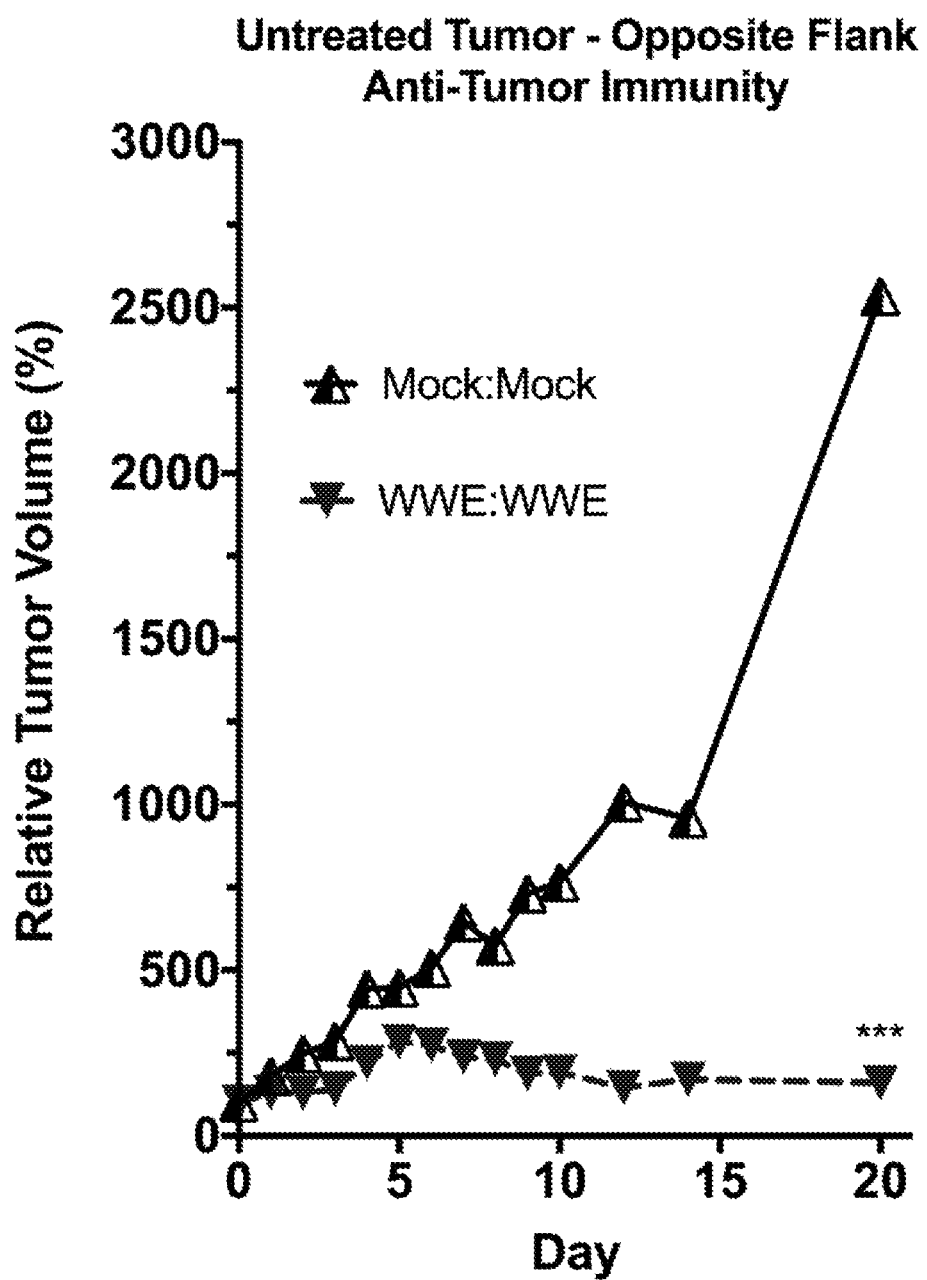
Figure 21A:
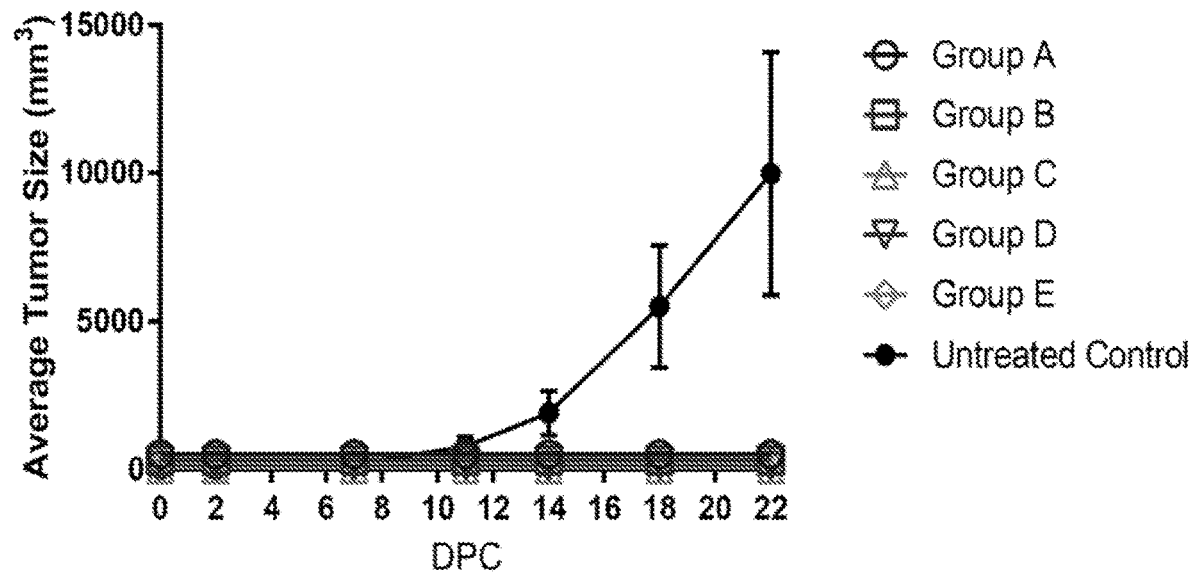
Figure 21B:
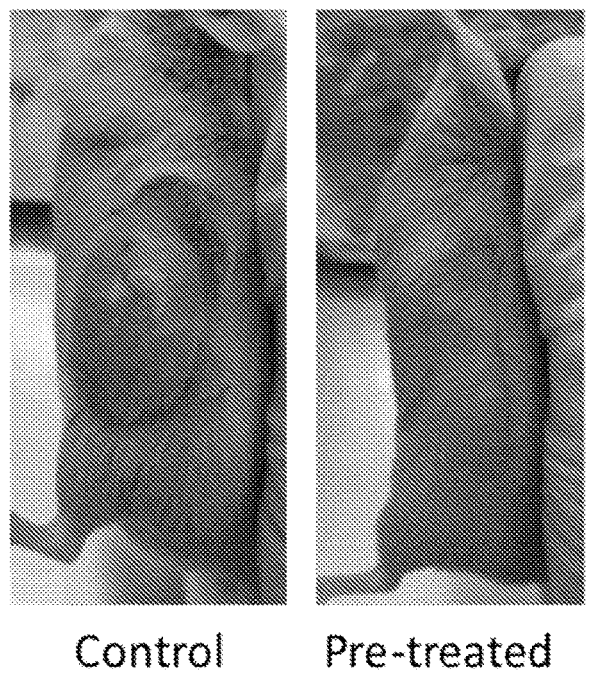
Figure 22A:
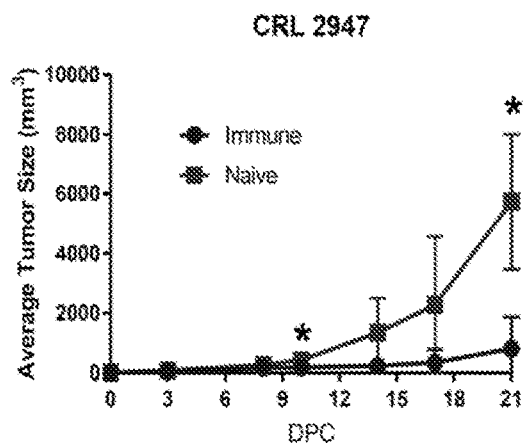
FIG. 22A-22C show Zika virus treated animals are protected from heterologous tumor rechallenge. DBA/2 mice were initially vaccinated with MR766 E-W/Min and boosted 3 times with MR766 E-W/Min. Mice in which the CCL53.1 tumors were cured by treatment with either WT or EWW were rechallenged with 22A) 1×10$^6$ CRL 2947 cells (renal cancer cells) (n=4) in both flanks (tumor sizes pooled from both flanks) or 22B) KLN-205 cells (lung cancer cells) (n=5) in the right flank and compared to naïve control DBA/2 mice (n=3). Growth of tumors in the flank were assessed over 21 days post-challenge for each group. The Y axis is the average tumor size measured as mm$^3$ and X axis is day post-challenge (DPC). Immune mice were "tumor resistant" with significantly smaller CRL 2947 tumor sizes on day 11 (p=0.0064) and 21 (p=0.0012). KLN-205 tumor sizes were also smaller at days 11 (p=0.0179) and 14 (p=0.0478) post-challenge with other time-points approaching significance (p=0.0.0532). 22C) Tumors for each mouse were photographed on day 21 (CRL 2947) and day 17 (KLN-205) post injection.
Figure 22B:
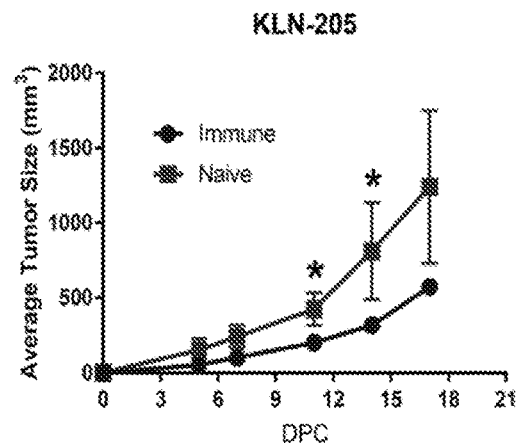
Figure 22C:
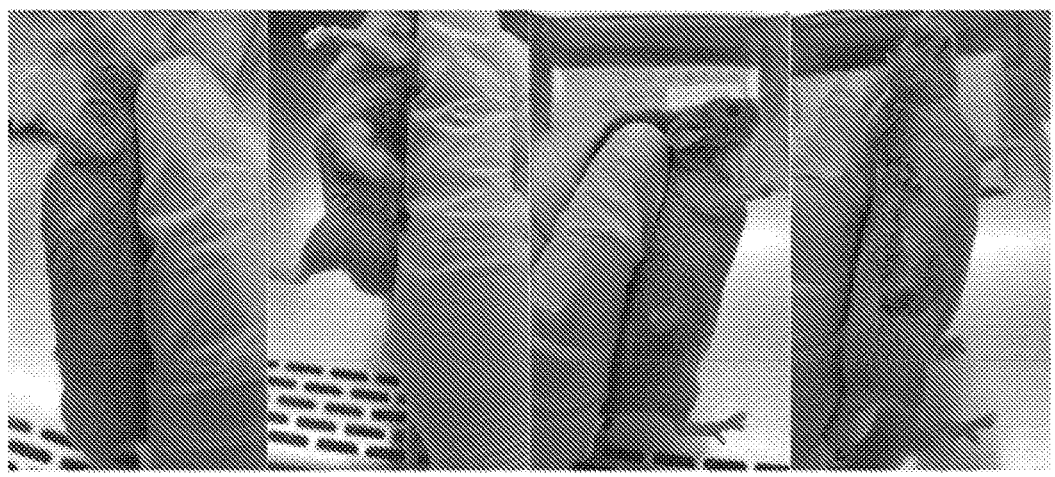
Figure 23:
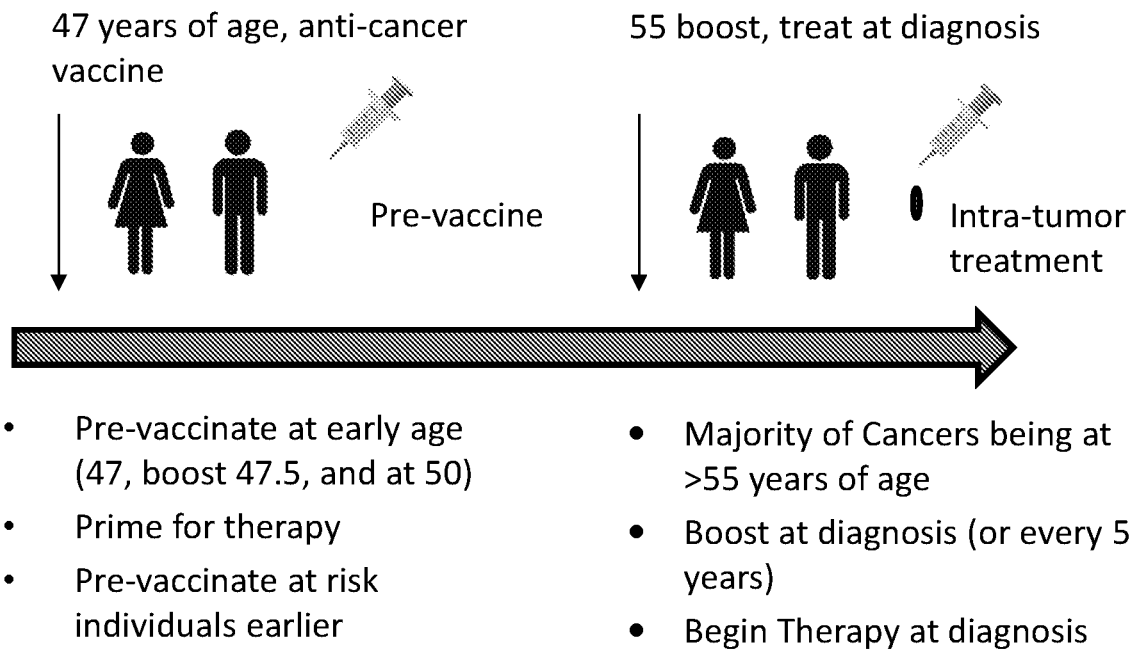
FIG. 23 shows an exemplary treatment protocol.
Figure 24:
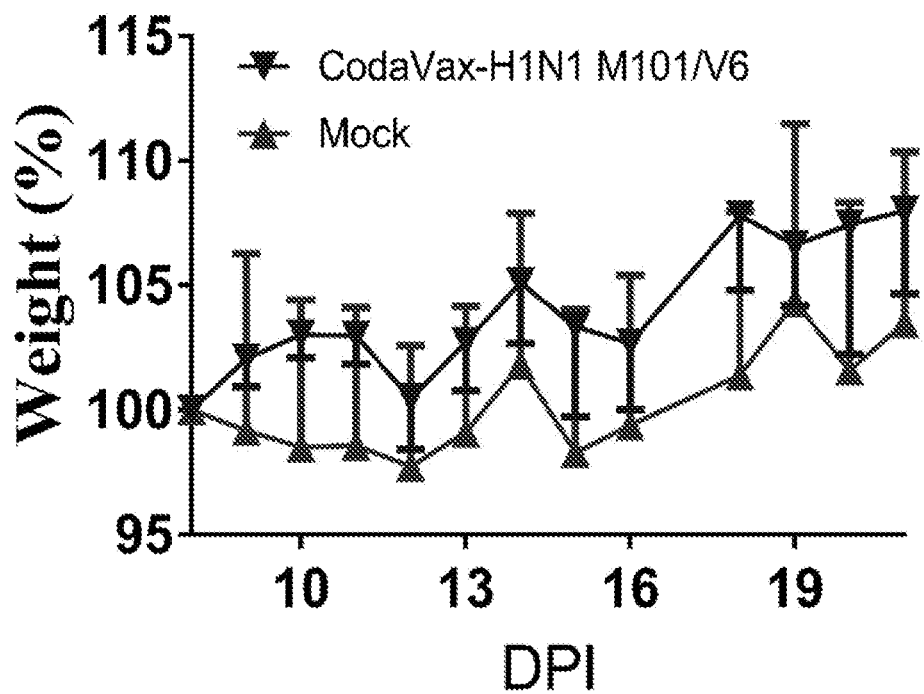
FIG. 24 depicts mortality and morbidity was not observed in CodaVax-H1N1 M101/V6 inoculated mice.
Figure 25A:
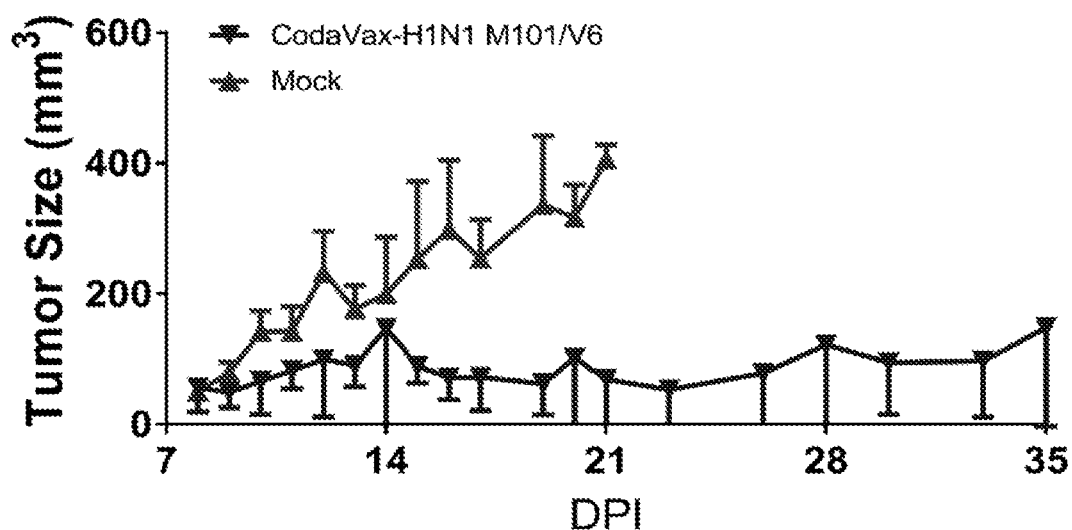
FIG. 25A-25C depicts efficacy of oncolytic CodaVax-H1N1 M101/V6 in treating implanted syngeneic 4T1 TNCB cells in Balb/C mice was observed over the course of 8 treatments of 10$^7$ PFU delivered on 8, 10, 12, 14, 16, 18, 26, and 28 days post implantation (DPI).
Figure 25B:
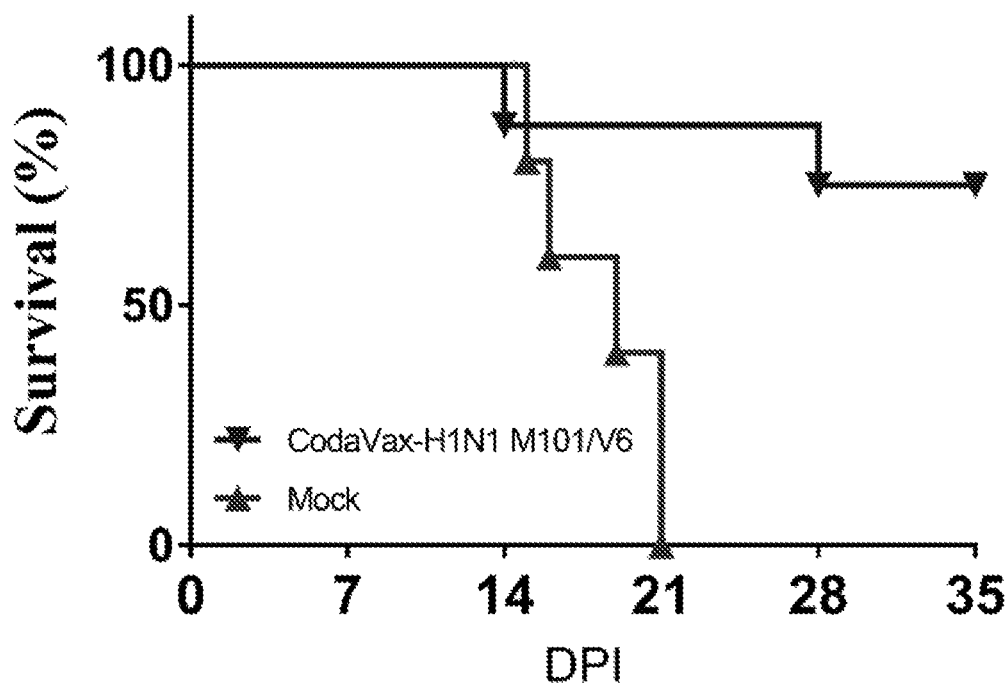
Figure 25C:
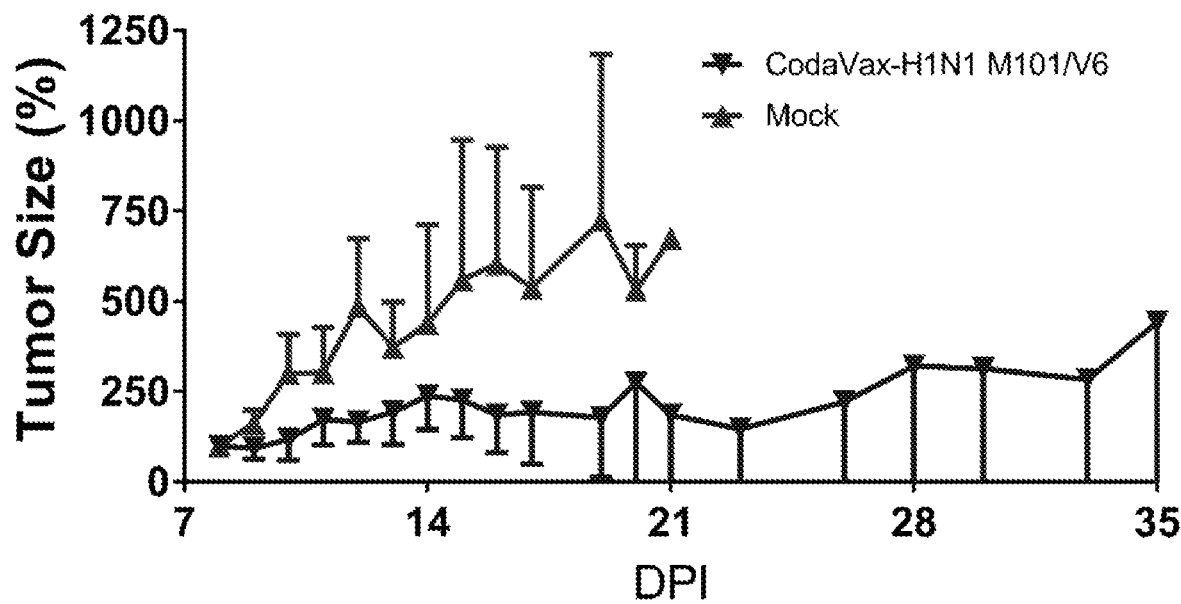
Figure 26:
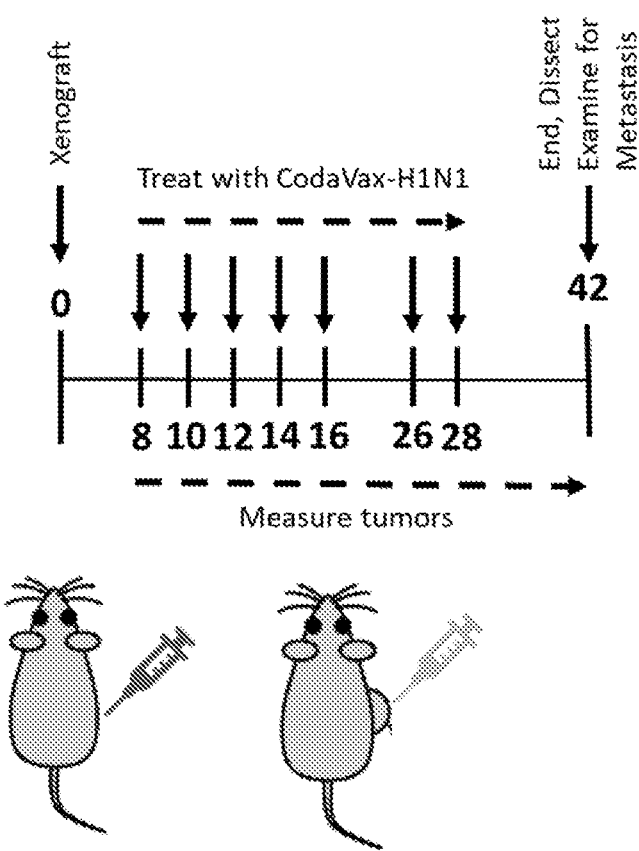
FIG. 26 depicts treatment plan of DBA/2 mice implanted subcutaneously with CCL53.1 cells. Mice were implanted on day 0 and treated on days 8, 10, 12, 14, and 16 with CodaVax-H1N1 M101/V6. Tumors were measured to monitor progress of treatment. One group of mock-treated and one-group of CodaVax-H1N1 M101/V6 treated mice were also given 0.1 mg of anti PD-1 antibody on days 3, 7, and 10 post-implantation.
Figure 27:
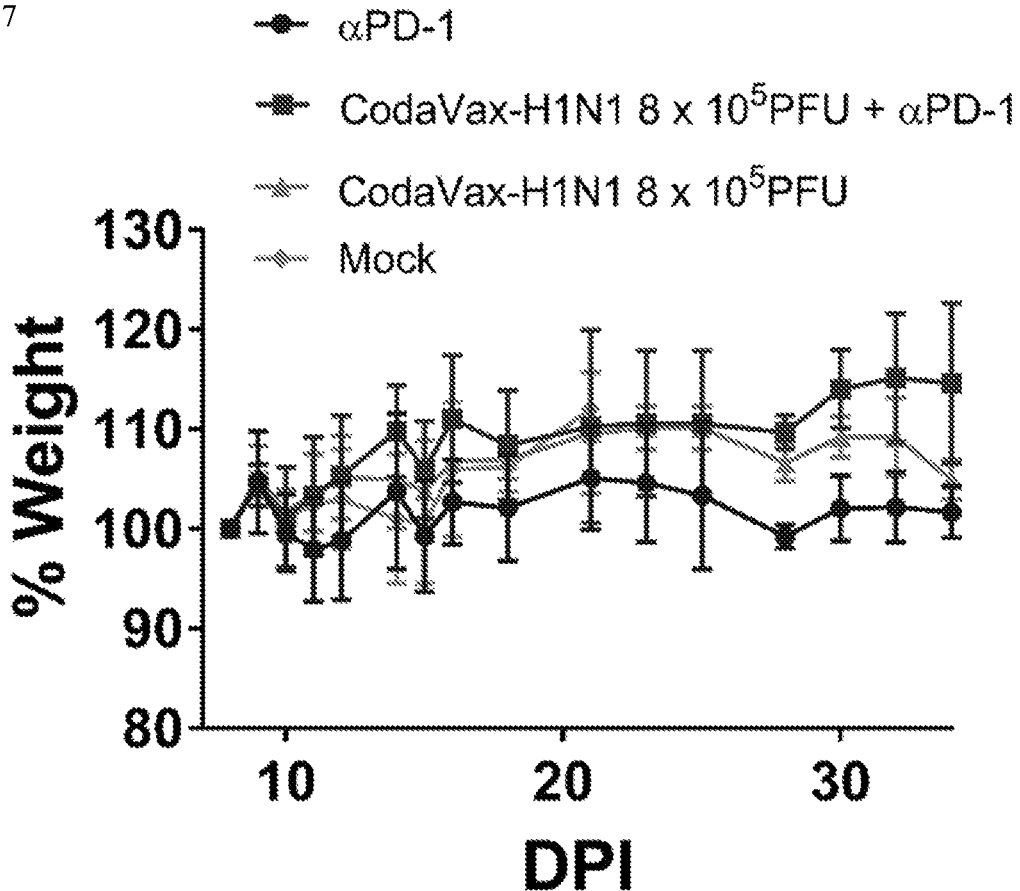
FIG. 27 shows that mortality and morbidity was not observed in CodaVax-H1N1 inoculated mice.
Figure 28:
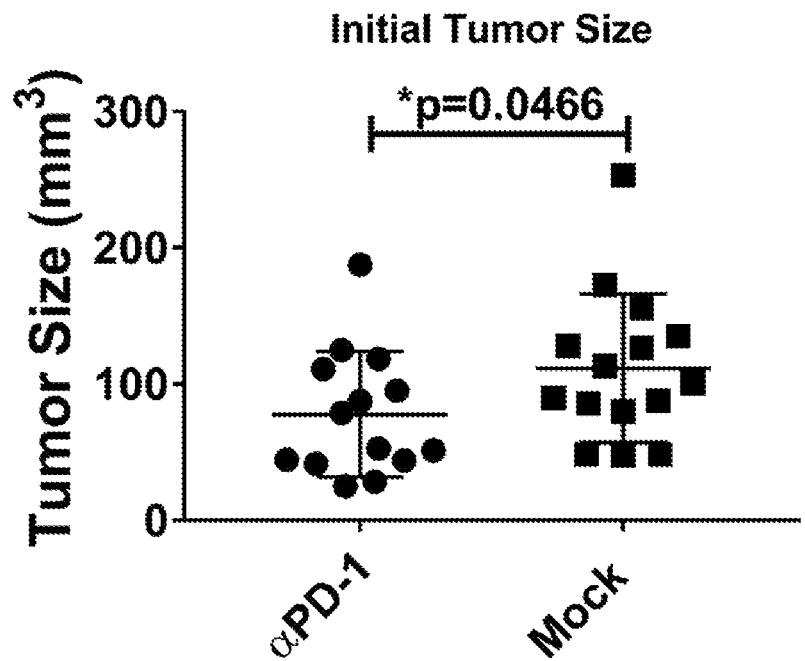
FIG. 28 depicts the comparison of tumor sizes (mm$^3$) at start of treatment on 8 DPI. Mice implanted with CCL53.1 cells that were treated on days 3 and 7 with 0.1 mg anti PD-1 antibody had smaller tumors at the start of CodaVax-H1N1 M101/V6 treatment (p=0.0466, Student's t-test).
Figure 29:
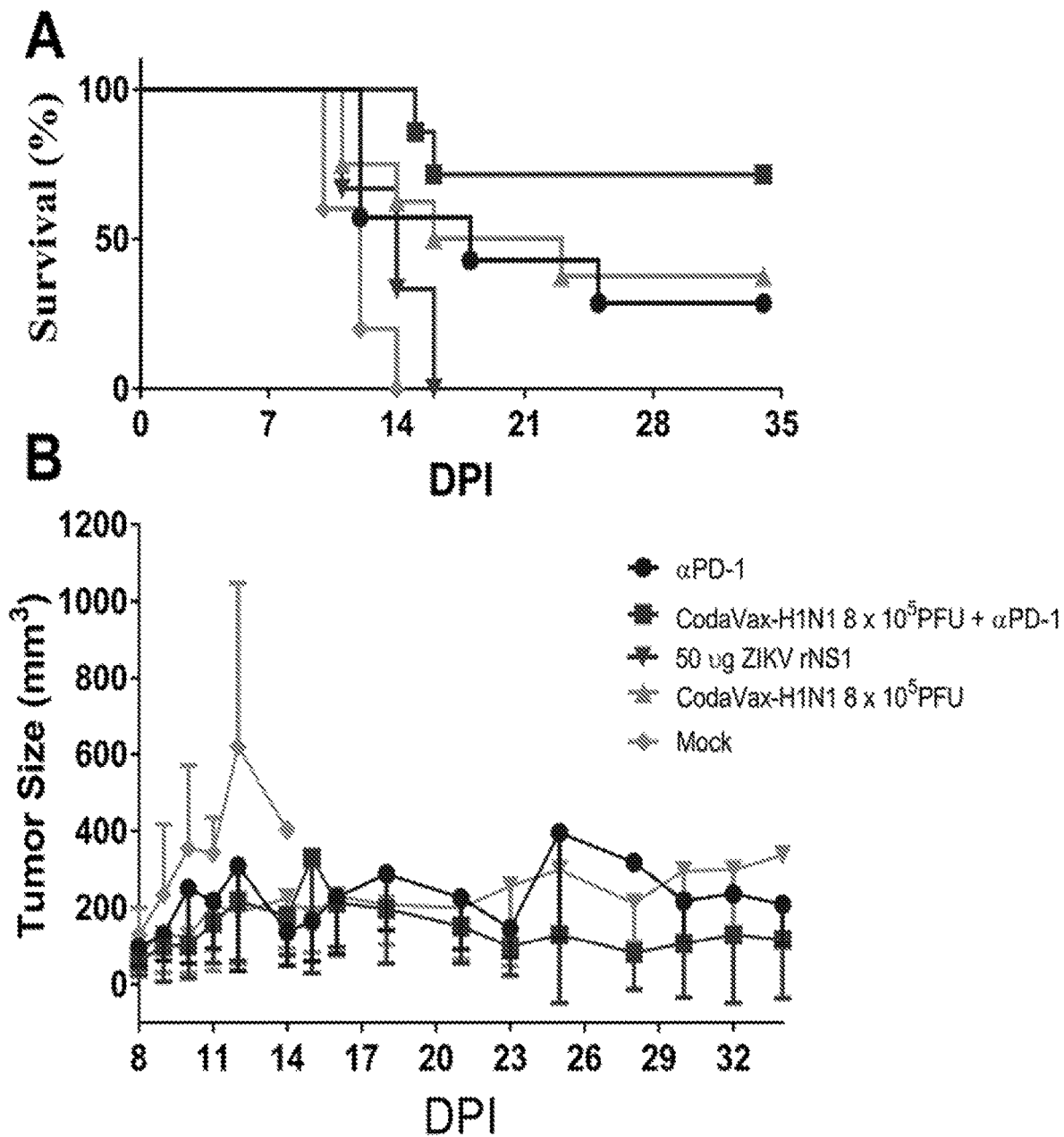
FIG. 29 shows the efficacy of oncolytic CodaVax-H1N1 M101/V6 in treating implanted syngeneic CCL53.1 melanoma cells in DBA/2 mice was observed over the course of 5 treatments of 8×10$^5$ PFU delivered on 8, 10, 12, 14, and 16 DPI. A) Survival was calculated using a humane early end point of ≥400 mm$^3$ tumor volume. Tumor size was measured and reported as volume (mm$^3$) and graphed as B) averages±standard deviation.
Figure 30:
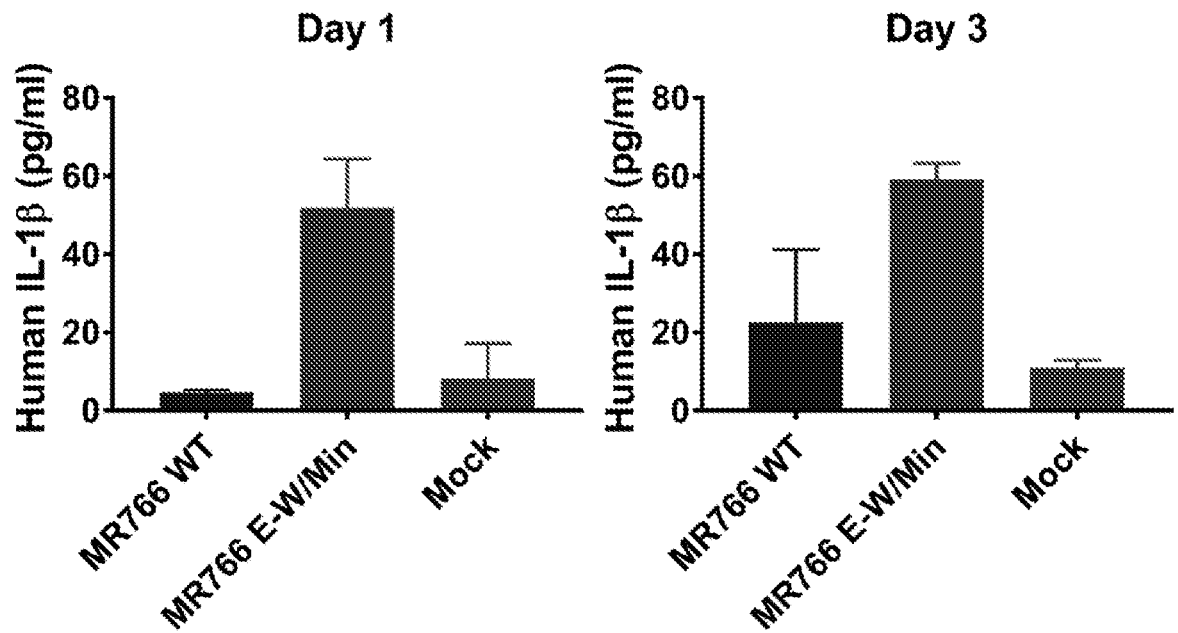
FIG. 30 shows the effects when cultured human monocytes (THP-1) were induced to differentiate into macrophages through the addition of 100 nM PMA to culture media, infected with the indicated virus and then incubated for 1 and 3 day at 37° C., 5% CO$_2$ and the secretion of IL-1B was measured in the supernatant via ELISA.
Figure 31A:
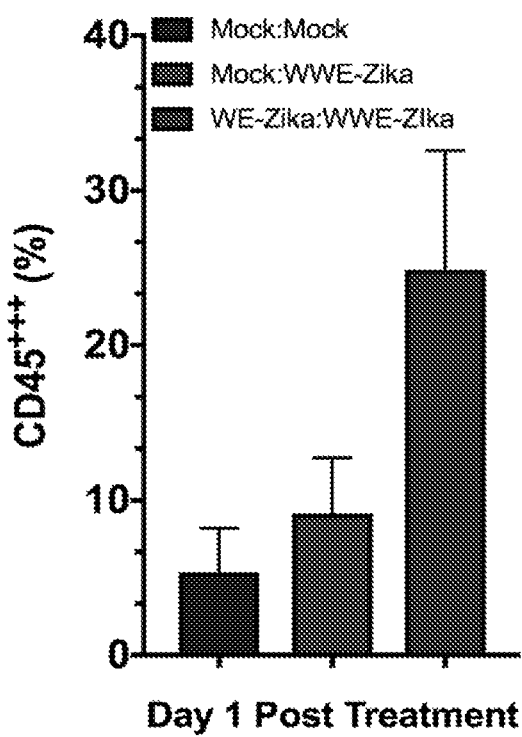
Figure 31B:
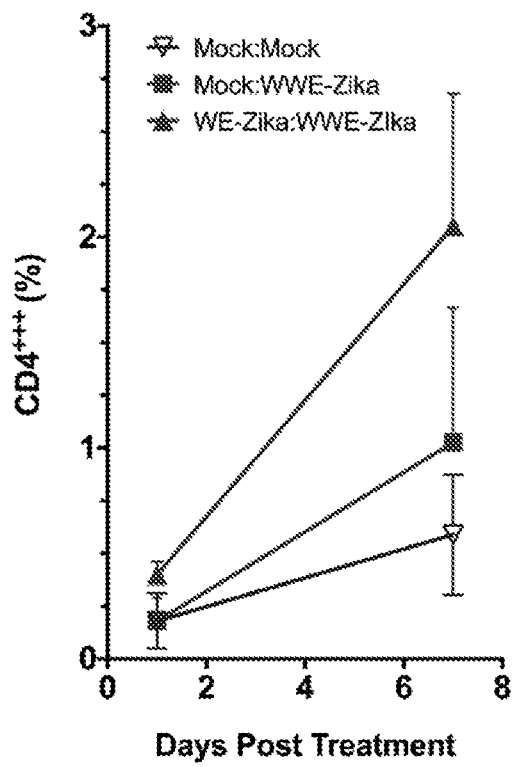
Figure 31C:
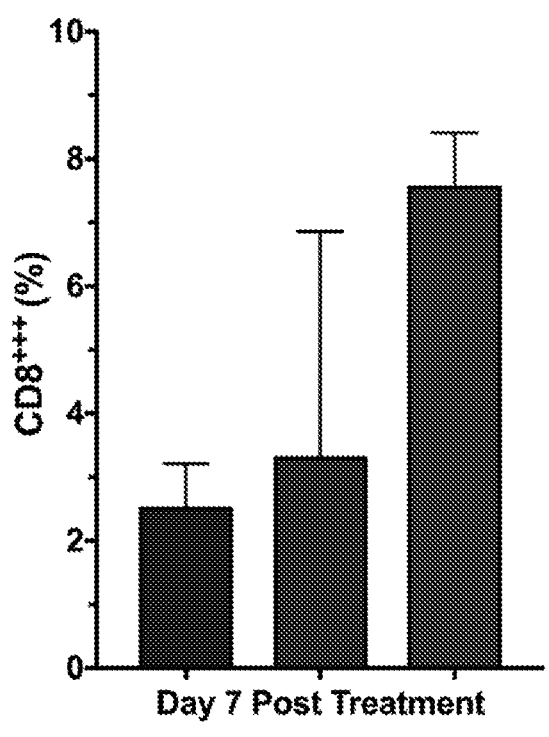
Figure 31D:
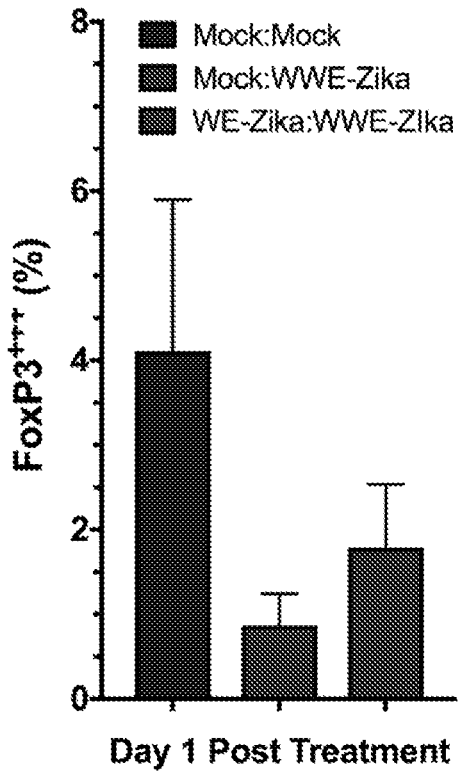

Survival, weight, and clinical sign data were collected daily throughout the course of the experiment. SAVE deoptimized PR15 and MR766 strains were highly attenuated compared to synthetic wild-type viruses, with only the MR766 NS3-Min at a dose of $10^4$ inducing death in 40% of mice. Thus, all other strains were at least 500-fold attenuated. Mice infected with $10^2$ PFU of synthetic wild-type PR15 or MR766 ZIKV experienced a dramatic weight loss just prior to death, similar to the pattern observed with "natural" wild-type ZIKV. Mice infected with $10^4$ PFU of the candidate MR766 E-Min did not experience significant weight loss or mortality (FIG. 12).

The growth phenotype and pathogenesis of the PRVABC59 E-Min and E-Min/NS3-Min variant as well as the MR766 E-Min and N53-Min was examined in an animal model. Groups of five AG129 mice received each virus at doses of $10^2$ or $10^4$ PFU subcutaneously, and body weight and survival of the animals was monitored continuously for 28 days p.i. Morbidity and mortality (weight loss, reduced activity, death) was monitored. The Lethal Dose 50 ($LD_{50}$) of the wildtype virus and the vaccine candidates was calculated by the method of Reed and Muench (Reed, L. J.; Muench, H., 1938, The American Journal of Hygiene 27: 493-497). Remarkably, the E-Min variants for PRVABC59 and MR766 and the PRVABC59 E-Min/NS3-Min virus did not induce apparent disease after a dose up to $10^4$ PFU with no mortality and minimal weight loss. Therefore, the theoretical LD50 of the E-Min variants was calculated to be equal or greater than $3.16\times10^4$ PFU, which exceeds that of wt PRVABC59 or MR766 by a factor of at least 1,000 (Table 5). The $LD_{50}$ of the MR766 NS3-Min virus was calculated to be ≤42.

TABLE 5

$LD_{50}$ and $PD_{50}$ of Attenuated Virus

| Virus | LD50 | PD50 |
|---|---|---|
| WT MR766 | $<3.16 \times 10^1$ | NA |
| MR766 E-Min | $>3.16 \times 10^4$ | $6.81 \times 10^1$ |
| MR766 NS3-Min | $<4.20 \times 10^1$ | $<6.81 \times 10^3$ |
| WT PRVABC59 | $<3.16 \times 10^1$ | NA |
| PRVABC59 E-Min | $3.16 \times 10^4$ | $1.47 \times 10^2$ |
| PRVABC59 E/NS3-Min | $3.16 \times 10^4$ | $<6.81 \times 10^3$ |

Example 14

Immunogenicity in AG129 Mice

Vaccine candidates should be capable of providing, at low dose, long-term protection from challenge with a lethal dose of wt virus equal to $10^{23}$ cell-culture infectious dose ($CCID_{50}$) per animal. Although the E-Min variants were highly attenuated in cell culture and in AG129 mice, they were successful in preventing mortality in AG129 mice after challenge with as little as 68 PFU (MR766 E-Min) or 147 PFU (PRVABC59 E-Min). We tested vaccine efficacy in the survivors of each mouse from the attenuation study. First, serum was harvested from survivors via superficial temporal vein on Day 28 and animals were boosted with the same vaccine dose a second time on Day 28. Serum was also collected on day 49 (21 days post-boost). Neutralizing antibodies from these animals were quantified using a 50% plaque reduction neutralization titer ($PRNT_{50}$) assay of serum harvested at 14, 28, and 49 days post vaccination. One half serial dilutions, starting at a 1/10 dilution, of test sera were made. Dilutions were then mixed 1:1 with $10^{2.4}$ PFU of ZIKV strain Puerto Rico 2015 PRVABC-59 (PR15). The virus-serum mixture was then added to individual wells of a 12-well tissue culture plate with Vero 76 cells. The reciprocal of the dilution of test serum that resulted in ≥50% reduction in average plaques from virus control was recorded as the $PRNT_{50}$ value. On day 28 and after only a single vaccination, MR766 E-Min was able to generate a robust antibody response to the current PR15 strain in all animals (FIG. 12). Similarly, PR15 E-Min also provided a robust antibody response after only a single vaccination.

Example 15

Efficacy in Non-Human Primates

Cynomolgus macaques (CM) are commonly used as a model for evaluating flavivirus infection including Yellow Fever, Dengue, West Nile and ZIKV. ZIKV isolates have also been recovered from naturally infected Cynomolgus macaques. Previous work suggests that while experimental ZIKV infection of CM is not likely to produce clinical disease, ZIKV can replicate and be found in blood, urine and other tissues. In a non-GLP study conducted by Southern Research, we evaluated the efficacy of live attenuated Zika virus (ZIKV) vaccine candidates in naïve CM. A total of fifteen (15) (10 male and 5 female) ZIKV seronegative CMs were randomized into five (5) treatment groups. CMs in Groups 1-4 were vaccinated using a prime-boost regimen (Days 0 and 28) by subcutaneous (SC) injection with attenuated viruses (MR766 E-W/W/Min) at doses of $10^7$ or $10^5$ PFU in a volume of 500 μL. CMs assigned to the mock control group (Group 5) received PBS via SC injection. The presence of vaccine induced anti-ZIKV neutralizing antibody (Nab) was assessed on Day 14, 21, 28, 50 and 61 by focus reduction neutralization test (FRNT). FRNT values were 2-4 times higher for MR766 E-W/W/Min (FIG. 13) vaccinated macaques compared to the NIH Inactivated vaccine after a single dose. FRNT values in W-W-E-Min vaccinated macaques did not increase after the boost on day 28, indicating that the vaccines induced sterilizing immunity that prevented further infection by the boosting virus. All animals vaccinated with E-W/W/Min seroconverted by day 14 post-vaccination. This data indicates that a single, relatively low dose, of E-W/W/Min may be sufficient for triggering high levels (≥1,028 $FRNT_{50}$).

Example 16

Oncolytic Efficacy in Immune-Competent Mice

DBA/2 mice (4-6 weeks old) were first vaccinated with MR766 E-W/W/Min, MR766 E-W/Min (at a dose of $1\times10^7$ PFU), or mock injected with OptiPro medium delivered subcutaneously dorsal to the cervical spine in a volume of 500 µL. Mice were vaccinated 5 times on Day 0, Day 14, Day 26, Day 71, and Day 85 (FIG. 14). Serum samples were collected on these days to ascertain development of neutralizing antibodies to Zika virus by plaque-reduction neutralization test 50% (PRNT50). CCL53.1 epithelial melanoma cells (DBA mouse background) were implanted into vaccinated or mock-vaccinated mice on Day 97, 11 days after the final vaccination. Implantation was done by injecting $1\times10^6$ CCL53.1 cells subcutaneously injected into the lower right flank in all animals. Some also were injected subcutaneously into the lower left flank with $2.5\times10^5$ CCL53.1 cells (FIG. 20).

Implanted mice were treated with $1\times10^7$ PFU MR766 E-W/W/Min, MR766 WT, or mock treated by injection directly into the right flank tumor only on Day 103, 10 days after tumor implantation (FIG. 15). Treatments were only performed on the right flank tumor to observe immune-mediated oncolysis of the untreated tumor. The same treatments were repeated twice more on Day 105 (12 days after tumor implantation) and Day 107 (14 days after tumor implantation). Mice were monitored for weight and tumor size measurement daily for 10 days post treatment (Days 107-117), and every other day until 20 days post treatment (118-127). Significant reduction in tumor size was observed with MR766 E-W/W/Min treatment (FIG. 15). Mock immunized: mock treated DBA/2 mouse tumors increased steadily through day 10 (FIG. 16-19). MR766 WT and MR766 E-W/W/Min treatment was effective in reducing average tumor volume in mice that were previously immunized with MR766 E-W/W/Min (FIG. 18). Both MR766 WT and MR766 E-W/W/Min treated tumors decreased in size but MR766 E-W/W/Min treatment was unexpectedly superior to MR766 WT treatment in vaccinated mice (FIG. 17). MR766 WT treated tumors in mock vaccinated mice did not improve and increased steadily. In E-W/W/Min vaccinated DBA/2 mice, MR766 WT treatment was effective in drastically reducing tumor size by day 10 (FIG. 18). MR766 E-W/W/Min treatment of tumors in mock vaccinated mice was unsuccessful, but, in MR766 E-W/W/Min and combined MR766 E-W/W/Min plus E-W/Min vaccinated DBA/2 mice, tumor size was eliminated after MR766 E-W/W/Min treatment (FIG. 19). These experiments indicate that pre-vaccination plays an essential role in successful oncolytic treatment of melanoma with Zika virus, and that tumor destruction from viral replication alone is unlikely.

In mock-vaccinated, mock treated left flank tumors, the size increased steadily throughout 10 days post treatment. Left flank tumor size was maintained in mock vaccinated, MR766 E-W/W/Min treated mice however with MR766 E-W/W/Min vaccinated, E-W/W/Min treated mice the left flank tumor size increased several-fold before being reduced again. Left flank tumors in both MR766 E-W/W/Min treated groups were significantly smaller than in mock vaccinated, mock treated animals by one-way ANOVA ($p<0.001$; FIG. 20). These experiments provide strong evidence that oncolytic treatment with MR766 E-W/W/Min can successfully control tumor growth throughout the body, not just at the site of treatment, in a small animal model.

Example 17

Codavax-H1N1 Treatment of Triple-Negative Breast Cancer Using Implanted Syngeneic 4t1 Cells in Balb/C Mice CodaVax-H1N1 was significantly attenuated as compared to wildtype Influenza A virus A/CA/04/2009 in swine as measured by absence of microscopic lung lesions at a dose of $10^5$ (2) and safe during Phase I clinical trials. In this study we sought to test the possibility of using CodaVax-H1N1 as an oncolytic agent. In this pilot experiment, we chose to use a CodaVax-H1N1 that had been passaged 101 times in MDCK cells and 6 times in Vero cells.

For the purpose of this study, Balb/C mice (n=8) were initially implanted with $10^5$ 4 T1 mammary gland tumor cells (ATCC CRL-2539) and 8 days post-implantation (DPI) treatment was initiated by injection of 100 μl containing $10^7$ PFU of CodaVax-H1N1 M101/V6. The tumors were injected again on 10, 12, 14, 16, 26, and 28 DPI. Mock control mice (n=5) were treated with vaccine diluent (0.2% BSA MEM). For mortality, early humane end-points of ≥20% weight loss or tumor growth>400 $mm^3$ were used. Sample size was based on standard deviations of tumor size observed in prior experiments and chosen using GraphPad Statmate 2 to achieve sufficient statistical power (0.80).

Mouse implantation protocol: Animal model: *Mus musculus*, Mouse Strain:

Balb/C (Taconic); Age: 8-9 weeks old (Female); Cell medium: RPMI-1640; Cell concentration: $1\times10^5$/0.1 mL (4T1).

Initially, 4T1 cells were resuspended to a concentration of $1\times10^5$/0.1 mL in RPMI-1640. Balb/C mice were shaved on the right flank and injected subcutaneously with 0.1 ml and observed until tumor size was ~40 $mm^3$ (day 8).

Tumor treatment protocol: Animal model: *Mus musculus*; Mouse Strain: Balb/C (Taconic); Age: 8-9 weeks old (Female); Virus medium: 0.2% BSA MEM; Virus concentration: $1\times10^7$/0.1 mL (CodaVax-H1N1 M101/V6)

Tumors were treated by direct injection with 0.1 ml containing CodaVax-H1N1 M101/V6 or virus medium as a control on days 8, 10, 12, 14, 16, 26, and 28 post-implantation.

No significant weight loss was detected in Balb/C mice mock-injected or treated with CodaVax-H1N1 M101/V6 nor did any inoculated mouse meet an early time-point for euthanasia due to influenza infection (FIG. 25A-25C).

By 21 DPI, all mock-injected control mice met early human endpoints due to tumor volume≥400 $mm^3$ (FIG. 25A-25C). In contrast, tumor growth was slowed and 35-day survival increased in CodaVax-H1N1 M101/V6 treated mice. Using multiple t-tests of row means (Holm-Sidak method) significantly reduced tumor size was observed on days 11 (p=0.0066), 13 (p=0.0097), 15 (p=0.0048), 16 (p=0004), 17 (p=0.0011), 19 (p=0.0004), and 21 (p=0.0099) post-implantation. Survival curve analysis using the log-rank Mantel-Cox (p=0.0052) and Gehan-Breslow-Wilcoxon tests (p=0.0138) demonstrated significantly increased survival in treated mice out to 35 DPI.

TNBC can be modeled well in Balb/C mice using 4T1 cell implantation, and has been shown to be sensitive to treatment by CodaVax-H1N1 M101/V6 in this study. Although tumor size was static or reduced for 5/8 mice, treatment was ineffective in 2 mice but completely cleared the visible tumor in 1 mouse. This data is promising, and a change in dose or frequency of administration may prove to be more successful. Importantly, no prior immunization was necessary to prime oncolytic activity by influenza A virus.

Example 18

Treatment of CCL53.1 Cells Implanted into DBA/2 Mice with Serial Intratumoral Injection of CodaVax-H1N1

CodaVax-H1N1 was significantly attenuated as compared to wildtype Influenza A virus A/CA/04/2009 in swine as measured by absence of microscopic lung lesions at a dose of $10^5$ (1) and safe during Phase I clinical trials. In this study we sought to test the possibility of using CodaVax-H1N1 as an oncolytic agent. In this pilot experiment, we chose to use a CodaVax-H1N1 that had been passaged from the master seed stock, CodaVax-H1N1 M101/V6.

For the purpose of this study, DBA/2 mice (n=7, 8) were initially implanted with $10^5$ Clone M3, Cloudman S-91 melanoma tumor cells (ATCC CCL-53.1) and 8 days post-implantation (DPI) treatment was initiated by injection of 100 μl containing either mock diluent, or $8\times10^5$ PFU of CodaVax-H1N1 (FIG. 26). The mice were also treated i.p. with mock diluent or 0.1 mg anti mouse PD-1 antibody on days 3, 7, and 10 post-implantation. The tumors were injected again on 10, 12, 14, and 16 DPI. Mock control mice (n=5) were treated with vaccine diluent (0.2% BSA MEM). For mortality, early humane end-points of ≥20% weight loss or tumor growth>400 $mm^3$ were used. Sample size was based on standard deviations of tumor size observed in prior experiments and chosen using GraphPad Statmate 2 to achieve sufficient statistical power (0.80).

Experimental Procedures:

Mouse implantation protocol: Animal model: *Mus musculus*; Mouse Strain: DBA/2 (Taconic) Age: 8-9 weeks old (Female); Cell medium: F-12K Medium; Cell concentration: $1\times10^5$/0.1 mL (CCL53.1)

Initially, CCL53.1 cells were resuspended to a concentration of $1\times10^5$/0.1 mL in F12-K medium. DBA/2 mice were shaved on the right flank and injected subcutaneously with 0.1 ml and observed until tumor size was ~100 $mm^3$ (day 8).

Tumor treatment protocol: Animal model: *Mus musculus*; Mouse Strain: DBA/2 (Taconic); Age: 8-9 weeks old (Female); Virus medium: 0.2% BSA MEM; Virus concentration: $8\times10^5$/0.1 mL (CodaVax-H1N1 P7)

Tumors were treated by direct injection with 0.1 ml containing CodaVax-H1N1 or virus medium as a control on days 8, 10, 12, 14, and 16 post-implantation.

No significant weight loss was detected in DBA/2 mice mock-injected or treated with CodaVax-H1N1 nor did any inoculated mouse meet an early time-point for euthanasia due to influenza infection (FIG. 27). Interestingly, mice injected with anti PD-1 antibody alone did not gain weight as much as the other groups including the PD-1/CodaVax-H1N1 treatment group.

When tumor size data was pooled at 8 DPI for mice treated (n=14) with anti PD-1 antibody or mock treated (n=15) with antibody diluent (days 3 and 7) it was found that tumor size was slightly but significantly decreased in the treated group (FIG. 28; p=0.0466; Student's t-test).

By 14 DPI, all mock-injected control mice met early human endpoints due to tumor volume≥400 $mm^3$ (FIG. 29). In contrast, tumor growth was slower and 34-day survival increased in CodaVax-H1N1 treated mice, PD-1 antibody treated mice, and survival significantly improved with combination therapy (p=0.0008, Gehan-Breslow-Wilcoxon test). Using multiple t-tests of row means (Holm-Sidak method) significantly reduced tumor size was observed on days 11 (p=0.0066), 13 (p=0.0097), 15 (p=0.0048), 16 (p=0004), 17 (p=0.0011), 19 (p=0.0004), and 21 (p=0.0099) post-implantation. Survival curve analysis using the log-rank Mantel-Cox (p=0.1218) and Gehan-Breslow-Wilcoxon tests (p=0.1137) demonstrated a nearly significant increase survival between mice treated with PD-1 antibody alone or in combination with CodaVax-H1N1. Survival curves were highly similar (p>0.9999, Gehan-Breslow-Wilcoxon test) between PD-1 antibody treated and CodaVax-H1N1 treated mice.

Melanoma can be modeled well in DBA/2 mice using CCL53.1 cell implantation(2), and has been shown to be somewhat sensitive to treatment by CodaVax-H1N1 or PD-1 antibody alone in this study. This data is promising, and a change in dose or frequency of administration may prove to be more successful. Importantly, no prior immunization was necessary to prime oncolytic activity by influenza A virus and it was more highly effective in combination with PD-1 therapy.

Example 19

Modified Viruses Stimulate IL-1B

As seen in FIG. 30, cultured human monocytes (THP-1) were induced to differentiate into macrophages through the addition of 100 nM PMA to culture media and incubation for 3 days as 37° C., 5% $CO_2$. After adhering to individual wells of a 12-well plate at a density of 350,000 cells/well the medium was replaced with fresh, warmed, culture media (10% FBS RPMI-1640) and the cells infected at a MOI of 5.0 ($1.75\times10^6$ FFU) in a volume of 250 μl. The cells were rocked at 30 minutes at room temperature, then a further 250 μl of culture medium was added and the plates incubated at 37° C., 5% $CO_2$ for 2 hours after which the virus inoculum was removed, and the media replaced with warm culture media. At 1 and 3 days post-infection supernatant samples were collected, frozen at −80° C. and tested for human IL-1β ELISA using a quantitative kit (Thermo Fisher Catalog #BMS224-2). IL-1β was chosen as a member of the interleukin 1 family of cytokines that is produced by activated macrophages and is an important mediator of the inflammatory response. IL-1β production is activated following recognition of viral RNA by retinoic acid induced gene 1 (RIG-I) and subsequent induction of NFκB-IRF3 signaling. Activation of RIG-I is also known to induce STING expression and through a positive feedback mechanism, promote a sustained inflammatory response.

Example 20

Recruitment of Immune Cells to the Tumor

As seen in FIG. 31, immune cell activation was assayed in implanted and treated DBA/2 mice either vaccinated on days 0, 14, 28, and 42 with $10^7$ FFU MR766 E-W/Min or else mock-vaccinated with virus diluent. Vaccinated and mock-vaccinated mice were implanted on day 63 with $1\times10^6$ CCL53.1 melanoma cells delivered by the subcutaneous route and treatment was initiated on day 73 with $10^7$ PFU MR766 E-W/W/Min or virus diluent delivered intratumorally on days 73, 75, and 77. Tumors were harvest and fixed in 4% paraformaldehyde on days 1 and 7 post-treatment (Days 74 and 80) for immunohistochemistry and staining to count immune markers and measure CD4+, CD8+, CD45+, and FoxP+ cell infiltration. CD8+ cell infiltration in implanted CCL53.1 tumors 7 days post-treatment was enhanced by prior MR766 E-W/Min vaccination as visualized by immunohistochemistry. CD45+ cell infiltration in implanted CCL53.1 tumors 1 day post-treatment was greatly increased in DBA/2 mice with prior MR766 E-W/Min vaccination as visualized by immunohistochemistry. FoxP3+ cells were reduced in treated tumors.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of treating a malignant tumor, comprising:
administering a modified virus having a modified virus sequence to a subject in need thereof, wherein the modified virus is directly derived from a wild-type virus by substituting at least one genomic region of the wild-type virus with a codon-pair deoptimized region encoding a same protein to produce the modified virus sequence, wherein the codon pair bias of the modified virus sequence is less than the codon pair bias of the wild-type virus sequence, and wherein the codon pair bias of the modified virus sequence is reduced by at least about 0.05, or at least about 0.1, or at least about 0.2, compared to that of the wild-type virus sequence, and wherein codon pair bias (CPB) is calculated by the following formula:

$$CPB = \sum_{i=1}^{k} \frac{CPSi}{k-1}$$

for a sequence k amino acids in length, with CPS representing the codon pair score,
wherein the modified virus is optionally also modified by substituting at least one genomic region of the wild-type virus with a region with increased CpG di-nucleotide encoding a same protein sequence, wherein in the increase of the CpG di-nucleotide is at least 41 instances above the wild-type viral genome, or at least 21 instances above the wild-type viral genome, or is optionally also modified by substituting at least one genomic region of the wild-type virus with a region with increased UpA di-nucleotide encoding a same protein sequence, wherein in the increase of the UpA di-nucleotide is at least 26 instances above the wild-type viral genome, or at least 13 instances above the wild-type viral genome, or is optionally also modified by substituting at least one genomic region of the wild-type virus with a region with increased UpA and the CpG di-nucleotide encoding a same protein sequence, wherein in the increase of the UpA and the CpG di-nucleotide was at least 42 instances combined above the wild-type viral genome, wherein the modified virus is a modified influenza virus, and
wherein the wild-type virus is an influenza A virus, and wherein the modified virus comprises SEQ ID NO:5 or SEQ ID NO:6.

2. A method of treating a malignant tumor, comprising:
administering a prime dose of a modified virus having a modified virus sequence to a subject in need thereof; and administering one or more boost dose of a modified virus having the modified virus sequence to the subject in need thereof, wherein the prime dose and boost dose of the modified virus are directly derived from a wild-type virus by substituting at least one genomic region of the wild-type virus with a codon-pair deoptimized region encoding a same protein sequence to produce the modified virus sequence, wherein the codon pair bias of the modified virus sequence is less than the codon pair bias of the wild-type virus sequence, and is reduced by at least about 0.05, or at least about 0.1, or at least about 0.2, compared to that of the wild-type virus sequence, and wherein codon pair bias (CPB) is calculated by the following formula:

$$CPB = \sum_{i=1}^{k} \frac{CPSi}{k-1}$$

for a sequence k amino acids in length, with CPS representing the codon pair score, wherein the modified virus is optionally also modified by substituting at least one genomic region of the wild-type virus with a region with increased CpG di-nucleotide encoding a same protein sequence, wherein in the increase of the CpG di-nucleotide is at least 41 instances above the wild-type viral genome, or at least 21 instances above the wild-type viral genome, or optionally also modified by substituting at least one genomic region of the wild-type virus with a region with increased UpA di-nucleotide encoding a same protein sequence, wherein in the increase of the UpA di-nucleotide is at least 26 instances above the wild-type viral genome, or at least 13 instances above the wild-type viral genome, or optionally also modified by substituting at least one genomic region of the wild-type virus with a region with increased UpA and the CpG di-nucleotide encoding a same protein sequence, wherein in the increase of the UpA and the CpG di-nucleotide was at least 42 instances combined above the wild-type viral genome, wherein the modified virus is a modified influenza virus, and wherein the wild-type virus is an influenza A virus, wherein the modified virus comprises SEQ ID NO:5 or SEQ ID NO:6.

3. The method of claim 2, wherein the prime dose is administered subcutaneously, intramuscularly, intradermally, intranasally, or intravenously, and wherein the one or more boost dose is administered intratumorally or intravenously.

4. The method of claim 2, wherein the subject has cancer.

5. The method of claim 2, wherein the prime dose is administered when the subject does not have cancer.

6. The method of claim 1, wherein the method further comprises administering a PD-1 inhibitor or a PD-L1 inhibitor.

7. The method of claim 1, wherein treating the malignant tumor decreases the likelihood of recurrence of the malignant tumor.

8. The method of claim 1, wherein treating the malignant tumor decreases the likelihood of having a second cancer that is different from the malignant tumor, or wherein if the subject develops a second cancer that is different from the malignant tumor, the treatment of the malignant tumor results in slowing the growth of the second cancer, or wherein after remission of the malignant tumor, if the subject develops a second cancer that is different from the malignant tumor, the treatment of the malignant tumor results in slowing the growth of the second cancer.

9. The method of claim 1, wherein treating the malignant tumor stimulates an inflammatory immune response in the tumor, or wherein treating the malignant tumor recruits pro-inflammatory cells to the tumor, or wherein treating the malignant tumor stimulates an antitumor immune response.

10. A method of treating the malignant tumor of claim 1, wherein the malignant tumor is a solid tumor.

11. A method of treating the malignant tumor of claim 1, wherein the malignant tumor is glioblastoma, adenocarcinoma, melanoma, lung carcinoma, neuroblastoma, breast cancer, bladder cancer, colon cancer, prostate cancer, or liver cancer.

* * * * *